US008853385B2

(12) United States Patent
Ueta et al.

(10) Patent No.: US 8,853,385 B2
(45) Date of Patent: Oct. 7, 2014

(54) COMBINATION THERAPY COMPRISING SGLT INHIBITORS AND DPP4 INHIBITORS

(75) Inventors: Kiichiro Ueta, Osaka (JP); Kenji Arakawa, Osaka (JP); Yasuaki Matsushita, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 451 days.

(21) Appl. No.: 12/863,429

(22) PCT Filed: Jan. 16, 2009

(86) PCT No.: PCT/JP2009/051023
§ 371 (c)(1),
(2), (4) Date: Jul. 16, 2010

(87) PCT Pub. No.: WO2009/091082
PCT Pub. Date: Jul. 23, 2009

(65) Prior Publication Data
US 2011/0059912 A1  Mar. 10, 2011

Related U.S. Application Data

(60) Provisional application No. 61/021,777, filed on Jan. 17, 2008.

(51) Int. Cl.
*C07H 7/04* (2006.01)

(52) U.S. Cl.
CPC .......................................... *C07H 7/04* (2013.01)
USPC ...................... 536/27.13; 536/1.11

(58) Field of Classification Search
None
See application file for complete search history.

(56) References Cited

U.S. PATENT DOCUMENTS

| | | | |
|---|---|---|---|
| 4,160,861 A | 7/1979 | Cole et al. | |
| 4,584,369 A | 4/1986 | Klein et al. | |
| 5,149,838 A | 9/1992 | Humphrey et al. | |
| 5,424,406 A | 6/1995 | Tsujihara et al. | |
| 5,731,292 A | 3/1998 | Tsujihara et al. | |
| 5,767,094 A | 6/1998 | Tsujihara et al. | |
| 5,780,483 A | 7/1998 | Widdowson et al. | |
| 5,830,873 A | 11/1998 | Tsujihara et al. | |
| 6,048,842 A | 4/2000 | Tsujihara et al. | |
| 6,107,317 A | 8/2000 | Villhauer | |
| 6,110,949 A | 8/2000 | Villhauer | |
| 6,153,632 A | 11/2000 | Rieveley | |
| 6,172,081 B1 | 1/2001 | Damon | |
| 6,297,363 B1 | 10/2001 | Kubo et al. | |
| 6,303,661 B1 | 10/2001 | Demuth et al. | |
| 6,414,126 B1 | 7/2002 | Ellsworth et al. | |
| 6,515,117 B2 | 2/2003 | Ellsworth et al. | |
| 6,562,791 B1 | 5/2003 | Maurya et al. | |
| 6,617,313 B1 | 9/2003 | Maurya et al. | |
| 6,627,611 B2 | 9/2003 | Tomiyama et al. | |
| 6,710,040 B1 | 3/2004 | Hulin et al. | |
| 6,846,922 B1 * | 1/2005 | Manoharan et al. | 536/25.34 |
| 6,849,622 B2 | 2/2005 | Yasuda et al. | |
| 7,060,722 B2 | 6/2006 | Kitajima et al. | |
| 7,074,794 B2 * | 7/2006 | Kitajima et al. | 514/252.12 |
| 7,138,397 B2 * | 11/2006 | Yasuda et al. | 514/254.01 |
| 7,375,213 B2 | 5/2008 | Deshpande et al. | |
| 7,511,022 B2 | 3/2009 | Beavers et al. | |
| 7,943,788 B2 * | 5/2011 | Nomura et al. | 549/60 |
| 8,222,219 B2 * | 7/2012 | Nomura et al. | 514/23 |
| 2001/0041674 A1 | 11/2001 | Tomiyama et al. | |
| 2002/0032164 A1 | 3/2002 | Dale et al. | |
| 2002/0052326 A1 | 5/2002 | Washburn | |
| 2002/0111315 A1 | 8/2002 | Washburn et al. | |
| 2003/0024914 A1 | 2/2003 | Aleshin | |
| 2003/0064935 A1 | 4/2003 | Gougoutas | |
| 2003/0087843 A1 | 5/2003 | Washburn | |
| 2003/0114390 A1 | 6/2003 | Washburn et al. | |
| 2003/0139434 A1 | 7/2003 | Balkan et al. | |
| 2003/0166578 A1 * | 9/2003 | Arch et al. | 514/19 |
| 2004/0053855 A1 | 3/2004 | Fujikura et al. | |
| 2004/0063646 A1 | 4/2004 | Fujikura et al. | |
| 2004/0063935 A1 | 4/2004 | Yasuda et al. | |
| 2004/0106655 A1 | 6/2004 | Kitajima et al. | |
| 2004/0110936 A1 | 6/2004 | Ohsumi et al. | |
| 2004/0116357 A1 | 6/2004 | Fushimi et al. | |
| 2004/0132669 A1 | 7/2004 | Nishimura et al. | |
| 2004/0138143 A1 | 7/2004 | Glombik et al. | |
| 2004/0180925 A1 | 9/2004 | Matsuno et al. | |
| 2004/0259819 A1 | 12/2004 | Frick et al. | |
| 2004/0259883 A1 | 12/2004 | Sakashita et al. | |
| 2005/0014704 A1 | 1/2005 | Frick et al. | |
| 2005/0032711 A1 | 2/2005 | Patel et al. | |
| 2005/0032712 A1 | 2/2005 | Urbanski | |
| 2005/0037980 A1 | 2/2005 | Rybczynski et al. | |
| 2005/0037981 A1 | 2/2005 | Beavers et al. | |
| 2005/0054678 A1 | 3/2005 | Yasuda et al. | |
| 2005/0065098 A1 | 3/2005 | Fujikura et al. | |
| 2005/0124556 A1 | 6/2005 | Burton | |
| 2005/0137143 A1 | 6/2005 | Fujikura et al. | |

(Continued)

FOREIGN PATENT DOCUMENTS

| CA | 2494177 A1 | 2/2004 |
|---|---|---|
| CA | 2581673 A1 | 3/2006 |

(Continued)

OTHER PUBLICATIONS

U.S. Appl. No. 13/494,602, filed Jun. 2012, Nomura et al.*
Biessels et al., "Increased risk of Alzheimer's disease in Type II diabetes: insulin resistance of the brain or insulin-induced amyloid pathology?" Biochemical Society Transactions (2005) vol. 33 part 5, pp. 1041-1044.*

(Continued)

*Primary Examiner* — Eric S Olson
(74) *Attorney, Agent, or Firm* — Birch, Stewart, Kolasch & Birch, LLP

(57) ABSTRACT

The present invention relates to combination therapy comprising a DPP4 inhibitor and an SGLT inhibitor. The combination of the present invention leads to increase plasma GLP-1 level and the combination is useful for prevention or treatment of conditions such as diabetes and diseases related to diabetes.

7 Claims, No Drawings

(56) References Cited

U.S. PATENT DOCUMENTS

| | | |
|---|---|---|
| 2005/0176771 A1 | 8/2005 | Hayakawa et al. |
| 2005/0203030 A1 | 9/2005 | Demuth et al. |
| 2005/0233988 A1* | 10/2005 | Nomura et al. ............ 514/43 |
| 2005/0245538 A1 | 11/2005 | Kitajima et al. |
| 2006/0035841 A1 | 2/2006 | Eckhardt et al. |
| 2006/0106087 A1 | 5/2006 | Fukushima et al. |
| 2006/0217323 A1 | 9/2006 | Patel et al. |
| 2006/0229260 A1 | 10/2006 | Rybczynski et al. |
| 2006/0229286 A1 | 10/2006 | Kakigami et al. |
| 2006/0234954 A1 | 10/2006 | Urbanski |
| 2006/0293251 A1 | 12/2006 | Urbanski et al. |
| 2007/0060545 A1 | 3/2007 | Nomura et al. |
| 2007/0167501 A1 | 7/2007 | Fukuda et al. |
| 2007/0197449 A1 | 8/2007 | Fushimi et al. |
| 2007/0265320 A1 | 11/2007 | Fukuda et al. |
| 2007/0281940 A1 | 12/2007 | Dugi et al. |
| 2008/0139484 A1 | 6/2008 | Teranishi et al. |
| 2008/0188426 A1 | 8/2008 | Fushimi et al. |
| 2009/0082256 A1 | 3/2009 | Abe et al. |
| 2009/0326215 A1 | 12/2009 | Eckhardt et al. |
| 2010/0093825 A1 | 4/2010 | Fukuda et al. |
| 2011/0282058 A1 | 11/2011 | Yoshida et al. |

FOREIGN PATENT DOCUMENTS

| | | | |
|---|---|---|---|
| EP | 0355750 A1 | 2/1990 | |
| EP | 0579204 A3 | 1/1994 | |
| EP | 1082314 B1 | 4/2003 | |
| EP | 1 323 710 A1 | 7/2003 | |
| EP | 1338603 A1 | 8/2003 | |
| EP | 1528066 A1 | 5/2005 | |
| EP | 1 803 721 A1 | 7/2007 | |
| EP | 1 803 729 A1 | 7/2007 | |
| GB | 2359554 A | 8/2001 | |
| JP | 63-233975 A | 9/1988 | |
| JP | 4-253974 A | 9/1992 | |
| JP | 9-263549 A | 10/1997 | |
| JP | 10-324632 A | 12/1998 | |
| JP | 2000-34230 A | 2/2000 | |
| JP | 2000-34239 A | 2/2000 | |
| JP | 2001-288178 A | 10/2001 | |
| JP | 2002-265439 A | 9/2002 | |
| JP | 2003-12686 A | 1/2003 | |
| JP | 2003-520226 | 7/2003 | |
| JP | 2003-535898 | 12/2003 | |
| WO | WO 93/21178 A1 | 10/1993 | |
| WO | WO 95/15309 A1 | 6/1995 | |
| WO | WO 97/25033 A1 | 7/1997 | |
| WO | WO 97/40832 A1 | 11/1997 | |
| WO | WO 98/19998 A2 | 5/1998 | |
| WO | WO 99/51431 A1 | 12/1999 | |
| WO | WO 00/34241 A1 | 6/2000 | |
| WO | WO 00/74681 A1 | 12/2000 | |
| WO | WO 01/16147 A1 | 3/2001 | |
| WO | WO 01/27128 A1 | 4/2001 | |
| WO | WO 01/40180 A2 | 6/2001 | |
| WO | WO 01/64669 A1 | 9/2001 | |
| WO | WO 01/68603 A2 | 9/2001 | |
| WO | WO 01/68660 A1 | 9/2001 | |
| WO | WO 01/74834 A1 | 10/2001 | |
| WO | WO 01/74835 A1 | 10/2001 | |
| WO | WO 01/81304 A1 | 11/2001 | |
| WO | WO 01/81337 A1 | 11/2001 | |
| WO | WO 01/96295 A3 | 12/2001 | |
| WO | WO 02/14271 A1 | 2/2002 | |
| WO | WO 02/28872 A1 | 4/2002 | |
| WO | WO 02/30890 A1 | 4/2002 | |
| WO | WO 02/30891 A1 | 4/2002 | |
| WO | WO 02/051836 A1 | 7/2002 | |
| WO | WO 02/053573 A1 | 7/2002 | |
| WO | WO 02/068439 A1 | 9/2002 | |
| WO | WO 02/068440 A1 | 9/2002 | |
| WO | WO 02/070020 A2 | 9/2002 | |
| WO | WO 02/078450 A1 | 10/2002 | |
| WO | WO 02/083066 A2 | 10/2002 | |
| WO | WO 02/083128 A1 | 10/2002 | |
| WO | WO 02/088157 A1 | 11/2002 | |
| WO | WO 02/094262 A1 | 11/2002 | |
| WO | WO 03/000250 A1 | 1/2003 | |
| WO | WO 03/000712 A1 | 1/2003 | |
| WO | WO 03/002530 A2 | 1/2003 | |
| WO | WO 03/002531 A2 | 1/2003 | |
| WO | WO 03/002553 A2 | 1/2003 | |
| WO | WO 03/004498 A1 | 1/2003 | |
| WO | WO 03/011880 A1 | 2/2003 | |
| WO | WO 03/015775 A1 | 2/2003 | |
| WO | WO 03/020737 A1 | 3/2003 | |
| WO | WO 03/024942 A1 | 3/2003 | |
| WO | WO 03/035057 A1 | 5/2003 | |
| WO | WO 03/043621 A1 | 5/2003 | |
| WO | WO 03/087104 A1 | 10/2003 | |
| WO | WO 03/099836 A1 | 12/2003 | |
| WO | WO 2004/007517 A1 | 1/2004 | |
| WO | WO 2004/009544 A1 | 1/2004 | |
| WO | WO 2004/013118 A1 | 2/2004 | |
| WO | WO 2004/014931 A1 | 2/2004 | |
| WO | WO 2004/018442 A1 | 3/2004 | |
| WO | WO 2004/019958 A1 | 3/2004 | |
| WO | WO 2004/020407 A1 | 3/2004 | |
| WO | WO 2004/052902 A1 | 6/2004 | |
| WO | WO 2004/052903 A1 | 6/2004 | |
| WO | WO 2004/063209 A2 | 7/2004 | |
| WO | WO 2004/067509 A1 | 8/2004 | |
| WO | WO 2004/080990 A1 | 9/2004 | |
| WO | WO 2004/067053 A2 | 10/2004 | |
| WO | WO 2004/087727 A1 | 10/2004 | |
| WO | WO 2004/099230 A1 | 11/2004 | |
| WO | WO 2004/103993 A1 | 12/2004 | |
| WO | WO 2004/113359 A1 | 12/2004 | |
| WO | WO 2005/012249 A2 | 2/2005 | |
| WO | WO 2005/012326 A1 | 2/2005 | |
| WO | WO 2005/026148 A1 | 3/2005 | |
| WO | WO 2005/030127 A2 | 4/2005 | |
| WO | WO 2005/030751 A2 | 4/2005 | |
| WO | WO 2005/037828 A1 | 4/2005 | |
| WO | 2005-170792 A | 6/2005 | |
| WO | WO 2005/076421 A1 | 8/2005 | |
| WO | WO 2005/076426 A1 | 8/2005 | |
| WO | WO 2005/077900 A1 | 8/2005 | |
| WO | WO 2005/082847 A1 | 9/2005 | |
| WO | WO 2005/085265 A1 | 9/2005 | |
| WO | WO 2005/085267 A1 | 9/2005 | |
| WO | WO 2005/092877 A1 | 10/2005 | |
| WO | WO 2005/095381 A1 | 10/2005 | |
| WO | WO 2006/034489 A2 | 3/2006 | |
| WO | WO 2006/035796 A1 | 4/2006 | |
| WO | WO 2006/073167 A1 | 7/2006 | |
| WO | WO 2006/129785 A1 | 7/2006 | |
| WO | WO 2006/080577 A1 | 8/2006 | |
| WO | WO 2006/088129 A1 | 8/2006 | |
| WO | WO 2006/090244 A1 | 8/2006 | |
| WO | WO 2006/100096 A2 | 9/2006 | |
| WO | WO 2006/104356 A1 | 10/2006 | |
| WO | WO 2006/108842 A1 | 10/2006 | |
| WO | WO 2006/116157 A2 | 11/2006 | |
| WO | WO 2006/117359 A1 | 11/2006 | |
| WO | WO 2006/117360 A1 | 11/2006 | |
| WO | WO 2006/120208 A1 | 11/2006 | |
| WO | WO 2007/035198 A2 | 3/2007 | |
| WO | WO 2007/054978 A2 | 5/2007 | |
| WO | WO 2007/107354 A1 | 9/2007 | |
| WO | WO 2007/140191 A2 | 12/2007 | |
| WO | WO 2008/013321 A1 | 1/2008 | |
| WO | WO 2008/013322 A1 | 1/2008 | |
| WO | WO 2008/131149 A2 | 10/2008 | |
| WO | WO 2009/022009 A1 | 2/2009 | |
| WO | WO 2009/022010 A1 | 2/2009 | |
| WO | WO 2010/092125 A1 | 8/2010 | |

OTHER PUBLICATIONS

Bansal et al., "Diabetic neuropathy" Postgarduate medical journal (2006) vol. 82 pp. 95-100.*

(56) References Cited

OTHER PUBLICATIONS

Grieg et al., "New Therapeutic Strategies and Drug Candidates for Neurodegenerative Diseases" Ann NY Acad Sci (2004) vol. 1035 pp. 290-315.*
Perry et al., "Protection and Reversal of Excitotoxic Neuronal Damage by Glucagon-Like Peptide-1 and Exendin-4" The Journal of Pharmacology and Experimental Therapeutics (2002) vol. 302 No. 3 pp. 881-888.*
Holst et al., "The Physiology of Glucagon-Like Peptide 1" Physiol Rev (2007) vol. 87 pp. 1409-1439.*
Gilman et al., "Glucagon-like peptide 1 modulates calcium responses to glutamate and membrane depolarization in hippocampal neurons" Journal of Neurochemistry (2003) vol. 87 pp. 1137-1144.*
Merriam-Webster's Collegiate Dictionary, Tenth Edition, published 1998 by Merriam-Webster, Incorporated, p. 924.*
"FDA Approves DPP-IV inhibitor sitagliptin for typr 2 diabetes" Endocrinology today (2006) downloaded from http://www.healio.com/...s/news/print/endocrine-today/%7B4BC43BFA-8889-4300-8E3C-E143D8DDC1CF%7D/FDA-approves-DPP-IV-inhibitor-sitagliptin-for-type-2-diabetes.*
Office Action for Canadian Application No. 2,712,614, dated Mar. 7, 2012.
International Search Report—dated Apr. 14, 2009 for PCT/JP2009/051023.
"Comprehensive Handbook of Endocrinology" ECSMO Publishing House, 2007, pp. 691-693, with English translation.
Russian Office Action for Application No. 2010134362/15 dated Aug. 23, 2011, with English translation.
Ahmad et al., "Synthesis and Structure Determination of Some Oxadiazole-2-Thione and Triazole-3-Thione Galactosides", Nucleosides, Nucleotides & Nucleic Acids, vol. 20, No. 9, 2001, pp. 1671-1682.
Amishiro et al., "Synthesis and Antitumor Activity of Duocarmycin Derivatives: A-Ring Pyrrole Compounds Bearing 5-Membered Heteroarylacryloyl Groups," Chem. Pharm. Bull., Oct. 1999, vol. 47, No. 10, pp. 1393-1403.
Appleton et al, "A Mild and Selective C-3 Reductive Alkylation of Indoles", Tetrahedron Letters, vol. 34, No. 9, 1993, pp. 1529-1532.
Banker et al. (Editors), Modern Pharmaceutics, Third Edition, published 1996, p. 596, Marcel Dekker, Inc.
Benhaddou et al.,"Tetra-n-propylammonium tetraoxoruthenate(VII): a reagent of choice for the oxidation of diversely protected glycopyranoses and glycofuranoses to lactones", Carbohydrate Research, vol. 260, 1994, pp. 243-250.
Bertolini et al., "A New Simple One-Pot Regioselective Preparation of Mixed Diesters of Carbonic Acid", Journal of Organic Chemistry, vol. 63, No. 17, 1998, pp. 6031-6034.
Blair et al., "Effect of Ring Fluorination on the Pharmacology of Hallucinogenic Tryptamines", J. Med. Chem., vol. 43, 2000, pp. 4701-4710.
Boehm et al., "Novel Inhibitors of DNA Gyrase: 3D Structure Based Biased Needle Screening, Hit Validation by Biophysical Methods, and 3D Guided Optimization. A Promising Alternative to Random Screening," J. Med. Chem., vol. 43, No. 14, 2000, pp. 2664-2674.
Bookser, "2-Benzyloxymethyl-5-(tributylstannyl)tetrazole. A reagent for the preparation of 5-aryl- and 5-heteroaryl-1H-tetrazoles via the Stille reaction," Tetrahedron Letters, 2000, vol. 41, pp. 2805-2809.
Bouillon et al, "Synthesis of novel halopyridinylboronic acids and esters. Part 3: 2, or 3-Halopyridin-4-yl-boronic acids and esters," Tetrahedron, 2002, vol. 58, pp. 4369-4373.
Bouillon et al, "Synthesis of novel halopyridinylboronic acids and esters. Part 4: Halopyridin-2-yl-boronic acids and esters are stable, crystalline partners for classical Suzuki cross-coupling," Tetrahedron, 2003, vol. 59, pp. 10043-10049.
Brooks et al., "Boron Trichloride/Tetra-n-Butylammonium Iodide: A Mild, Selective Combination Reagent for the Cleavage of Primary Alkyl Aryl Ethers", J. Org. Chem., vol. 64, 1999, pp. 9719-9721.
CAS Reg. No. 487001-40-1, IPOrganisers, Entered STN Feb. 7, 2003, pp. 1-2.
Cicchillo et al, "A convenient synthesis of glycosyl chlorides from sugar hemiacetals using triphosgene as the chlorine source," Carbohydrate Research, 2000, vol. 328, pp. 431-434.
Clayden et al, "Dearomatizing Cyclization of Arylsulfonylalkoxymethyl Lithiums: A Route to the Podophyllotoxin Skeleton," Organic Letters, 2003, vol. 5, No. 6, pp. 831-834.
Comins et al., "Synthesis of 3-Substituted Indoles Via N-Acylindolium Ions", Tetrahedron Letters, vol. 27, No. 17, 1986, pp. 1869-1872.
Cottet et al, "Recommendable Routes to Trifluoromethyl-Substituted Pyridine- and Quinolinecarboxylic Acids," Eur. J. Org. Chem., 2003, pp. 1559-1568.
Czernecki et al., "C-Glycosides. 7. Stereospecific C-Glycosylation of Aromatic and Heterocyclic Rings", J. Org. Chem., vol. 54, 1989, pp. 610-612.
De Las Heras et al, "Alkylating Nucleosides 1. Synthesis and Cytostatic Activity of N-Glycosyl(halomethyl)-1,2,3-triazoles. A New Type of Alkylating Agent," Journal of Medicinal Chemistry, vol. 22, No. 5, 1979, pp. 496-501.
Deeg et al., "Pioglitazone and Rosiglitazone Have Different Effects on Serum Lipoprotein Particle Concentrations and Sizes in Patients With Type 2 Diabetes and Dyslipidemia", Diabetes Care, vol. 30, No. 10, Oct. 2007, pp. 2458-2464.
Deetjen et al., "Renal Handling of D-Glucose and Other Sugars", Textbook of Nephrology, vol. 1, 3rd Edition, 1995, pp. 90-94.
Devivar et al., "Benzimidazole Ribonucleosides: Design, Synthesis, and Antiviral Activity of Certain 2-(Alkylthio)- and 2-(Benzylthio)-5,6-dichloro-1-(β-D-ribofuranosyl)benzimidazoles," J. Med. Chem., vol. 37, 1994, pp. 2942-2949.
Dewynter et al., "Synthesis of Pseudonucleosides containing Chiral Sulfahydantoins as Aglycone (II)", Tetrahedron, vol. 52, No. 3, 1996, pp. 993-1004.
Dillard et al., "Indole Inhibitors of Human Nonpancreatic Secretory Phospholipase A2. 1. Indole-3-acetamides", J. Med. Chem., vol. 39, 1996, pp. 5119-5136.
Dondoni et al., "Stereoselective synthesis of C-glycosylphosphonates from their ketols. Reconsideration of an abandoned route", Tetrahedron: Asymmetry, vol. 11, 2000, pp. 305-317.
Dondoni et al., "Thiazole-Based Synthesis of Formyl C-Glycosides", J. Org. Chem., vol. 59, 1994, pp. 6404-6412.
Dudash, Jr. et al, "Glycosylated dihydrochalcones as potent and selective sodium glucose co-transporter 2 (SGLT2) inhibitors," Bioorganic & Medicinal Chemistry Letters, vol. 14, 2004, pp. 5121-5125.
Dunn et al., "Analgetic and Antiinflammatory 7-Aroylbenzofuran-5-ylacetic Acids and 7-Aroylbenzothiophene-5-ylacetic Acids.", Journal of Med. Chem., vol. 29, No. 1, 1986, pp. 2326-2329.
Eid et al., "Reaction of Some 1,2,4-Triazines with Acetobromoglucose", Arch. Pharm. (Weinheim), vol. 323, 1990, pp. 243-245.
Ellsworth et al, "Aglycone exploration of C-arylglucoside inhibitors of renal sodium-dependent glucose transporter SGLT2," Bioorganic & Medicinal Chemistry Letters, vol. 18, 2008, pp. 4770-4773.
Ellsworth et al., "C-Arylglucoside synthesis: triisopropylsilane as a selective reagent for the reduction of an anomeric C-phenyl ketal," Tetrahedron: Asymmetry, vol. 14, 2003, pp. 3243-3247.
Frahn et al, "Functionalized AB-Type Monomers for Suzuki Polycondensation," Synthesis, Nov. 1997, pp. 1301-1304.
Fresneda et al., "Synthesis of the indole alkaloids meridianins from the tunicate Aplidium meridianum," Tetrahedron, vol. 57, 2001, pp. 2355-2363.
Fuller et al, "Thienothiophenes. Part 2. Synthesis, metallation and bromine-lithium exchange reactions of thieno[3,2-b]thiophene and its polybromo derivatives," J. Chem. Soc., Perkin Trans. 1., 1997, pp. 3465-3470.
Ganesh et al, "Synthesis and biological evaluation of fluorescently labeled epothilone analogs for tubulin binding studies," Tetrahedron, 2003, vol. 59, pp. 9979-9984.
Gershell, "Type 2 diabetes market", Nature Reviews, Drug Discovery, vol. 4, May 2005, pp. 367-368.

(56) References Cited

OTHER PUBLICATIONS

Gohier et al, "ortho-Metalation of Unprotected 3-Bromo and 3-Chlorobenzoic Acids with Hindered Lithium Dialkylamides," J. Org. Chem., 2003, vol. 68, pp. 2030-2033.

Goodman & Gilman's The Pharmacological Basis of Therapeutics, 10th Edition, McGraw-Hill Medical Publishing Division, 2001, pp. 54-57.

Gronowitz et al, "Some Substitution Reactions of 1-(2-Thienyl)pyrazole and 1-(3'-Thienyl)pyrazole," Chemica Scripta., 1978-1979, vol. 13, pp. 157-161.

Gros et al, "Efficient and Regioselective Access to Bis-heterocycles via Palladium-Catalysed Coupling of Organostannanes and Organozincates Derived from C-6 Lithiated 2-Methoxypyridine," Synthesis, 1999, No. 5, pp. 754-756.

Han et al., "Dapagliflozin, a Selective SGLT2 Inhibitor, Improves Glucose Homeostasis in Normal and Diabetic Rats", Diabetes, vol. 57, Jun. 2008, pp. 1723-1729.

Handlon, "Sodium glucose co-transporter 2 (SGLT2) inhibitors as potential antidiabetic agents," Expert Opin. Ther. Patents, vol. 15, No. 11, 2005, pp. 1531-1540.

Hofslokken et al., "Convenient Method for the ortho-Formylation of Phenols.", Acta Chemica Scandinavia, vol. 53, 1999, pp. 258-262.

Hongu et al., "Na+-Glucose Cotransporter Inhibitors as Antidiabetic Agents. II.1) Synthesis and Structure-Activity Relationships of 4'-Dehydroxyphlorizin Derivatives", Chem. Pharm. Bull., vol. 46, No. 1, 1998, pp. 22-33.

Horton et al., "Synthetic Routes to Higher-Carbon Sugars. Reaction of Lactones with 2-Lithio-1,3-Dithiane", Carbohydrate Research, vol. 94, 1981, pp. 27-41.

Hu et al., "A New Approach Towards the Yellowing Inhibition of Mechanical Pulps. Part I: Selective Removal of alpha-Hydroxyl and alpha-Carbonyl Groups in Lignin Model Compounds", Holzforschung, vol. 53, No. 1, 1999, pp. 43-48.

Huang-Minlon, "Reduction of Steroid Ketones and other Carbonyl Compounds by Modified Wolff-Kishner Method", J. Am. Chem. Soc., vol. 71, Oct. 1949, pp. 3301-3303.

Ibrahim et al., "Selective Synthesis and Structure of 2-N- and 3-S-Glucosyl-1,2,4-Triazoles of Potential Biological Interest", Carbohydrate Letters, vol. 3, No. 5, 1999, pp. 331-338.

Ibrahim, "Facile Approach for the Selective Glycosidation of Cyclic Asymmetric Amides and Thioamides", Carbohydrate Letters, vol. 1, 1996, pp. 425-432.

Information Submission of Sep. 1, 2009 in U.S. Appl. No. 11/045,446, including Appendices A, B and C.

International Search Report for Application No. PCT/JP2004/011312, dated Nov. 25, 2004.

Isaji, "Sodium-glucose cotransporter inhibitor for diabetes," Current Opinion in Investigational Drugs, vol. 8, No. 4, 2007, pp. 285-292.

Kanai et al., "The Human Kidney Low Affinity Na+/Glucose Cotransporter SGLT2: Delineation of the Major Renal Reabsorptive Mechanism for D-Glucose", J. Clin. Invest., Jan. 1994, vol. 93, pp. 397-404.

Kasahara et al., "A missense mutation in the Na+/glucose cotransporter gene SGLT1 in a patient with congenital glucose-galactose malabsorption: normal trafficking but inactivation of the mutant protein," Biochimica et Biophysica Acta, vol. 1536, 2001, pp. 141-147.

Katz et al., "Quantitative Insulin Sensitivity Check Index: A Simple, Accurate Method for Assessing Insulin Sensitivity in Humans.", J. Clin. Endocrinology & Metabolism, vol. 85, No. 7, 2000, pp. 2402-2410.

Ketcha et al., "Synthesis of Alkyl-Substituted N-Protected Indoles via Acylation and Reductive Deoxygenation" J. Org. Chem., vol. 54, 1989, pp. 4350-4356.

Khan et al, "Reactions of Phenyl-Substituted Heterocyclic Compounds—II. Nitrations and Brominations of 1-Phenylpyrazole Derivatives," Canadian Journal of Chemistry, vol. 41, 1963, pp. 1540-1547.

Lee et al, "Synthesis and In Vitro Activity of Novel Isoxazolyl Tetrahydropyridinyl Oxazolidinone Antibacterial Agents," Bioorganic & Medicinal Chemistry Letters, vol. 13, 2003, pp. 4117-4120.

Liang et al., "JNJ-28431754/TA-7284, an Inhibitor of Sodium-Glucose Cotransporter 2, Ameliorates Diabetic Syndrome in the Zucker Diabetic Fatty Rat," Oct. 2009, Poster presented at International Diabetes Federation 20th World Diabetes Congress, Montreal, Canada.

Liang et al., "JNJ-28431754/TA-7284, an SGLT Inhibitor, Lowers Blood Glucose and Reduces Body Weight in Obese and Type 2 Diabetic Animal Models," presented at the American Diabetes Association 69th Scientific Sessions, Jun. 5-9, 2009, New Orleans, Louisiana.

Lin et al., "Syntheses of Guanidinoglycosides with the Inventive use of Mitsunobu Conditions and 1,8-Diazabicyclo[5.4.0]undec-7-ene", Synthesis, No. 2, 2003, pp. 255-261.

Link et al., "A method for preparing C-glycosides related to phlorizin", Tetrahedron Letters, vol. 41, 2000, pp. 9213-9217.

Lipscombe et al., "Trends in diabetes prevalence, incidence, and mortality in Ontario, Canada 1995-2005: a population-based study", Lancet, vol. 369, Mar. 2007, pp. 750-756.

Maatooq et al., "C-p-Hydroxybenzoylglycoflavones from Citrullus Colocynthis", Phytochemistry, vol. 44, No. 1, Jan. 1997, pp. 187-190.

Mackenzie et al., "Biophysical Characteristics of the Pig Kidney Na+/Glucose Cotransporter SGLT2 Reveal a Common Mechanism for SGLT1 and SGLT2", J. Biol. Chem., vol. 271, No. 5, Dec. 1996, pp. 32678-32683.

Manis et al., "Metabolism of 4,4'-Methylenebis(2-chloroaniline) by Canine Liver and Kidney Slices", Drug Metabolism and Disposition, vol. 14, No. 2, 1986, pp. 166-174.

Marsenic, "Glucose Control by the Kidney: An Emerging Target in Diabetes", Am. J. Kidney Diseases, vol. 53, No. 5, May 2009, pp. 875-883.

Matsuda et al., "Insulin Sensitivity Indices Obtained From Oral Glucose Tolerance Testing: Comparison with the euglycemic insulin clamp," Diabetes Care, vol. 22, No. 9, Sep. 1999, pp. 1462-1470.

Matthews et al., "Homeostasis model assessment: insulin resistance and β-cell function from fasting plasma glucose and insulin concentrations in man," Diabetolgia, vol. 28, 1985, pp. 412-419.

Meanwell et al., "Regiospecific Functionalization of 1,3-Dihydro-2H-benzimidazol-2-one and Structurally Reated Cyclic Urea Derivates", J. Org. Chemistry, vol. 60, No. 6, 1995, pp. 1565-1582.

Meng et al., "Discovery of Dapagliflozin: A Potent, Selective Renal Sodium-Dependent Glucose Cotransporter 2 (SGLT2) Inhibitor for the Treatment of Type 2 Diabetes", J. Med. Chem., vol. 51, No. 5, 2008, pp. 1145-1149.

Messaoudi et al, "Synthesis and biological evaluation of oxindoles and benzimidazolinones derivatives," European Journal of Medicinal Chemistry, vol. 39, 2004, pp. 453-458.

Mewshaw et al., "New Generation Dopaminergic Agents. 7. Heterocyclic Bioisosteres that Exploit the 3-OH-Phenoxyehylamine D2 Template", Bioorganic & Medicinal Chemistry Letters, vol. 9, 1999, pp. 2593-2598.

Miyaura et al., "Palladium-Catalyzed Cross-Coupling Reactions of Organoboron Compounds", Chem. Rev., vol. 95, No. 7, 1995, pp. 2457-2483.

Nishimura et al, "Tissue-specific mRNA Expression Profiled of Human ATP-binding Cassette and Solute Carrier Transporter Superfamilies," Drug Metab. Pharmacokinet., vol. 20, No. 6, 2005, pp. 452-477.

Nomura et al., "Discovery of Novel C-glucosides with Thiophene Ring as Sodium-dependent Glucose Cotransporter 2 Inhibitors for the Treatment of Type 2 Diabetes Mellitus", MEDI 151, Abstract, 238th ACS Nat. Meeting, Washington, DC, Aug. 16-20, 2009; American Chemical Society: Washington, DC.

Nomura, "Renal Sodium-Dependent Glucose Cotransporter 2 (SGLT2) Inhibitors for New Anti-Diabetic Agent," Current Topics in Medicinal Chemistry, vol. 10, No. 4, 2010, pp. 411-418.

Office Action in U.S. Appl. No. 11/045,446, dated Dec. 5, 2008.

Office Action in U.S. Appl. No. 11/045,446, dated Jun. 16, 2008.

Office Action in U.S. Appl No. 11/045,446, dated Oct. 1, 2009.

(56) References Cited

OTHER PUBLICATIONS

Ohsumi et al. "Pyrazole-O-Glucosides as Novel Na+-Glucose Cotransporter (SGLT) Inhibitors" Bioorganic & Medicinal Chemistry Letters, vol. 13, 2003, pp. 2269-2272.
Oku et al., "T-1095, an Inhibitor of Renal Na+-Glucose Cotransporters, May Provide a Novel Approach to Treating Diabetes", Diabetes, vol. 48, Sep. 1999, pp. 1794-1800.
Opposition to an Invention Patent (and English translation thereof) from counterpart Costa Rica Application No. 11.263, published May 21, 2010.
Orjales et al. "New 2-Piperazinylbenzimidazole Derivatives as 5-HT-3 Antagonists. Synthesis and Pharmacological Evaluation," J. Med. Chem., vol. 40, 1997, pp. 586-593.
Parker et al, "Reductive Aromatization of Quinols: Synthesis of the C-Arylglycoside Nucleus of the Paulacandins and Chaetiacandin," Organic Letters, vol. 2, No. 4, 2000, pp. 497-499.
Patani et al., "Bioisosterism: A Rational Approach to Drug Design", Chem. Rev., American Chemical Society, vol. 96, 1996, pp. 3147-3176.
Peng et al., "Post-transcriptional Regulation of Na+/Glucose Cotransporter (SGTL1) Gene Expression in LLC-PK1 Cells.", Journal of Biological Chemistry, vol. 270, No. 35, Sep. 1995, pp. 20536-20542.
Polidori et al., "Frequently Used Insulin Sensitivity Measures May Be Inappropriate for Subjects Treated With SGLT2 Inhibitors," Jun. 2009, Poster presented at the American Diabetes Assoc. 69th Scientific Sessions, Jun. 5-9, 2009, New Orleans, LA.
Raynaud et al., "Revised Concept for the Estimation of Insulin Sensitivity From a Single Sample.", Diabetes Care, vol. 22, No. 6, Jun. 1999, pp. 1003-1004.
Rossetti et al., "Glucose Toxicity," Diabetes Care, vol. 13, Issue 6, 1990, pp. 610-630 (Abstract only provided).
Schmidt et al, "Synthese von Pyrazol-, Pyrazolo[3,4-d]pyrimidin- und 1H-1,2,4-Triazolgluconucleosiden aus Glucosehydrazonen," Liebigs Ann. Chem., 1981, pp. 2309-2317 (with English excerpt).
Silverman, "The Organic Chemistry of Drug Design and Drug Action," Academic Press, 1992, pp. 19-23.
Somei et al., "The First and Simple Total Synthesis of Cappariloside A1," Heterocycles, vol. 53, No. 7, 2000, pp. 1573-1578.
Srogl et al., "Sulfonium Salts. Participants par Excellence in Metal-Catalyzed Carbon-Carbon Bond-Forming Reactions", J. Am. Chem. Soc., vol. 119, No. 50, 1997, pp. 12376-12377.
Stoner et al, "Benzylation via Tandem Grignard Reaction—Iodotrimethylsilane (TMSI) Mediated Reduction," Tetrahedron, vol. 51, No. 41, 1995, pp. 11043-11062.
Stumvoll et al., "Use of the Oral Glucose Tolerance Test to Assess Insulin Release and Insulin Sensitivity", Diabetes Care, vol. 23, No. 3, Mar. 2000, pp. 295-301.
Tanaka et al. "Solid-Phase Synthesis of β-Mono-Substituted Ketones and an Application to the Synthesis of a Library of Phlorizin Derivatives", Synlett, No. 9, 2002, pp. 1427-1430.
The State Intellectual Property Office of P.R. China Office Action, Appl. No. 2004800220078, Dec. 26, 2008, pp. 1-6, Second Office Action, English translation only.
The State Intellectual Property Office of P.R. China Office Action, Appl. No. 2004800220078, Oct. 19, 2007, pp. 1-6, First Office Action, English translation only.
The State Intellectual Property Office of P.R. China the Decision of Rejection (PCT) Action, Appl. No. 2004800220078, Nov. 2009, pp. 1-7, English translation only.
The State Intellectual Property Office of P.R. China, Observations (1st), Appl. No. 2004800220078, May 2008, pp. 1-3, English translation only.
The State Intellectual Property Office of P.R. China, Observations (2nd), Appl. No. 2004800220078, May 2009, pp. 1-4, English translation only.
The State Intellectual Property Office of P.R. China, Record of Interview, Appl. No. 2004800220078, Sep. 25, 2009, pp. 1-7, English translation only.
The State Intellectual Property Office of P.R. China, Response to the Decision of Rejection (PCT), Appl. No. 2004800220078, Feb. 2010, pp. 1-27, English translation only.
Thornber, "Isosterism and Molecular Modification in Drug Design", Chemical Society Reviews, vol. 8, 1979, pp. 563-580.
Tilak, "Carcinogenesis by Thiophene Isosters of Polycyclic Hydrocarbons," Tetrahedron, vol. 9, 1960, pp. 76-95.
Tsujihara et al., "Na+-Glucose Cotransporter Inhibitors as Antidiabetic.1. Synthesis and Pharmacological Properties of 4'-Dehydroxyphlorizin Derivatives Based on a New Concept," Chem. Pharm. Bull., vol. 44, No. 6, 1996, pp. 1174-1180.
Tsujihara et al., Bio Clinica, vol. 13, No. 4, 1998, pp. 324-328 (with English language Abstract).
Turk et al., "Glucose/galactose malabsorption caused by a defect in the Na+/glucose cotransporter," Nature, vol. 350, Mar. 1991, pp. 354-356.
Ueta et al, "Anti-diabetic and Anti-obesity effects of Ta-7284, a Novel SGLT2 Inhibitor," Partial English translation, JDS Poster Presentation, 2009.
Ueta et al, "Long-term treatment with the Na+-glucose cotransporter inhibitor T-1095 causes sustained improvement in hyperglycemia and prevents diabetic neuropathy in Goto-Kakizaki Rats," Life Sciences, vol. 76, 2005, pp. 2655-2668.
Unger et al., "Hyperglycaemia as an inducer as well as a consequence of impaired islet cell function and insulin resistance: implications for the management of diabetes", Diabetologia, vol. 28, 1985, pp. 119-121.
Wallace et al., "Use and Abuse of HOMA Modeling", Diabetes Care, vol. 27, No. 6, Jun. 2004, pp. 1487-1495.
Wang et al, "Selective monolithiation of 2,5-dibromopyridine with butyllithium," Tetrahedron Letters, vol. 41, 2000, pp. 4335-4338.
Wareham et al., "Is There Really an epidemic of diabetes?", Diabetologia, vol. 48, 2005, pp. 1454-1455.
Washburn, "Evolution of sodium glucose co-transporter 2 inhibitors as anti-diabetic agents," Expert Opin. Ther. Patents, vol. 19, No. 11, 2009, pp. 1485-1499.
Wild et al., "Global Prevalence of Diabetes: Estimates for the year 2000 and projections for 2030," Diabetes Care, vol. 27, No. 5, May 2004, pp. 1047-1053.
Wolff, Burger's Medicinal Chemistry and Drug Discovery, 5th Edition, vol. 1: Principles and Practice, 1995, pp. 975-977.
Wright, "Renal Na+-glucose cotransporters," Am. J. Physiol. Renal Physiol., vol. 280, 2001, pp. F10-F18.
Yang et al., "Convergent C-Glycolipid Synthesis via the Ramberg-Bäcklund Reaction: Active Antiproliferative Glycolipids", Organic Letters, vol. 1, No. 13, 1999, pp. 2149-2151.
Yoshimura et al, "Discovery of Novel and Potent Retinoic Acid Receptor alpha-Agonists: Synthesis and Evaluation of Benzofuranyl-pyrrole and Benzothiophenyl-pyrrole Derivatives," J. Med. Chem., vol. 43, 2000, pp. 2929-2937.
Zamani, "Synthesis and Structure Determination of Some New N-Glycosides of 4,5-Disubstituted-1,2,4-triazole-3-thiones", Journal of the Chinese Chemical Society, vol. 49, 2002, pp. 1041-1044.
Zhou, "The Synthesis and Characterization of 1-Benzyl-3-N-(Beta-D-glucoside-1-yl)-5-fluorouracil", Hecheng Huaxue, vol. 9, No. 3, 2001, pp. 272-274.
Arakawa et al., "Improved Diabetic Syndrome in C57BL/KsJ-db/db Mice by Oral Administration of the Na+-glucose Cotransporter Inhibitor T-1095", British Journal of Pharmacology, vol. 132, No. 2, 2001, pp. 578-586.
Kahn et al., "Normalization of Blood Glucose in Diabetic Rats with Phlorizin Treatment Reverses Insulin-Resistant Glucose Transport in Adipose Cells Without Restoring Glucose Transporter Gene Expression", Journal of Clinical Investigation, vol. 87, Feb. 1991, pp. 561-570.
Rossetti et al., "Correctioin of Hyperglycemia with Phlorizin Normalizes Tissue Sensitivity to Insulin in Diabetic Rats", Journal of Clinical Investigation, vol. 79, May 1987, pp. 1510-1515.
Rossetti et al., "Effect of Chronic Hyperglycemia on in Vivo Insulin Secretion in Partially Pancreatectomized Rats", Journal of Clinical Investigation, vol. 80, Oct. 1987, pp. 1037-1044.

(56) References Cited

OTHER PUBLICATIONS

Tsujihara et al., "Na+-Glucose Cotransporter (SGLT) Inhibitors as Antidiabetic Agents. 4. Synthesis and Pharmacological Properties of 4'-Dehydroxyphlorizin Derivatives Substituted on the B Ring", Journal of Medicinal Chemistry, vol. 42, No. 26, 1999, pp. 5311-5324.

Ahren et al., "Twelve- and 52-Week Efficacy of the Dipeptidyl Peptidase IV inhibitor LAF237 in Metformin-Treated Patients with Type 2 Diabetes", Diabetes Care, vol. 27, No. 12 (2004) pp. 2874-2880.

Drucker et al., "Therapeutic potential of dipeptidyl peptidase IV inhibitors for the treatment of type 2 diabetes", Expert Opin. Investig. Drugs, vol. 12, No. 1 (2003) pp. 87-100.

Hussey et al., "A double-blind, randomized, repeat-dose study to assess the safety, tolerability, pharmacokinetics and pharmacodynamics of three-times-daily dosing of sergliflozin, a novel inhibitor . . . ", American Diabetes Association 2007 Meeting Abstract, No. 0491-P.

Shaffer, "Incretin mimetics vie for slice of type 2 diabetes market", Nature Biotechnolody, vol. 25, No. 3 (2007) p. 263.

* cited by examiner

COMBINATION THERAPY COMPRISING SGLT INHIBITORS AND DPP4 INHIBITORS

CROSS REFERENCE TO RELATED APPLICATIONS

This application is the National Phase of PCT/JP2009/051023 filed on Jan. 16, 2009 which claims priority under 35 U.S.C 119(e) of U.S. Provisional Application No. 61/021,777 filed on Jan. 17, 2008. The entire contents of the above application are hereby incorporated by reference into the present application.

TECHNICAL FIELD

The present invention relates to compositions and methods for increasing plasma active GLP-1 level in a mammal. The present invention further relates to compositions and methods for ameliorating conditions by increasing plasma active GLP-1 level.

BACKGROUND ART

Glucagon-like peptide-1 (GLP-1) is an incretin hormone that is released from L-cells in lower small intestine after food intake. GLP-1 has been shown to stimulate glucose-dependent insulin secretion from pancreatic β-cells and increase pancreatic β-cell mass. GLP-1 has also been shown to reduce the rate of gastric emptying and promote satiety. However, GLP-1 is rapidly cleaved by dipeptidyl peptidase 4 (DPP4) leading to inactivation of its biological activity. Therefore, DPP4 inhibitors are considered to be useful as anti-diabetics or anti-obesity agents.

Sodium-glucose co-transporters (SGLTs), primarily found in the intestine and the kidney, are a family of proteins involved in glucose absorption. Plasma glucose is filtered in the glomerulus and is reabsorbed by SGLTs in the proximal tubules. Therefore, inhibition of SGLTs cause excretion of blood glucose into urine and leads to reduction of plasma glucose level. In fact, it is confirmed that by continuous subcutaneous administration of an SGLT inhibitor, phlorizin, to diabetic animal models, the blood glucose level thereof can be normalized, and that by keeping the blood glucose level normal for a long time, the insulin secretion and insulin resistance can be improved [cf., Journal of Clinical Investigation, vol. 79, p. 1510 (1987); ibid., vol. 80, p. 1037 (1987); ibid., vol. 87, p. 561 (1991)].

In addition, by treating diabetic animal models with an SGLT inhibitor for a long time, insulin secretion response and insulin sensitivity of the animal models are improved without incurring any adverse affects on the kidney or imbalance in blood levels of electrolytes, and as a result, the onset and progress of diabetic nephropathy and diabetic neuropathy are prevented [cf., Journal of Medicinal Chemistry, vol. 42, p. 5311 (1999); British Journal of Pharmacology, vol. 132, p. 578 (2001)].

In view of the above, SGLT inhibitors are expected to improve insulin secretion and insulin resistance by decreasing the blood glucose level in diabetic patients and to prevent the onset and progress of diabetes mellitus and diabetic complications.

DISCLOSURE OF INVENTION

The inventors of the present invention have found that administration of an SGLT inhibitor in combination with a DPP4 inhibitor can provide an unexpected synergistic effect in increasing plasma active GLP-1 level in a patient over that provided by administration of the SGLT inhibitor or the DPP4 inhibitor alone.

Accordingly, in one aspect, the present invention relates to combination of an SGLT inhibitor and a DPP4 inhibitor such that the combination provides an effect in increasing plasma active GLP-1 level in a patient over that provided by the SGLT inhibitor or the DPP4 inhibitor alone.

In another aspect, the present invention relates to use of combination of an SGLT inhibitor and DPP4 inhibitor for preventing or treating some sort of disease which is associated with plasma active GLP-1 level.

In another aspect, the present invention relates to a pharmaceutical composition comprising an SGLT inhibitor and a DPP4 inhibitor for use in prevention or treatment of some sort of disease which is associated with plasma active GLP-1 level.

In another aspect, the present invention relates to a method of preventing or treating some sort of disease which is associated with plasma active GLP-1 level comprising administering to a patient in need thereof a therapeutically effective amount of a pharmaceutical composition comprising an SGLT inhibitor and a DPP4 inhibitor.

In another aspect, the present invention relates to use of an SGLT inhibitor and a DPP4 inhibitor for the manufacture of a medicament for the prevention or treatment of some sort of disease which is associated with plasma active GLP-1 level.

In another aspect, the present invention relates to a product containing an SGLT inhibitor and a DPP4 inhibitor as a combined preparation for simultaneous, separate or sequential administration for preventing or treating a disease associated with plasma active GLP-1 level.

DETAILED DESCRIPTION OF THE INVENTION

As used herein, the term "diabetes" encompasses both insulin-dependent diabetes mellitus (also known as Type 1 diabetes) and non-insulin-dependent diabetes mellitus (also known as Type 2 diabetes).

The term "disease which is associated with plasma active GLP-1 level" includes diabetes, a condition related to diabetes, obesity, myocardial infarction, stroke, learning impairment, memory impairment, and a neurodegenerative disorder.

The term "condition related to diabetes" includes hyperglycemia, impaired glucose tolerance, impaired fasting glucose, insulin resistance, pancreatic beta-cell insufficiency, enteroendocrine cell insufficiency, glucosuria, metabolic acidosis, cataracts, diabetic nephropathy, diabetic neuropathy, diabetic retinopathy, diabetic coronary artery disease, diabetic cerebrovascular disease, diabetic peripheral vascular disease, metabolic syndrome, hyperlipidemia, atherosclerosis, stroke, hypertension, and obesity.

The term "halogen" or "halo" refers to chlorine, bromine, fluorine and iodine, and chlorine and fluorine are preferable.

The term "alkyl" means a straight or branched saturated monovalent hydrocarbon chain having 1 to 12 carbon atoms, unless otherwise noted. The straight chain or branched chain alkyl group having 1 to 6 carbon atoms is preferable, and the straight chain or branched chain alkyl group having 1 to 4 carbon atoms is more preferable. Examples of alkyl include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, and various branched chain isomers thereof. Further, the alkyl group may optionally and independently be substituted by 1 to 4 substituents as listed below, if necessary.

The term "alkylene" means a straight or branched divalent saturated hydrocarbon chain having 1 to 12 carbon atoms, unless otherwise noted. The straight chain or branched chain alkylene group having 1 to 6 carbon atoms is preferable, and the straight chain or branched chain alkylene group having 1 to 4 carbon atoms is more preferable. Examples of alkylene include methylene, ethylene, propylene, and trimethylene. If necessary, the alkylene group, may optionally be substituted similarly to "alkyl" as mentioned above.

When alkylene attaches at two different carbon atoms of the benzene ring, they form an annelated five, six or seven membered carbocycle together with the carbon atoms to which they are attached, and may optionally be substituted by one or more substituents defined below.

The term "alkenyl" means a straight or branched monovalent hydrocarbon chain having 2 to 12 carbon atoms and having at least one double bond, unless otherwise noted. Preferable "alkenyl" is a straight chain or branched chain alkenyl group having 2 to 6 carbon atoms, and the straight chain or branched chain alkenyl group having 2 to 4 carbon atoms is more preferable. Examples of alkenyl include vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, and 4,8,12-tetradecatrienyl. The alkenyl group may optionally and independently be substituted by 1 to 4 substituents as mentioned below, if necessary.

The term "alkenylene" means a straight or branched divalent hydrocarbon chain having 2 to 12 carbon atoms and having at least one double bond, unless otherwise noted. The straight chain or branched chain alkenylene group having 2 to 6 carbon atoms is preferable, and the straight chain or branched chain alkenylene group having 2 to 4 carbon atoms is more preferable. Examples of alkenylene include vinylene, propenylene, butadienylene. If necessary, the alkenylene group may optionally be substituted by 1 to 4 substituents as mentioned below, if necessary.

When an alkenylene group attaches at two different carbon atoms of a benzene ring, they form an annelated five, six or seven membered carbocycle (e.g., a fused benzene ring) together with the carbon atoms to which they are attached, and may optionally be substituted by one or more substituents defined below.

The term "alkynyl" means a straight or branched monovalent hydrocarbon chain having at least one triple bond, unless otherwise noted. The preferable alkynyl group is a straight chain or branched chain alkynyl group having 2 to 6 carbon atoms, and the straight chain or branched chain alkynyl group having 2 to 4 carbon atoms is more preferable. Examples of "alkynyl" include 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, and 4-dodecynyl. The alkynyl group may optionally and independently be substituted by 1 to 4 substituents as mentioned below, if necessary.

The term "cycloalkyl" means a monocyclic or bicyclic monovalent saturated hydrocarbon ring having 3 to 12 carbon atoms, unless otherwise noted, and the monocyclic saturated hydrocarbon group having 3 to 7 carbon atoms is more preferable. Examples of cycloalkyl include monocyclic and bicyclic alkyl such as cyclopropyl, cyclobutyl, cyclopentyl, cyclohexyl, cycloheptyl, cyclooctyl, and cyclodecyl. These groups may optionally and independently be substituted by 1 to 4 substituents as mentioned below, if necessary. The cycloalkyl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the condensed unsaturated hydrocarbon ring may be optionally and independently be substituted by 1 to 4 substituents as mentioned below.

The term "cycloalkylidene" means a monocyclic or bicyclic divalent saturated hydrocarbon ring having 3 to 12 carbon atoms, unless otherwise noted, and the monocyclic saturated hydrocarbon group having 3 to 6 carbon atoms is preferable. Examples of "cycloalkylidene" include monocyclic and bicyclic alkylidene such as cyclopropylidene, cyclobutylidene, cyclopentylidine, and cyclohexylidene. These groups may optionally and independently be substituted by 1 to 4 substituents as mentioned below, if necessary. Besides, the cycloalkylidene group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the unsaturated hydrocarbon ring may be optionally and independently be substituted by 1 to 4 substituents as mentioned below.

The term "cycloalkenyl" means a monocyclic or bicyclic monovalent unsaturated hydrocarbon ring having 4 to 12 carbon atoms and having at least one double bond, unless otherwise noted. The preferable cycloalkenyl group is a monocyclic unsaturated hydrocarbon group having 4 to 7 carbon atoms. Examples of "cycloalkenyl" include monocyclic alkenyl such as cyclopentenyl, cyclopentadienyl, and cyclohexenyl. These groups may optionally and independently be substituted by 1 to 4 substituents as mentioned below, if necessary. Besides, the cycloalkenyl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the unsaturated hydrocarbon ring may be optionally and independently be substituted by 1 to 4 substituents as mentioned below.

The term "cycloalkynyl" means a monocyclic or bicyclic unsaturated hydrocarbon ring having 6 to 12 carbon atoms, and having at least one triple bond, unless otherwise noted. The preferable cycloalkynyl group is a monocyclic unsaturated hydrocarbon group having 6 to 8 carbon atoms. Examples of "cycloalkynyl" include monocyclic alkynyl such as cyclooctynyl, and cyclodecynyl. These groups may optionally be substituted by 1 to 4 substituents as mentioned below, if necessary. Besides, the cycloalkynyl group may optionally and independently be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring or the unsaturated hydrocarbon ring may be optionally and independently be substituted by 1 to 4 substituents as mentioned below.

The term "aryl" or "Aryl" means a monocyclic or bicyclic monovalent aromatic hydrocarbon group having 6 to 10 carbon atoms, unless otherwise noted. Examples of aryl include phenyl and naphthyl (including 1-naphthyl group and 2-naphthyl group). These groups may optionally and independently be substituted by 1 to 4 substituents as mentioned below, if necessary. Besides, the aryl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring or the unsaturated hydrocarbon ring may be optionally and independently be substituted by 1 to 4 substituents as mentioned below.

The term "unsaturated monocyclic heterocyclic ring" means an unsaturated hydrocarbon ring containing 1-4 heteroatoms independently selected from a nitrogen atom, an oxygen atom and a sulfur atom, and the preferable one is a 4- to 7-membered saturated or unsaturated hydrocarbon ring containing 1-4 heteroatoms independently selected from a nitrogen atom, an oxygen atom and a sulfur atom, unless otherwise noted. Examples of the unsaturated monocyclic heterocyclic ring are pyridine, pyrimidine, pyrazine, furan, thiophene, pyrrole, imidazole, pyrazole, oxazole, isoxazole, 4,5-dihydrooxazolyl, thiazole, isothiazole, thiadiazole, triazole, and tetrazole. Among them, pyridine, pyrimidine, pyrazine, furan, thiophene, pyrrole, imidazole, oxazole, and thiazole can be preferably used. The unsaturated monocyclic heterocyclic ring may optionally and independently be substituted by 1-4 substituents as mentioned below, if necessary.

The term "unsaturated fused heterobicyclic ring" means a hydrocarbon ring comprised of a saturated or a unsaturated hydrocarbon ring condensed with the above mentioned unsaturated monocyclic heterocyclic ring where said saturated hydrocarbon ring and said unsaturated hydrocarbon ring may optionally contain an oxygen atom, a nitrogen atom, a sulfur atom, SO, or $SO_2$ within the ring, if necessary. Examples of the unsaturated fused heterobicyclic ring include benzothiophene, indole, tetrahydrobenzothiophene, benzofuran, isoquinoline, thienothiophene, thienopyridine, quinoline, indoline, isoindoline, benzothiazole, benzoxazole, indazole, and dihydroisoquinoline. Further, the "heterocyclic ring" also includes possible N- or S-oxides thereof.

The term "heterocyclyl" means a monovalent group of the above-mentioned unsaturated monocyclic heterocyclic ring or unsaturated fused heterobicyclic ring and a monovalent group of the saturated version of the above-mentioned unsaturated monocyclic heterocyclic or unsaturated fused heterobicyclic ring. If necessary, the heterocyclyl may optionally and independently be substituted by 1 to 4 substituents as mentioned below.

The term "alkanoyl" includes formyl and alkyl linked to carbonyl, unless otherwise noted.

The term "alkoxy" includes alkyl linked to oxygen, unless otherwise noted.

Examples of the substituent for the above each group includes halogen (e.g., fluorine, chlorine, bromine, and iodine), nitro, cyano, oxo, hydroxy, mercapto, carboxyl, sulfo, alkyl, alkenyl, alkynyl, cycloalkyl, cycloalkylidenemethyl, cycloalkenyl, cycloalkynyl, aryl, heterocyclyl, alkoxy, alkenyloxy, alkynyloxy, cycloalkyloxy, cycloalkenyloxy, cycloalkynyloxy, aryloxy, heterocyclyloxy, alkanoyl, alkenylcarbonyl, alkynylcarbonyl, cycloalkylcarbonyl, cycloalkenylcarbonyl, cycloalkynylcarbonyl, arylcarbonyl, heterocyclylcarbonyl, alkoxycarbonyl, alkenyloxycarbonyl, alkynyloxycarbonyl, cycloalkyloxycarbonyl, cycloalkenyloxycarbonyl, cycloalkynyloxycarbonyl, aryloxycarbonyl, heterocyclyloxycarbonyl, alkanoyloxy, alkenylcarbonyloxy, alkynylcarbonyloxy, cycloalkylcarbonyloxy, cycloalkenylcarbonyloxy, cycloalkynylcarbonyloxy, arylcarbonyloxy, heterocyclylcarbonyloxy, alkylthio, alkenylthio, alkynylthio, cycloalkylthio, cycloalkenylthio, cycloalkynylthio, arylthio, heterocyclylthio, amino, mono- or di-alkylamino, mono- or di-alkanoylamino, mono- or di-alkoxycarbonylamino, mono- or di-arylcarbonylamino, alkyl-sulfinylamino, alkylsulfonylamino, arylsulfinylamino, arylsulfonylamino, carbamoyl, mono- or di-alkylcarbamoyl, mono- or di-arylcarbamoyl, alkylsulfinyl, alkenylsulfinyl, alkynylsulfinyl, cycloalkylsulfinyl, cycloalkenylsulfinyl, cycloalkynylsulfinyl, arylsulfinyl, heterocyclylsulfinyl, alkylsulfonyl, alkenylsulfonyl, alkynylsulfonyl, cycloalkylsulfonyl, cycloalkenylsulfonyl, cycloalkynylsulfonyl, arylsulfonyl, and heterocyclylsulfonyl. Each group mentioned above may optionally be substituted by these substituents.

Further, the terms such as haloalkyl, halo-lower alkyl, haloalkoxy, halo-lower alkoxy, halophenyl, and haloheterocyclyl mean alkyl, lower alkyl, alkoxy, lower alkoxy, phenyl group or heterocyclyl (hereinafter, referred to as "alkyl, etc.") being substituted by one or more halogen, respectively. Preferable examples include alkyl, etc., being substituted by 1 to 7 halogen, and more preferable examples include alkyl, etc., being substituted by 1 to 5 halogen. Similarly, the terms such as hydroxy-alkyl, hydroxy-lower alkyl, hydroxyalkoxy, hydroxy-lower alkoxy and hydroxyphenyl mean alkyl, etc., being substituted by one or more hydroxy groups. Preferable examples include alkyl, etc., being substituted by 1 to 4 hydroxy groups, and more preferable examples include alkyl, etc., being substituted by 1 to 2 hydroxy groups. Further, the terms such as alkoxyalkyl, lower alkoxyalkyl, alkoxy-lower alkyl, lower alkoxy-lower alkyl, alkoxyalkoxy, lower alkoxyalkoxy, alkoxy-lower alkoxy, lower alkoxy-lower alkoxy, alkoxyphenyl, and lower alkoxyphenyl means alkyl, etc., being substituted by one or more alkoxy groups. Preferable examples include alkyl, etc., being substituted by 1 to 4 alkoxy groups, and more preferable examples include alkyl, etc., being substituted by 1 to 2 alkoxy groups.

The terms "arylakyl" and "arylalkoxy" as used alone or as part of another group refer to alkyl and alkoxy groups as described above having an aryl substituent.

The term "lower" used in the definitions for the formulae in the present specification means a straight or branched carbon chain having 1 to 6 carbon atoms, unless defined otherwise. More preferably, it means a straight or branched carbon chain having 1 to 4 carbon atoms.

The term "prodrug" means an ester or carbonate, which can be formed by reacting one or more hydroxy groups of the compound used in the combination therapy of the present invention with an acylating agent by a conventional method. Examples of the ester include acetate, pivalate, methyl-carbonate, and benzoate. Further, the term "prodrug" also means an ester or amide, which can be similarly formed by reacting one or more hydroxy groups of the compound used in the combination therapy of the present invention with an α-amino acid or a β-amino acid using a condensing agent by a conventional method.

Examples of a pharmaceutically acceptable salt of SGLT inhibitors or DPP4 inhibitors include a salt with an alkali metal (e.g., lithium, sodium, and potassium); a salt with an alkaline earth metal (e.g., calcium, and magnesium); a salt with zinc or aluminum; a salt with an organic base (e.g., ammonia, choline, diethanolamine, lysine, ethylenediamine, t-butylamine, t-octylamine, tris(hydroxymethyl)aminomethane, N-methyl-glucosamine, triethanolamine and dehydroabietylamine); a salt with an inorganic acid (e.g., hydrochloric acid, hydrobromic acid, hydroiodic acid, sulfuric acid, nitric acid, and phosphoric acid); a salt with an organic acid (e.g., formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, and benzenesulfonic acid); and a salt with an acidic amino acid (e.g., aspartic acid, and glutamic acid).

Additionally, the term "pharmaceutically acceptable salt" used herein encompass solvates, and hydrates thereof.

It is evident that some compounds used in the compositions or combination of the present invention may have one or more asymmetric carbon atoms in their structure. It is intended that the present invention includes within its scope the stereochemically pure isomeric forms of the compounds as well as their racemates. Stereochemically pure isomeric forms may be obtained by the methods well known to those skilled in the art. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereospecific reactions.

SGLT inhibitors are well known to those skilled in the art, and examples of the SGLT inhibitors are described in many publications or patent literatures.

In an embodiment of the present invention, SGLT inhibitors are the C-aryl glucosides disclosed in WO 01/27128 pamphlet, which are represented by Formula (1):

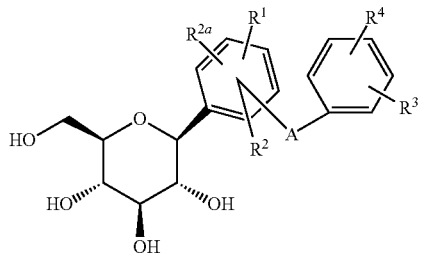

(1)

wherein:
$R^1$, $R^2$ and $R^{2a}$ are independently hydrogen, OH, $OR^5$, alkyl, $CF_3$, $OCHF_2$, $OCF_3$, $SR^{5i}$ or halogen, or two of $R^1$, $R^2$ and $R^{2a}$ together with the carbons to which they are attached can form an annelated five, six or seven membered carbocycle or heterocycle which may contain 1 to 4 heteroatoms in the ring which are N, O, S, SO, and/or $SO_2$;
$R^3$ and $R^4$ are independently hydrogen, OH, $OR^{5a}$, OAryl, $OCH_2$Aryl, alkyl, cycloalkyl, $CF_3$, —$OCHF_2$, —$OCF_3$, halogen, —CN, —$CO_2R^{5b}$, —$CO_2H$, —$COR^{6b}$, —CH(OH)$R^{6c}$, —CH($OR^{5h}$)$R^{6d}$, —$CONR^6R^{6a}$, —$NHCOR^{5c}$, —$NHSO_2R^{5d}$, —$NHSO_2$Aryl, Aryl, —$SR^{5e}$, —$SOR^{5f}$, —$SO_2R^{5g}$, —$SO_2$Aryl, or a five, six or seven membered heterocycle which may contain 1 to 4 heteroatoms in the ring which are N, O, S, SO, and/or $SO_2$, or $R^3$ and $R^4$ together with the carbons to which they are attached form an annelated five, six or seven membered carbocycle or heterocycle which may contain 1 to 4 heteroatoms in the ring which are N, O, S, SO, and/or $SO_2$;
$R^5$, $R^{5a}$, $R^{5b}$, $R^{5c}$, $R^{5d}$, $R^{5e}$, $R^{5f}$, $R^{5g}$, $R^{5h}$ and $R^{5i}$ are independently alkyl;
$R^6$, $R^{6a}$, $R^{6b}$, $R^{6c}$ and $R^{6d}$ are independently hydrogen, alkyl, aryl, alkylaryl or cycloalkyl, or $R^6$ and $R^{6a}$ together with the nitrogen to which they are attached form an annelated five, six or seven membered heterocycle which may contain 1 to 4 heteroatoms in the ring which are N, O, S, SO, and/or $SO_2$;

A is O, S, NH, or $(CH_2)_n$ where n is 0-3, and a pharmaceutically acceptable salt thereof, all stereoisomers thereof, and all prodrug esters thereof.

In a preferable embodiment of the present invention, the SGLT inhibitor is Dapagliflozin represented by Formula (2):

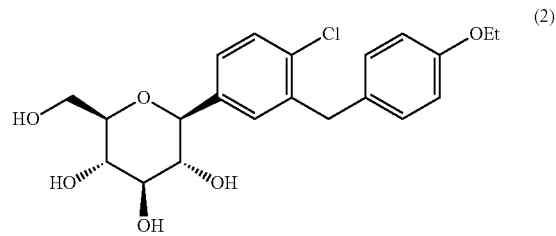 [SMILES: CCOc1ccc(Cc2cc([C@@H]3O[C@H](CO)[C@@H](O)[C@H](O)[C@H]3O)ccc2Cl)cc1]

(2)

a pharmaceutically acceptable salt thereof, a stereoisomer thereof, or a prodrug ester thereof.

In another preferable embodiment of the present invention, the SGLT inhibitor is the C-aryl glucoside compound disclosed in WO 2006/034489 pamphlet, which is represented by Formula (3):

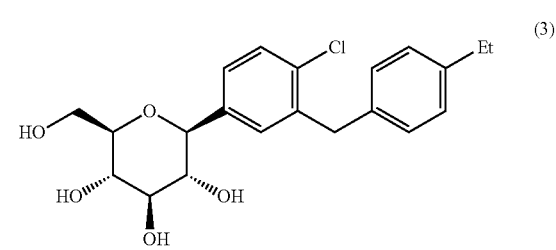 [SMILES: CCc1ccc(Cc2cc([C@@H]3O[C@H](CO)[C@@H](O)[C@H](O)[C@H]3O)ccc2Cl)cc1]

(3)

a pharmaceutically acceptable salt thereof, a stereoisomer thereof, or a prodrug ester thereof.

In an embodiment of the present invention, the SGLT inhibitors are O-aryl glucoside compounds disclosed in WO 01/74834 pamphlet, which are represented by Formula (4):

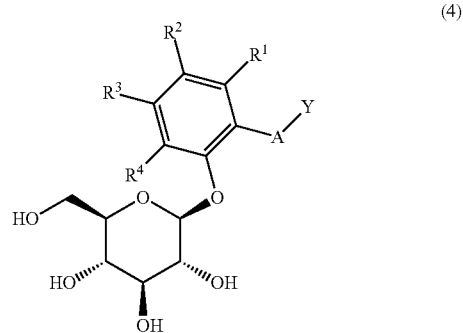

(4)

wherein Y is

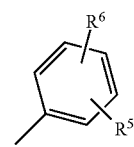

or heteroaryl;
$R^1$, $R^2$, $R^3$, and $R^4$ are the same or different and are independently selected from hydrogen, OH, $OR^7$, lower alkyl, or halogen, or two of $R^1$, $R^2$, $R^3$, and $R^4$ together with the carbons to which they are attached can form an annelated five, six or seven membered carbocycle or heterocycle which may contain 1 to 4 heteroatoms in the ring which are N, O, S, SO, and/or $SO_2$;

$R^5$ and $R^6$ are the same or different and are independently selected from hydrogen, OH, $OR^{7a}$, —OAryl, —OCH$_2$Aryl, lower alkyl, cycloalkyl, Aryl, arylalkyl, $CF_3$, arylalkenyl, —OCHF$_2$, —OCF$_3$, halogen, —CN, —CO$_2$R$^{7b}$, —CO$_2$H, COR$^{8f}$, CHOHR$^{8g}$, CH(OR$^{7h}$)R$^{8h}$, —CONR$^8$R$^{8a}$, —NHCOR$^{7c}$, —NHSO$_2$R$^{7d}$, —NHSO$_2$Aryl, —SR$^{7e}$, —SOR$^{7f}$, —SO$_2$R$^{7g}$, —SO$_2$Aryl, —OCH$_2$CO$_2$R$^{7i}$, —OCH$_2$CO$_2$H, —OCH$_2$CONR$^{8b}$R$^{8c}$, —OCH$_2$CH$_2$NR$^{8d}$R$^{8e}$, or a five, six or seven membered heterocycle which may contain 1 to 4 heteroatoms in the ring which are N, O, S, SO, and/or SO$_2$, or $R^5$ and $R^6$ together with the carbons to which they are attached form an annelated five, six or seven membered carbocycle or heterocycle which may contain 1 to 4 heteroatoms in the ring which are N, O, S, SO, and/or SO$_2$;

$R^7$, $R^{7a}$, $R^{7b}$, $R^{7c}$, $R^{7d}$, $R^{7e}$, $R^{7f}$, $R^{7g}$, $R^{7h}$, and $R^{7i}$ are independently lower alkyl;

$R^8$, $R^{8a}$, $R^{8b}$, $R^{8c}$, $R^{8d}$, $R^{8e}$, $R^{8f}$, $R^{8g}$, and $R^{8h}$ are the same or different and are independently selected from hydrogen, alkyl, aryl, arylalkyl, cycloalkyl, or together with the nitrogen to which they are attached form an annelated five, six or seven membered heterocycle which may contain 1 to 4 heteroatoms in the ring which are N, O, S, SO, and/or SO$_2$;

A is O(CH$_2$)$_m$, S, NH(CH$_2$)$_m$, or (CH$_2$)$_n$ where n is 0-3 and m is 0-2, and a pharmaceutically acceptable salt thereof, all stereoisomers thereof, and all prodrug esters thereof.

In an embodiment of the present invention, the SGLT inhibitors are the glucopyranosyloxybenzyl-benzene derivatives disclosed in WO 02/028872 pamphlet, which are represented by Formula (5):

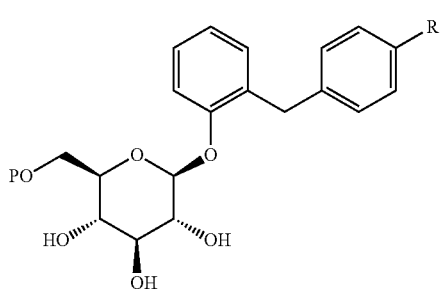

wherein P represents a group forming a prodrug; and R represents lower alkyl, lower alkoxy, lower alkylthio, lower alkoxy-substituted lower alkyl, lower alkoxy-substituted lower alkoxy or lower alkoxy-substituted lower alkylthio.

In an embodiment of the present invention, the SGLT inhibitors are the glucopyranosyloxybenzyl-benzene derivatives disclosed in WO 01/68660 pamphlet, which are represented by Formula (6):

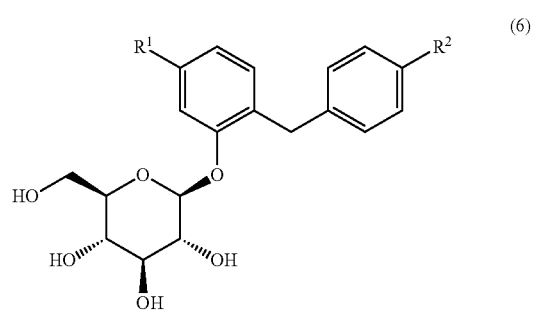

wherein $R^1$ represents hydrogen or hydroxy(lower alkyl); and $R^2$ represents lower alkyl, lower alkoxy, lower alkylthio, hydroxy(lower alkyl), hydroxy(lower alkoxy), hydroxy (lower alkylthio), lower alkoxy-substituted (lower alkyl), lower alkoxy-substituted (lower alkoxy) or lower alkoxy-substituted (lower alkylthio), or a pharmaceutically acceptable salt thereof.

In a preferable embodiment of the present invention, the SGLT inhibitor is Sergliflozin represented by Formula (7):

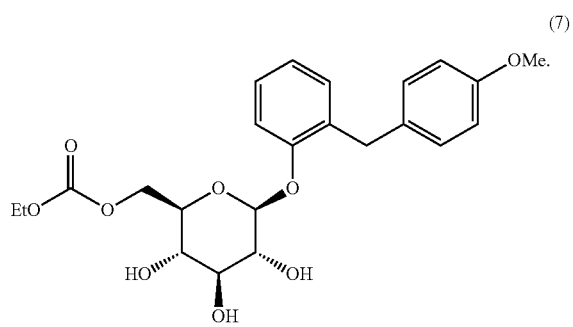 [SMILES: CCOC(=O)OC[C@H]1O[C@@H](Oc2ccccc2Cc2ccc(OC)cc2)[C@H](O)[C@@H](O)[C@@H]1O]

In another preferable embodiment of the present invention, the SGLT inhibitor is Sergliflozin-A represented by Formula (8):

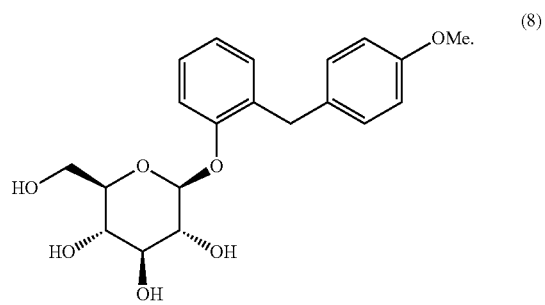 [SMILES: COc1ccc(Cc2ccccc2O[C@@H]2O[C@H](CO)[C@@H](O)[C@H](O)[C@H]2O)cc1]

In an embodiment of the present invention, the SGLT inhibitors are the glucopyranosyloxypyrazole derivatives disclosed in WO 02/053573 pamphlet, which are represented by Formula (9):

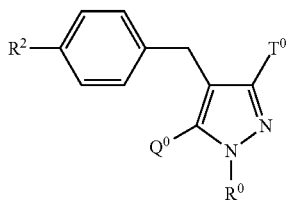

(9)

wherein R represents hydrogen, lower alkyl or a group forming a prodrug; one of Q and T represents a group represented by the formula:

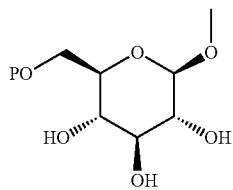

(wherein P represents hydrogen or a group forming a prodrug), while the other represents lower alkyl or halo(lower alkyl);

$R^2$ represents hydrogen, lower alkyl, lower alkoxy, lower alkylthio, halo(lower alkyl) or halogen;

with the proviso that P does not represent hydrogen when R represents hydrogen or lower alkyl, or a pharmaceutically acceptable salt thereof.

In a preferable embodiment of the present invention, the SGLT inhibitor is Remogliflozin represented by Formula (9a):

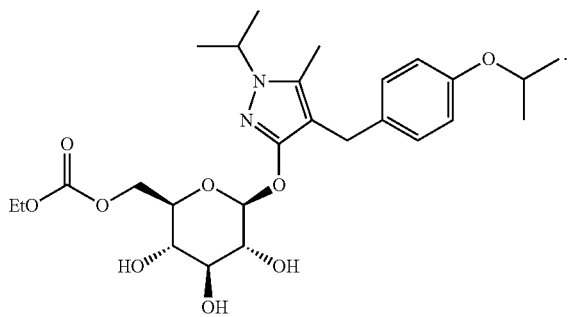

(9a)

In an embodiment of the present invention, the SGLT inhibitors are the compounds disclosed in WO 2005/085265 pamphlet, which are represented by Formula (10):

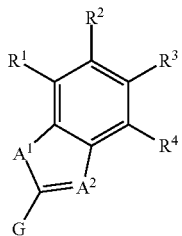

(10)

wherein one of $R^1$ and $R^4$ represents a group of the formula:

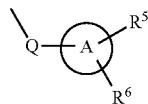

in which $R^5$ and $R^6$ independently represent hydrogen, hydroxy, halogen, $C_{1-6}$ alkyl, $C_{2-6}$ alkenyl, $C_2$-alkynyl, $C_{1-6}$ alkoxy, $C_{2-6}$ alkenyloxy, $C_{1-6}$ alkylthio, $C_{2-6}$alkenylthio, halo($C_{1-6}$ alkyl), halo($C_{1-6}$ alkoxy), halo($C_{1-6}$ alkylthio), hydroxy ($C_{1-6}$ alkyl), hydroxy($C_{2-6}$alkenyl), hydroxy($C_{1-6}$ alkoxy), hydroxy($C_{1-6}$ alkylthio), carboxy, carboxy($C_{1-6}$ alkyl), carboxy($C_{2-6}$alkenyl), carboxy($C_{1-6}$ alkoxy), carboxy($C_{1-6}$ alkylthio), $C_{2-7}$ alkoxycarbonyl, $C_{2-7}$alkoxycarbonyl($C_{1-6}$ alkyl), $C_{2-7}$alkoxycarbonyl($C_{2-6}$ alkenyl), $C_{2-7}$alkoxycarbonyl($C_{1-6}$ alkoxy), $C_{2-7}$ alkoxycarbonyl($C_{1-6}$ alkylthio), $C_{1-6}$ alkylsulfinyl, $C_{1-6}$ alkylsulfonyl, —U—V—W—N($R^7$)—Z, or any of the following substituents (i) to (xxviii) which may have 1 to 3 substituents selected from the following substituent group α on the ring;

(i) $C_{6-10}$ aryl, (ii) $C_{6-10}$ aryl-O—, (iii) $C_{6-10}$ aryl-S—, (iv) $C_{6-10}$ aryl($C_{1-6}$ alkyl), (v) $C_{6-10}$ aryl($C_{1-6}$ alkoxy), (vi) $C_{6-10}$ aryl($C_{1-6}$ alkylthio), (vii) heteroaryl, (viii) heteroaryl-O—, (ix) heteroaryl-S—, (x) heteroaryl($C_{1-6}$ alkyl), (xi) heteroaryl($C_{1-6}$ alkoxy), (xii) heteroaryl($C_{1-6}$ alkylthio), (xiii) $C_{3-7}$ cycloalkyl, (xiv) $C_{3-7}$ cycloalkyl-O—, (xv) $C_{3-7}$ cycloalkyl-S—, (xvi) $C_{3-7}$ cycloalkyl($C_{1-6}$ alkyl), (xvii) $C_{3-7}$ cycloalkyl($C_{1-6}$ alkoxy), (xviii) $C_{3-7}$ cycloalkyl($C_{1-6}$ alkylthio), (xix) heterocycloalkyl, (xx) heterocycloalkyl-O—, (xxi) heterocycloalkyl-S—, (xxii) heterocycloalkyl($C_{1-6}$ alkyl), (xxiii) heterocycloalkyl($C_{1-6}$ alkoxy), (xxiv) heterocycloalkyl($C_{1-6}$ alkylthio), (xxv) aromatic cyclic amino, (xxvi) aromatic cyclic amino($C_{1-6}$ alkyl), (xxvii) aromatic cyclic amino($C_{1-6}$ alkoxy), or (xxviii) aromatic cyclic amino($C_{1-6}$ alkylthio), J represents $C_{1-6}$alkylene which may have hydroxy, or $C_{2-6}$ alkenylene;

U represents —O—, —S— or a single bond and with the proviso that at least one of V and W is not a single bond when U is —O— or —S—;

V represents $C_{1-6}$ alkylene which may have hydroxy, $C_{2-6}$ alkenylene or a single bond;

W represents —CO—, —$SO_2$—, —C(=NH)— or a single bond;

Z independently represents hydrogen, $C_{2-7}$ alkoxycarbonyl, $C_{6-10}$ aryl($C_{2-7}$alkoxycarbonyl), formyl, —$R^A$, —$COR^B$, —$SO_2R^B$, —CON($R^C$)$R^D$, —CSN($R^C$)$R^D$, —$SO_2NHR^A$ or —C(=$NR^E$)N($R^F$)$R^G$;

$R^7$, $R^A$, $R^C$ and $R^D$ independently represent hydrogen, $C_{1-6}$ alkyl which may have 1 to 5 substituents selected from the following substituent group β, or any of the following substituents (xxix) to (xxxii) which may have 1 to 3 substituents selected from the following substituent group α;

(xxix) $C_{6-10}$ aryl, (xxx) heteroaryl, (xxxi) $C_{3-7}$ cycloalkyl or (xxxii) heterocycloalkyl or Z and $R^7$ bind together with the neighboring nitrogen to form aliphatic cyclic amino which may have 1 to 3 substituents selected from the following substituent group α;

or $R^C$ and $R^D$ bind together with the neighboring nitrogen to form aliphatic cyclic amino which may have 1 to 3 substituents selected from the following substituent group α;

$R^B$ represents $C_{2-7}$alkoxycarbonyl, $C_{1-6}$ alkylsulfonylamino, $C_{6-10}$ arylsulfonylamino, $C_{1-6}$ alkyl which may have 1 to 5 substituents selected from the following substituent group β or any of the following substituents (xxxiii) to (xxxvi) which may have 1 to 3 substituents selected from the following substituent group α;

(xxxiii) $C_{6-10}$ aryl, (xxxiv) heteroaryl, (xxxv) $C_{3-7}$ cycloalkyl or (xxxvi) heterocycloalkyl, $R^E$, $R^F$ and $R^G$ independently represent hydrogen, cyano, carbamoyl, $C_{2-7}$ acyl, $C_{2-7}$ alkoxycarbonyl, $C_{6-10}$ aryl($C_{2-7}$ alkoxycarbonyl), nitro, $C_{1-6}$ alkylsulfonyl, sulfamide, carbamimidoyl or $C_{1-6}$ alkyl which may have 1 to 5 substituents selected from the following substituent group β;

or $R^E$ and $R^F$ bind together to form ethylene;

or $R^F$ and $R^G$ bind together with the neighboring nitrogen to form aliphatic cyclic amino which may have any substituent selected from the following substituent group α;

Q represents —$C_{1-6}$ alkylene-, —$C_{2-6}$ alkenylene-, —$C_{2-6}$ alkynylene-, —$C_{1-6}$ alkylene-O—, —$C_{1-6}$ alkylene-S—, —O—$C_{1-6}$ alkylene-, —S—$C_{1-6}$ alkylene-, —$C_{1-6}$ alkylene-O—$C_{1-6}$ alkylene-, —$C_{1-6}$ alkylene-S—$C$— alkylene-, —CON($R^8$)—, —N($R^8$) CO—, —$C_{1-6}$ alkylene-CON($R^8$)— or —CON($R^8$)—$C_{1-6}$ alkylene-;

$R^8$ represents hydrogen or $C_{1-6}$ alkyl;

ring A represents $C_{6-10}$ aryl or heteroaryl, and the other one of $R^1$ and $R^4$ represents hydrogen, hydroxy, amino, halogen, $C_{1-6}$ alkyl, $C_{1-6}$ alkoxy, cyano, carboxy, $C_{2-7}$ alkoxycarbonyl, carbamoyl, mono or di($C_{1-6}$ alkyl) amino, halo($C_{1-6}$ alkyl), hydroxy($C_{1-6}$ alkyl), cyano($C_{1-6}$ alkyl), carboxy($C_{1-6}$ alkyl), $C_{2-7}$ alkoxycarbonyl($C_{1-6}$ alkyl), carbamoyl($C_{1-6}$ alkyl) group, an amino($C_{1-6}$ alkyl), mono or di($C_{1-6}$ alkyl)amino($C_{1-6}$ alkyl), halo($C_{1-6}$ alkoxy), hydroxy($C_{1-6}$ alkoxy), carboxy($C_{1-6}$ alkoxy), $C_{2-7}$ alkoxycarbonyl($C_{1-6}$alkoxy), carbamoyl($C_{1-6}$ alkoxy), amino($C_{1-6}$ alkoxy), mono or di($C_{1-6}$ alkyl)amino($C_{1-6}$ alkoxy), $C_{3-7}$ cycloalkyl, $C_{3-7}$ cycloalkyloxy, $C_{3-7}$ cycloalkyl($C_{1-6}$ alkyl), or $C_{3-7}$ cycloalkyl($C_{1-6}$ alkoxy);

$R^2$ and $R^3$ independently represent hydrogen, hydroxy, amino, halogen, $C_{1-6}$ alkyl, $C_{1-6}$ alkoxy, cyano, carboxy, $C_{2-7}$ alkoxycarbonyl, carbamoyl, mono or di($C_{1-6}$ alkyl) amino, halo($C_{1-6}$ alkyl), hydroxy($C_{1-6}$ alkyl), cyano($C_{1-6}$ alkyl), carboxy($C_{1-6}$ alkyl), $C_{2-7}$ alkoxycarbonyl($C_{1-6}$ alkyl), carbamoyl($C_{1-6}$ alkyl), amino($C_{1-6}$ alkyl), mono or di($C_{1-6}$ alkyl)amino($C_{1-6}$ alkyl), halo($C_{1-6}$ alkoxy), hydroxy($C_{1-6}$ alkoxy), carboxy($C_{1-6}$ alkoxy), $C_{2-7}$ alkoxycarbonyl($C_{1-6}$alkoxy), carbamoyl($C_{1-6}$ alkoxy), amino ($C_{1-6}$ alkoxy), mono or di($C_{1-6}$ alkyl)amino($C_{1-6}$ alkoxy), $C_{3-7}$ cycloalkyl, $C_{3-7}$cycloalkyloxy, $C_{3-7}$cycloalkyl ($C_{1-6}$alkyl), or $C_{3-7}$ cycloalkyl($C_{1-6}$ alkoxy);

$A^1$ represents O, S or $NR^9$;

$A^2$ represents CH or N;

$R^9$ represents hydrogen or $C_{1-6}$ alkyl;

G represents a group represented by a formula:

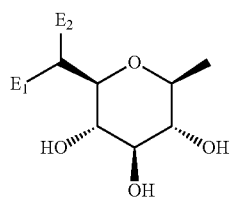

or a formula:

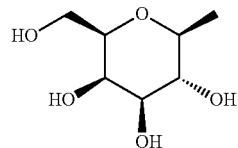

$E_1$ represents hydrogen, fluorine or hydroxy;

$E_2$ represents hydrogen, fluorine, methyl or hydroxymethyl;

[substituent group α]

halogen, hydroxy, amino, $C_{1-6}$ alkyl, $C_{1-6}$ alkoxy, halo($C_{1-6}$ alkyl), halo($C_{1-6}$ alkoxy), hydroxy($C_{1-6}$ alkyl), $C_{2-7}$ alkoxycarbonyl($C_{1-6}$ alkyl), hydroxy($C_{1-6}$ alkoxy), amino ($C_{1-6}$ alkyl), amino($C_{1-6}$ alkoxy), mono or di($C_{1-6}$ alkyl) amino, mono or di[hydroxy($C_{1-6}$ alkyl)]amino, $C_{1-6}$ alkylsulfonyl, $C_{1-6}$ alkylsulfonylamino, $C_{1-6}$ alkylsulfonylamino($C_{1-6}$ alkyl), carboxy, $C_{2-7}$ alkoxycarbonyl, sulfamoyl and —CON($R^H$)$R^I$

[substituent group β]

halogen atom, hydroxy, amino, $C_{1-6}$ alkoxy, $C_{1-6}$ alkylthio, halo($C_{1-6}$ alkoxy), halo($C_{1-6}$ alkylthio), hydroxy($C_{1-6}$ alkoxy), hydroxy($C_{1-6}$ alkylthio), amino($C_{1-6}$ alkoxy), amino($C_{1-6}$ alkylthio), mono or di($C_{1-6}$ alkyl)amino, mono or di[hydroxy($C_{1-6}$ alkyl)]amino, ureido, sulfamide, mono or di($C_{1-6}$ alkyl) ureido, mono or di[hydroxy($C_{1-6}$ alkyl)] ureido, mono or di($C_{1-6}$ alkyl)sulfamide, mono or di[hydroxy($C_{1-6}$ alkyl)]sulfamide, $C_{2-7}$ acylamino, amino($C_{2-7}$ acylamino), $C_{1-6}$ alkylsulfonyl, $C_{1-6}$ alkylsulfonylamino, carbamoyl($C_{1-6}$ alkylsulfonylamino), carboxy, $C_{2-7}$ alkoxycarbonyl group, —CON($R^H$) $R^I$, and any of the following substituents (xxxvii) to (xxxxviii) which may have 1 to 3 substituents selected from the above substituent group α;

(xxxvii) $C_{6-10}$ aryl, (xxxviii) $C_{6-10}$ aryl-O—, (xxxix) $C_{6-10}$ aryl($C_{1-6}$ alkoxy), (xxxx) $C_{6-10}$ aryl($C_{1-6}$ alkylthio), (xxxxi) heteroaryl, (xxxxii) heteroaryl-O—, (xxxxiii) $C_{3-7}$ cycloalkyl, (xxxxiv) $C_{3-7}$ cycloalkyl-O—, (xxxxv) heterocycloalkyl, (xxxxvi) heterocycloalkyl-O—, (xxxxvii) aliphatic cyclic amino or (xxxxviii) aromatic cyclic amino $R^H$ and $R^I$ independently represent hydrogen or $C_{1-6}$ alkyl which may have 1 to 3 substituents selected from the following substituent group γ;

or both of $R^H$ and $R^I$ bind together with the neighboring nitrogen to form aliphatic cyclic amino which may have 1 to 3 substituents selected from the following substituent group δ;

[substituent group γ]

halogen, hydroxy, amino, $C_{1-6}$ alkoxy, halo($C_{1-6}$ alkoxy), hydroxy($C_{1-6}$ alkoxy), amino($C_{1-6}$ alkoxy), mono or di($C_{1-6}$ alkyl)amino, mono or di[hydroxy($C_{1-6}$ alkyl)] amino, ureido, sulfamide, mono or di($C_{1-6}$ alkyl) ureido, mono or di[hydroxy($C_{1-6}$ alkyl)]ureido, mono or di($C_{1-6}$ alkyl)sulfamide, mono or di[hydroxy($C_{1-6}$ alkyl)]sulfamide, $C_{2-7}$ acylamino, amino($C_{2-7}$ acylamino), $C_{1-6}$ alkylsulfonyl, $C_{1-6}$ alkylsulfonylamino, carbamoyl($C_{1-6}$ alkylsulfonylamino), carboxy, $C_{2-7}$ alkoxycarbonyl, sulfamoyl and —CON($R^J$)$R^K$

[substituent group δ]

halogen, hydroxy, amino, $C_{1-6}$ alkyl, $C_{1-6}$ alkoxy, halo($C_{1-6}$ alkyl), halo($C_{1-6}$ alkoxy), hydroxy($C_{1-6}$ alkyl), $C_{2-7}$ alkoxycarbonyl($C_{1-6}$ alkyl), hydroxy($C_{1-6}$ alkoxy), amino ($C_{1-6}$ alkyl), amino($C_{1-6}$ alkoxy), mono or di($C_{1-6}$alkyl) amino, mono or di[hydroxy($C_{1-6}$ alkyl)]amino, $C_{1-6}$ alkylsulfonyl, $C_{1-6}$ alkylsulfonylamino, $C_{1-6}$ alkylsulfonylamino($C_{1-6}$ alkyl), carboxy, $C_{2-7}$ alkoxycarbonyl, sulfamoyl and —CON(R)$R^K$ $R^J$ and $R^K$ independently represent hydrogen or $C_{1-6}$ alkyl which may have any 1 to 3 substituents selected from hydroxy, amino, mono or di($C_{1-6}$ alkyl)amino, $C_{2-7}$ alkoxycarbonyl and carbamoyl;

or both of $R^J$ and $R^K$ bind together with the neighboring nitrogen to form aliphatic cyclic amino which may have any 1 to 3 substituents selected from hydroxy, amino, mono or di($C_{1-6}$ alkyl) amino, $C_{1-6}$ alkyl, hydroxy($C_{1-6}$ alkyl), $C_{2-7}$ alkoxycarbonyl, $C_{2-7}$ alkoxycarbonyl($C_{1-6}$ alkyl) and carbamoyl, or a pharmaceutically acceptable salt thereof, or a prodrug thereof.

In an embodiment of the present invention, the SGLT inhibitors are the compounds disclosed in WO 2005/085267 pamphlet, which are represented by Formula (11):

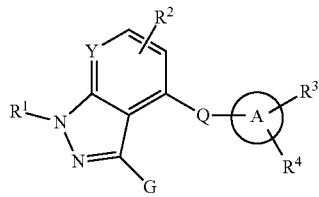

(11)

wherein $R^1$ represents hydrogen, $C_{1-6}$ alkyl, halo($C_{1-6}$ alkyl), hydroxy($C_{1-6}$ alkyl), dihydroxy($C_{1-6}$ alkyl), $C_{1-6}$ alkoxy($C_{1-6}$ alkyl), $C_{2-7}$ alkoxycarbonyl($C_{1-6}$ alkyl), carboxy($C_{1-6}$ alkyl), $C_{2-6}$ alkenyl, -J-N(R)—$Z^1$, -J-CON($R^5$)—$Z^1$, or any of the following substituents (a) to (d) which may have any 1 to 3 substituents selected from the following substituent group α on the ring;

(a) $C_{3-7}$cycloalkyl, (b) $C_{3-7}$ cycloalkyl($C_{1-6}$ alkyl), (c) $C_{6-10}$ aryl or (d) $C_{1-6}$ aryl($C_{6-10}$ alkyl), $R^2$ represents hydrogen, halogen or $C_{1-6}$ alkyl;

$R^3$ and $R^4$ independently represent hydrogen, hydroxy, halogen, $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylthio, $C_{2-6}$ alkenylthio, halo($C_{1-6}$ alkyl), halo($C_{1-6}$ alkoxy), halo($C_{1-6}$ alkylthio), hydroxy($C_{1-6}$ alkyl), hydroxy($C_{2-6}$alkenyl), hydroxy($C_{1-6}$ alkoxy), hydroxy($C_{1-6}$ alkylthio), carboxy, carboxy($C_{1-6}$ alkyl), carboxy($C_{2-6}$ alkenyl), carboxy($C_{1-6}$ alkoxy), carboxy($C_{1-6}$ alkylthio), $C_{2-7}$ alkoxycarbonyl, $C_{2-7}$ alkoxycarbonyl($C_{1-6}$ alkyl), $C_{2-7}$ alkoxycarbonyl($C_{2-6}$alkenyl), $C_{2-7}$ alkoxycarbonyl($C_{1-6}$ alkoxy), $C_{2-7}$ alkoxycarbonyl($C_{1-6}$ alkylthio), $C_{1-6}$ alkylsulfinyl, $C_{1-6}$alkylsulfonyl group, —U—V—W—N($R^6$)—$Z^2$, or any of the following substituents (i) to (xxviii) which may have any 1 to 3 substituents selected from the following substituent group α on the ring;

(i) $C_{6-10}$ aryl, (ii) $C_{6-10}$ aryl-O—, (iii) $C_{6-10}$ aryl-S—, (iv) $C_{6-10}$ aryl($C_{6-10}$ alkyl), (v) $C_{6-10}$ aryl($C_{1-6}$ alkoxy), (vi) $C_{6-10}$ aryl($C_{1-6}$ alkylthio), (vii) heteroaryl, (viii) heteroaryl-O—, (ix) heteroaryl-S—, (x) heteroaryl($C_{1-6}$ alkyl), (xi) heteroaryl($C_{1-6}$ alkoxy), (xii) heteroaryl($C_{1-6}$ alkylthio), (xiii) $C_{3-7}$ cycloalkyl, (xiv) $C_{3-7}$ cycloalkyl-O—, (xv) $C_{3-7}$cycloalkyl-S—, (xvi) $C_{3-7}$cycloalkyl($C_{1-6}$ alkyl), (xvii) $C_{3-7}$ cycloalkyl($C_{1-6}$ alkoxy), (xviii) $C_{3-7}$cycloalkyl($C_{1-6}$ alkylthio), (xix) heterocycloalkyl, (xx) heterocycloalkyl-O—, (xxi) heterocycloalkyl-S—, (xxii) heterocycloalkyl($C_{1-6}$ alkyl), (xxiii) heterocycloalkyl($C_{1-6}$ alkoxy), (xxiv) heterocycloalkyl($C_{1-6}$ alkylthio), (xxv) aromatic cyclic amino, (xxvi) aromatic cyclic amino($C_{1-6}$ alkyl), (xxvii) aromatic cyclic amino($C_{1-6}$ alkoxy), or (xxviii) aromatic cyclic amino($C_{1-6}$ alkylthio), J represents $C_{1-6}$ alkylene which may have hydroxy, or $C_{2-6}$ alkenylene;

U represents —O—, —S— or a single bond and with the proviso that at least one of V and W is not a single bond when U is —O— or —S—;

V represents $C_{1-6}$ alkylene which may have hydroxy, $C_{2-6}$ alkenylene or a single bond;

W represents —CO—, —$SO_2$—, —C(=NH)— or a single bond;

$Z^1$ and $Z^2$ independently represent hydrogen, $C_{2-7}$ alkoxycarbonyl, $C_{6-10}$ aryl($C_{2-7}$ alkoxycarbonyl), formyl, —$R^A$, —$COR^B$, —$SO_2RB$, —CON($R^C$)$R^D$, —CSN($R^C$)$R^D$, —$SO_2NHR^A$ or —C(=$NR^E$)N($R^F$)$R^G$;

$R^5$, $R^6$, $R^A$, $R^C$ and $R^D$ independently represent hydrogen, $C_{1-6}$ alkyl which may have any 1 to 5 substituents selected from the following substituent group β or any of the following substituents (xxix) to (xxxii) which may have any 1 to 3 substituents selected from the following substituent group α;

(xxix) $C_{6-10}$ aryl, (xxx) heteroaryl, (xxxi) $C_{3-7}$cycloalkyl or (xxxii) heterocycloalkyl, or both of $Z^1$ and $R^5$ or both of $Z^2$ and $R^6$ bind together with the neighboring nitrogen to form aliphatic cyclic amino which may have any 1 to 3 substituents selected from the following substituent group α;

or $R^C$ and $R^D$ bind together with the neighboring nitrogen to form aliphatic cyclic amino which may have any 1 to 3 substituents selected from the following substituent group α;

$R^B$ represents $C_{2-7}$ alkoxycarbonyl, $C_{1-6}$ alkylsulfonylamino, $C_{6-10}$arylsulfonylamino, $C_{1-6}$ alkyl which may have any 1 to 5 substituents selected from the following substituent group 0 or any of the following substituents (xxxiii) to (xxxvi) which may have any 1 to 3 substituents selected from the following substituent group α;

(xxxiii) $C_{6-10}$ aryl, (xxxiv) heteroaryl, (xxxv) $C_{3-7}$cycloalkyl or (xxxvi) heterocycloalkyl, $R^E$, $R^F$ and $R^G$ independently represent hydrogen, cyano, carbamoyl, $C_{2-7}$ acyl group, $C_{2-7}$ alkoxycarbonyl, $C_{6-10}$ aryl($C_{2-7}$ alkoxycarbonyl), nitro, $C_{1-6}$ alkylsulfonyl, sulfamoyl, carbamimidoyl or $C_{1-6}$ alkyl which may have any 1 to 5 substituents selected from the following substituent group β;

or $R^E$ and $R^F$ bind together to form ethylene;

or $R^F$ and $R^G$ bind together with the neighboring nitrogen to form aliphatic cyclic amino which may have a substituent selected from the following substituent group α;

Y represents CH or N;

Q represents —$C_{1-6}$ alkylene-, —$C_{2-6}$ alkenylene-, —$C_{2-6}$alkynylene-, —$C_{1-6}$ alkylene-O—, —$Cl_{1-6}$ alkylene-S—, —O—$C_{1-6}$ alkylene-, —S—$C_{1-6}$ alkylene-, —$C_{1-6}$ alkylene-O—$C_{1-6}$ alkylene-, —$C_{1-6}$alkylene-S—$C_{1-6}$ alkylene-, —CON(R)—, —N($R^7$)CO—, —$C_{1-6}$ alkylene-CON($R^7$)— or —CON($R^7$)—$C_{1-6}$ alkylene-;

$R^7$ represents hydrogen or $C_{1-6}$ alkyl;

ring A represents $C_{6-10}$ aryl or heteroaryl;

G represents a group represented by a formula:

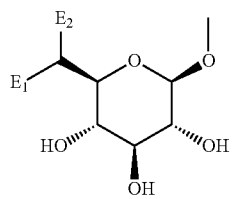

or a formula:

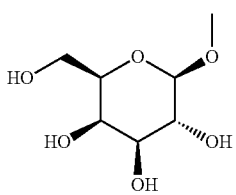

$E^1$ represents hydrogen, fluorine or hydroxy;
$E^2$ represents hydrogen, fluorine, methyl or hydroxymethyl;

[substituent group α]

halogen, hydroxy, amino, $C_{1-6}$ alkyl, $C_{1-6}$ alkoxy, halo($C_{1-6}$ alkyl), a halo($C_{1-6}$ alkoxy), hydroxy($C_{1-6}$ alkyl), $C_{2-7}$alkoxycarbonyl($C_{1-6}$ alkyl), hydroxy($C_{1-6}$ alkoxy), amino($C_{1-6}$ alkyl), amino($C_{1-6}$ alkoxy), mono or di($C_{1-6}$ alkyl)amino, mono or di[hydroxy($C_{1-6}$ alkyl)]amino, $C_{1-6}$-alkylsulfonyl, $C_{1-6}$ alkylsulfonylamino, $C_{1-6}$ alkylsulfonylamino($C_{1-6}$ alkyl), carboxy, $C_{2-7}$ alkoxycarbonyl, sulfamoyl and —CON($R^H$)$R^I$

[substituent group β]

halogen, hydroxy, amino, $C_{1-6}$ alkoxy, $C_{1-6}$ alkylthio, halo ($C_{1-6}$ alkoxy), halo($C_{1-6}$ alkylthio), hydroxy($C_{1-6}$ alkoxy), hydroxy($C_{1-6}$ alkylthio), amino($C_{1-6}$ alkoxy), amino($C_{1-6}$ alkylthio), mono or di($C_{1-6}$ alkyl)amino, mono or di[hydroxy($C_{1-6}$ alkyl)]amino, ureido, sulfamide, mono or di($C_{1-6}$ alkyl) ureido, mono or di[hydroxy($C_{1-6}$ alkyl)]ureido, mono or di($C_{1-6}$ alkyl)sulfamide, mono or di[hydroxy ($C_{1-6}$ alkyl)]-sulfamide, $C_{2-7}$ acylamino, amino($C_{2-7}$ acylamino), $C_{1-6}$ alkyl-sulfonyl, $C_{1-6}$ alkylsulfonylamino, carbamoyl($C_{1-6}$ alkylsulfonylamino), carboxy, $C_{2-7}$ alkoxycarbonyl, —CON($R^H$)$R^I$, and any of the following substituents (xxxvii) to (xxxxviii) which may have any 1 to 3 substituents selected from the above substituent group α on the ring;

(xxxvii) $C_{6-10}$ aryl, (xxxviii) $C_{6-10}$ aryl-O—, (xxxix) $C_{6-10}$ aryl($C_{1-6}$ alkoxy), (xxxx) $C_{6-10}$ aryl($C_{1-6}$ alkylthio), (xxxxi) heteroaryl, (xxxxii) heteroaryl-O—, (xxxxiii) $C_{3-7}$ cycloalkyl, (xxxxiv) $C_{3-7}$ cycloalkyl-O—, (xxxxv) heterocycloalkyl, (xxxxvi) heterocycloalkyl-O—, (xxxxvii) aliphatic cyclic amino or (xxxxviii) aromatic cyclic amino $R^H$ and $R^I$ independently represent hydrogen or $C_{1-6}$ alkyl which may have any 1 to 3 substituents selected from the following substituent group γ;

or both of $R^H$ and $R^I$ bind together with the neighboring nitrogen to form aliphatic cyclic amino which may have any 1 to 3 substituents selected from the following substituent group δ;

[substituent group γ]

halogen, hydroxy, amino, $C_{1-6}$ alkoxy, halo($C_{1-6}$ alkoxy), hydroxy($C_{1-6}$ alkoxy), amino($C_{1-6}$ alkoxy), mono or di($C_{1-6}$ alkyl)amino, mono or di[hydroxy($C_{1-6}$ alkyl)] amino, ureido, sulfamide, mono or di($C_{1-6}$ alkyl)ureido, mono or di[hydroxy($C_{1-6}$ alkyl)]ureido, mono or di($C_{1-6}$ alkyl)sulfamide, mono or di[hydroxy($C_{1-6}$ alkyl)]sulfamide, $C_{2-7}$ acylamino, amino($C_{2-7}$ acylamino), $C_{1-6}$ alkylsulfonyl, $C_{1-6}$ alkylsulfonylamino, carbamoyl($C_{1-6}$ alkylsulfonylamino), carboxy, $C_{2-7}$alkoxycarbonyl and —CON($R^J$)$R^K$

[substituent group δ]

halogen, hydroxy, amino, $C_{1-6}$ alkyl, $C_{1-6}$ alkoxy, halo($C_{1-6}$alkyl), halo($C_{1-6}$ alkoxy), hydroxy($C_{1-6}$ alkyl), $C_{2-7}$ alkoxycarbonyl($C_{1-6}$ alkyl), hydroxy($C_{1-6}$ alkoxy), amino($C_{1-6}$ alkyl), amino($C_{1-6}$ alkoxy), mono or di($C_{1-6}$ alkyl)amino, mono or di[hydroxy($C_{1-6}$ alkyl)]amino, $C_{1-6}$ alkylsulfonyl, $C_{1-6}$ alkylsulfonylamino, $C_{1-6}$ alkylsulfonylamino($C_{1-6}$ alkyl), carboxy, $C_{2-7}$ alkoxycarbonyl, sulfamoyl and —CON($R^J$)$R^K$ $R^J$ and $R^K$ independently represent hydrogen or $C_{1-6}$ alkyl which may have any 1 to 3 substituents selected from hydroxy, amino, mono or di($C_{1-6}$ alkyl)amino, $C_{2-7}$ alkoxycarbonyl and carbamoyl;

or both of $R^J$ and $R^K$ bind together with the neighboring nitrogen to form aliphatic cyclic amino which may have any 1 to 3 substituents selected from hydroxy, amino, mono or di($C_{1-6}$ alkyl)amino, $C_{1-6}$ alkyl, hydroxy($C_{1-6}$ alkyl), $C_{2-7}$ alkoxycarbonyl, $C_{2-7}$ alkoxycarbonyl($C_{1-6}$ alkyl) and carbamoyl, or a pharmaceutically acceptable salt thereof, or a prodrug thereof.

In an embodiment of the present invention, the SGLT inhibitors are the glucopyranosyloxypyrazole derivatives disclosed in WO 01/16147 pamphlet, which are represented by Formula (12):

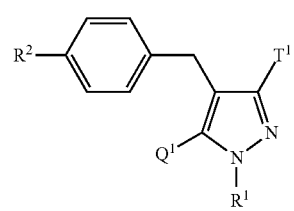

(12)

wherein $R^1$ represents hydrogen or lower alkyl; one of $Q^1$ and $T^1$ represents a group represented by the formula:

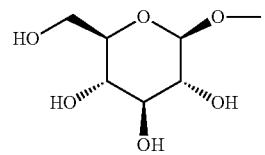

while the other represents lower alkyl or halo(lower alkyl); and $R^2$ represents hydrogen, lower alkyl, lower alkoxy, lower alkylthio, halo(lower alkyl) or halogen, or a pharmaceutically acceptable salt thereof.

In an embodiment of the present invention, the SGLT inhibitors are the compounds disclosed in WO 2006/035796 pamphlet, which are represented by Formula (13):

(13)

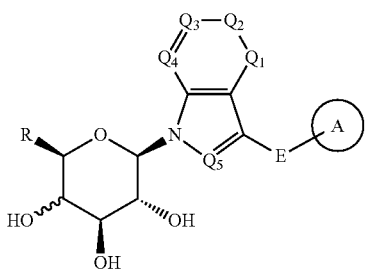

wherein Ring A represents aryl or heteroaryl, each of which may have a substituent(s), $Q^1$ to $Q^5$ are each independently carbon to which hydrogen or a substituent is connected, or nitrogen, E represents a single bond, alkylene, —O—, —S— or —NH—, and R represents methyl, ethyl, fluoromethyl or hydroxymethyl, or a prodrug thereof or a pharmaceutically acceptable salt thereof, or a hydrate or solvate thereof.

In an embodiment of the present invention, the SGLT inhibitors are the azulene derivatives disclosed in WO 2004/013118 pamphlet, which are represented by Formula (14):

(14)

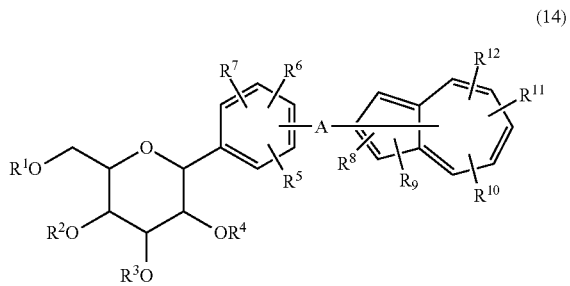

wherein $R^1$ to $R^4$ individually represent hydrogen, optionally substituted lower alkyl, —C(=O)-optionally substituted lower alkyl, or -optionally substituted lower alkylene-optionally substituted aryl, $R^5$ to $R^{12}$ individually represent hydrogen, optionally substituted lower alkyl, halogen, —OH, —O-optionally substituted lower alkyl, -optionally substituted lower alkylene-OH, -optionally substituted lower alkylene-O-optionally substituted lower alkyl, —O-optionally substituted lower alkylene-O-optionally substituted lower alkyl, —O-optionally substituted lower alkylene-optionally substituted aryl, -optionally substituted lower alkylene-O—C(=O)-optionally substituted lower alkyl, —COOH, nitro, cyano, amino, substituted amino, or —C(=O)—O-optionally substituted lower alkyl, and A represents bond or optionally substituted lower alkylene, wherein -A- may be bonded to any one of the positions 1-8 of the azulene ring, and any two of $R^5$, $R^6$, and $R^7$ may form a benzene ring together with the adjacent carbon atoms.

In still another embodiment of the present invention, the SGLT inhibitors are the compounds disclosed in WO 2004/080990 pamphlet, which are represented by Formula (15):

(15)

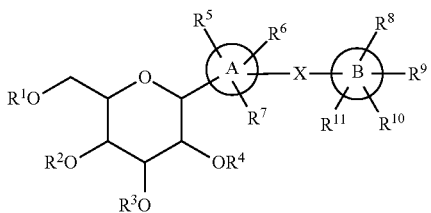

wherein A ring represents (1) benzene, (2) five or six-membered monocyclic heteroaryl having 1 to 4 hetero atom(s) selected from N, S, and O, or (3) saturated or unsaturated eight to ten-membered heterobicyclic having 1 to 4 hetero atom(s) selected from N, S, and O;

B ring represents (1) saturated or unsaturated eight to ten-membered heterobicyclic having 1 to 4 hetero atom(s) selected from N, S, and O, (2) saturated or unsaturated five or six-membered heteromonocyclic having 1 to 4 hetero atom(s) selected from N, S, and O, (3) a saturated or an unsaturated eight to ten-membered bicyclic hydrocarbon, or (4) benzene;

X represents bond or lower alkylene;

wherein Ring A, Ring B, and X have a correlation that (1) when Ring A is benzene, Ring B is a ring other than benzene or that (2) when Ring A is benzene, and Ring B is saturated or unsaturated eight to ten-membered heterobicyclic having 1 to 4 hetero atom(s) selected from N, S, and O including benzene, or saturated or unsaturated eight to ten-membered bicyclic hydrocarbon including benzene, X is bonded to Ring B in a part other than the benzene ring included in Ring B: incidentally, this correlation specifically means that Ring A and Ring B cannot be benzene simultaneously and that when Ring A is benzene and Ring B is benzofuran or indane, X is not benzene constituting a part of Ring B but bonds with furan or cyclopentane;

$R^1$ to $R^4$ individually represent hydrogen, lower alkyl, —C(=O)-lower alkyl, or -lower alkylene-aryl; and $R^5$ to $R^{11}$ individually represent hydrogen, lower alkyl, cycloalkyl, halogen, halogen-substituted lower alkyl, —OH, =O, —NH$_2$, lower alkylsulfonyl-, halogen-substituted lower alkylsulfonyl-, aryl sulfonyl-, aryl, saturated or unsaturated five or six-membered heteromonocyclic having 1 to 4 hetero atom(s) selected from N, S, and O, -lower alkylene-OH, -lower alkylene-O-lower alkyl, -lower alkylene-O—C(=O)-lower alkyl, -lower alkylene-O-lower alkylene-COOH, -lower alkylene-O-lower alkylene-C(=O)—O-lower alkyl, -lower alkylene-NH$_2$, -lower alkylene-NH-lower alkyl, -lower alkylene-N(lower alkyl)$_2$, -lower alkylene-NH—C(=O)-lower alkyl, —COOH, —CN, —C(=O)—O-lower alkyl, —C(=O)—NH$_2$, —C(=O)—NH-lower alkyl, —C(=O)—N(lower alkyl)$_2$, —O-lower alkyl, —O-cycloalkyl, —O-lower alkylene-OH, —O-lower alkylene-O-lower alkyl, —O-lower alkylene-COOH, —O-lower alkylene-C(=O)—O-lower alkyl, —O-lower alkylene-C(=O)—NH$_2$, —O-lower alkylene-C(=O)—NH-lower alkyl, —O-lower alkylene-C(=O)—N(lower alkyl)$_2$, —O-lower alkylene-CH(OH)—CH$_2$(OH), —O-lower alkylene-NH$_2$, —O-lower alkylene-NH-lower alkyl, —O-lower alkylene-N(lower alkyl)$_2$, —O-lower alkylene-NH—C(=O)-lower alkyl, —NH-lower alkyl, —N(lower alkyl)$_2$, —NH—SO$_2$-lower alkyl, —NH—SO$_2$-halogen-substituted lower alkyl, —NH-lower alkylene-OH, —NH—C(=O)-lower alkyl, —NH—C(=O)—NH$_2$, —NH—C(═O)—NH-lower alkyl, —NH—C(═O)—N(lower alkyl)$_2$, or —NH—C(═O)—O-lower alkyl.

In a preferable embodiment of the present invention, the SGLT inhibitors are represented by Formula (15a):

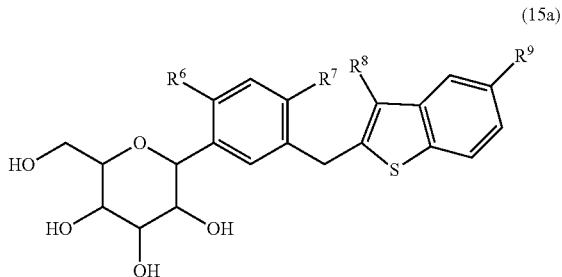

(15a)

wherein: $R^6$ represents a hydrogen atom, halogen atom, —OH, —OMe, —CH$_2$—OH, —O—(CH$_2$)$_2$—OH, —O—(CH$_2$)$_2$—NH$_2$—COOH, —COOEt, —O—CH$_2$—COOH, or —O—CH$_2$—COOEt, $R^7$ represents a hydrogen atom or halogen atom, $R^8$ represents a hydrogen atom, or -Me, and $R^9$ represents a hydrogen atom, -Me, halogen atom, or —OMe.

In an embodiment of the present invention, the SGLT inhibitors are the glucopyranosyl-substituted benzene derivatives disclosed in WO 2005/092877 pamphlet, which are represented by Formula (16):

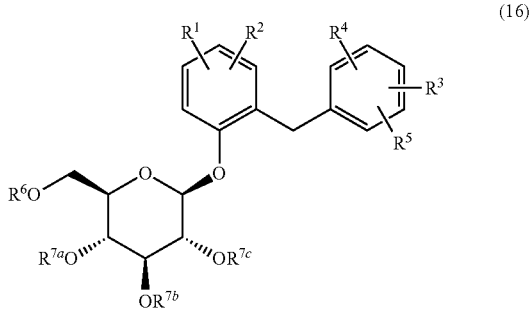

(16)

wherein $R^1$ is selected from the definitions of the group A, and if $R^3$ is selected from the definitions of the group B, $R^1$ may additionally be selected from hydrogen, fluorine, chlorine, bromine, iodine, $C_{1-4}$ alkyl, $C_{2-4}$ alkenyl-$C_{1-4}$ alkyl, $C_{2-4}$ alkynyl-$C_{1-4}$ alkyl, $C_{2-4}$ alkenyl-$C_{1-4}$ alkoxy, $C_{2-4}$ alkynyl-$C_{1-4}$ alkoxy, $C_{3-7}$ cycloalkyl-$C_{1-4}$ alkyl, $C_{5-7}$ cycloalkenyl-$C_{1-4}$ alkyl, methyl substituted by 1 to 3 fluorine, ethyl substituted by 1 to 5 fluorine, $C_{1-4}$ alkoxy, methoxy substituted by 1 to 3 fluorine, ethoxy substituted by 1 to 5 fluorine, $C_{1-4}$ alkyl substituted by hydroxy or $C_{1-3}$ alkoxy, $C_{2-4}$ alkoxy substituted by hydroxy or $C_{1-3}$ alkoxy, $C_{3-6}$ cycloalkyl-$C_{1-3}$ alkoxy or hydroxy, while in the above-mentioned cycloalkyl and cycloalkenyl rings one or two methylene groups may be replaced independently of one another by O or CO;

$R^2$ denotes hydrogen, fluorine, chlorine, bromine, hydroxy, $C_{1-4}$ alkyl, $C_{1-4}$ alkoxy, cyano or nitro, while the alkyl or alkoxy group may be mono- or polysubstituted by fluorine;

$R^3$ is selected from the definitions of the group B, and if $R^1$ is selected from the definitions of the group A, $R^3$ may additionally be selected from the meanings hydrogen, fluorine, chlorine, bromine, iodine, $C_{1-6}$ alkyl, $C_{2-4}$ alkenyl-$C_{1-4}$ alkyl, $C_{2-4}$ alkynyl-$C_{1-4}$ alkyl, $C_{2-4}$ alkenyl-$C_{1-4}$ alkoxy, $C_{2-4}$ alkynyl-$C_{1-4}$ alkoxy, $C_{3-7}$ cycloalkyl, $C_{5-7}$ cycloalkenyl, $C_{3-7}$ cycloalkyl-$C_{1-4}$ alkyl, $C_{5-7}$ cycloalkenyl-$C_{1-4}$ alkyl, $C_{3-6}$ cycloalkylidenemethyl, hydroxy, $C_{1-6}$ alkoxy, $C_{3-6}$ cycloalkyl-$C_{1-3}$ alkoxy, aryl, aryl-$C_{1-3}$ alkyl, heteroaryl, heteroaryl-$C_{1-3}$ alkyl, aryloxy, aryl-$C_{1-3}$ alkyl-oxy, methyl or methoxy substituted by 1 to 3 fluorine, $C_{2-4}$ alkyl or $C_{2-4}$ alkoxy substituted by 1 to 5 fluorine, $C_{1-4}$ alkyl substituted by cyano, $C_{1-4}$ alkyl substituted by hydroxy or $C_{1-3}$ alkyloxy, cyano, carboxy, $C_{1-3}$ alkoxycarbonyl, aminocarbonyl, ($C_{1-3}$ alkylamino)carbonyl, di-($C_{1-3}$ alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-3}$ alkyl)-piperazin-1-ylcarbonyl, ($C_{1-4}$ alkyl)carbonylamino, $C_{1-4}$ alkyl-sulfonylamino, $C_{1-4}$ alkylsulfanyl, $C_{1-4}$ alkylsulfinyl, $C_{1-4}$ alkylsulfonyl, arylsulfonylamino, aryl-$C_{1-3}$ alkylsulfonylamino or arylsulfonyl;

$R^4$ and $R^5$ independently of one another denote hydrogen, fluorine, chlorine, bromine, iodine, cyano, nitro, $C_{1-3}$ alkyl, $C_{1-3}$ alkoxy, or methyl or methoxy substituted by 1 to 3 fluorine, A denotes $C_{2-6}$ alkyn-1-yl, $C_{2-6}$ alken-1-yl, $C_{3-7}$ cycloalkyl, $C_{5-7}$ cycloalkenyl, aryl, heteroaryl, $C_{1-4}$ alkylcarbonyl, arylcarbonyl, heteroarylcarbonyl, aminocarbonyl, $C_{1-4}$ alkylaminocarbonyl, di-($C_{1-3}$ alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$ alkyl)piperazin-1-ylcarbonyl, arylamino-carbonyl, heteroarylaminocarbonyl, $C_{1-4}$ alkoxycarbonyl, aryl-$C_{1-3}$ alkoxycarbonyl, heteroaryl-$C_{1-3}$ alkoxycarbonyl, amino, $C_{1-4}$ alkylamino, di-($C_{1-3}$ alkyl)amino, pyrrolidin-1-yl, pyrrolidin-2-on-1-yl, piperidin-1-yl, piperidin-2-on-1-yl, morpholin-4-yl, morpholin-3-on-4-yl, piperazin-1-yl, 4-($C_{1-3}$ alkyl)piperazin-1-yl, $C_{1-4}$ alkylcarbonylamino, arylcarbonylamino, heteroarylcarbonylamino, $C_{3-7}$ cycloalkyloxy, $C_{5-7}$ cycloalkenyloxy, aryloxy, heteroaryloxy, $C_{1-4}$ alkylsulfinyl, $C_{1-4}$ alkylsulfonyl, $C_{3-7}$ cycloalkylsulfanyl, $C_{3-7}$ cycloalkylsulfinyl, $C_{3-7}$ cycloalkylsulfonyl, $C_{5-7}$ cycloalkenylsulfanyl, $C_{5-7}$ cycloalkenylsulfinyl, $C_{5-7}$ cycloalkenylsulfonyl, arylsulfanyl, arylsulfinyl, arylsulfonyl, heteroarylsulfanyl, heteroarylsulfinyl, heteroarylsulfonyl, cyano or nitro, while the above-mentioned alkynyl and alkenyl groups may be mono- or polysubstituted by fluorine or chlorine, and the above-mentioned alkynyl and alkenyl groups may be mono- or di-substituted by identical or different groups $L^1$, and the above-mentioned cycloalkyl and cycloalkenyl rings independently of one another may be mono- or di-substituted by substituents selected from fluorine and $C_{1-3}$ alkyl, and in the above-mentioned cycloalkyl and cycloalkenyl rings one or two methylene groups may be replaced independently of one another by O, S, CO, SO, SO$_2$ or NR$^N$;

B denotes tri-($C_{1-4}$ alkyl)silyl-$C_{1-6}$ alkyl, $C_{2-6}$ alkyn-1-yl, $C_{2-6}$ alken-1-yl, amino, $C_{1-3}$ alkylamino, di-($C_{1-3}$ alkyl)amino, pyrrolidin-1-yl, pyrrolidin-2-on-1-yl, piperidin-1-yl, piperidin-2-on-1-yl, morpholin-4-yl, morpholin-3-on-4-yl, piperazin-1-yl, 4-($C_{1-3}$ alkyl)piperazin-1-yl, arylcarbonylamino, heteroarylcarbonylamino, nitro, $C_{3-10}$ cycloalkyloxy, $C_{5-10}$ cycloalkenyloxy, $C_{3-10}$ cycloalkylsulfanyl, $C_{3-10}$ cycloalkylsulfinyl, $C_{3-10}$ cycloalkylsulfinyl, $C_{5-10}$ cycloalkenylsulfanyl, $C_{5-10}$ cycloalkenylsulfinyl, $C_{5-10}$ cycloalkenylsulfonyl, arylsulfanyl, arylsulfinyl, heteroarylsulfanyl or heteroarylsulfinyl, while the above-mentioned alkynyl and alkenyl groups may be mono- or polysubstituted by fluorine or chlorine, and the above-mentioned alkynyl and alkenyl groups may be mono- or di-substituted by identical or different groups $L^1$; while the above-mentioned cycloalkyl and cycloalkenyl rings may be mono- or di-substituted independently of one another by substituents selected from fluorine and $C_{1-3}$ alkyl, and in the above-mentioned cycloalkyl and cycloalkenyl rings one or two methylene groups may be replaced independently of one another by O, S, CO, SO, $SO_2$ or $NR^N$;

$R^N$ denotes H, $C_{1-4}$ alkyl, $C_{1-4}$ alkylcarbonyl or $C_{1-4}$ alkylsulfonyl, $L^1$ independently of one another is selected from hydroxy, cyano, nitro, $C_{3-7}$ cycloalkyl, aryl, heteroaryl, $C_{1-4}$ alkylcarbonyl, arylcarbonyl, heteroarylcarbonyl, aminocarbonyl, alkylaminocarbonyl, di-($C_{1-3}$ alkyl)-aminocarbonyl, pyrrolidin-1-ylcarbonyl, piperidin-1-ylcarbonyl, morpholin-4-ylcarbonyl, arylaminocarbonyl, heteroarylaminocarbonyl, $C_{1-4}$ alkoxycarbonyl, aryl-$C_{1-3}$ alkoxycarbonyl, heteroaryl-$C_{1-3}$ alkoxycarbonyl, $C_{1-4}$ alkyloxy, aryloxy, heteroaryloxy, $C_{1-4}$ alkylsulfanyl, arylsulfanyl, heteroarylsulfanyl, $C_{1-4}$ alkylsulfinyl, arylsulfinyl, heteroarylsulfinyl, $C_{1-4}$ alkylsulfonyl, arylsulfonyl and heteroarylsulfonyl;

$L^2$ independently of one another is selected from fluorine, chlorine, bromine, iodine, $C_{1-3}$ alkyl, difluoromethyl, trifluoromethyl, $C_{1-3}$ alkoxy, difluoromethoxy, trifluoromethoxy and cyano;

$R^6$, $R^{7a}$, $R^{7b}$, and $R^{7c}$ independently of one another have a meaning selected from hydrogen, ($C_{1-18}$-alkyl)carbonyl, ($C_{1-18}$-alkyl)oxycarbonyl, arylcarbonyl and aryl-($C_{1-3}$ alkyl)-carbonyl, while the aryl group mentioned in the definition of the above groups are meant phenyl or naphthyl group which may be mono- or di-substituted independently of one another by identical or different groups $L^2$; and the heteroaryl group mentioned in the definition of the above groups are meant a pyrrolyl, furanyl, thienyl, pyridyl, indolyl, benzofuranyl, benzothiophenyl, quinolinyl, isoquinolinyl or tetrazolyl group, or is meant pyrrolyl, furanyl, thienyl or pyridyl, wherein one or two methyne groups are replaced by nitrogen, or is meant indolyl, benzofuranyl, benzothiophenyl, quinolinyl or isoquinolinyl, wherein one to three methyne groups are replaced by nitrogen, while the above-mentioned heteroaryl groups independently of one another may be mono- or di-substituted by identical or different groups $L^2$; while, unless otherwise stated, the above-mentioned alkyl group may be straight-chain or branched, the tautomers, the stereoisomers thereof, the mixtures thereof and the salts thereof.

In a preferable embodiment of the present invention, the SGLT inhibitor is the compound disclosed in WO 2006/117359 pamphlet, which is represented by Formula (17):

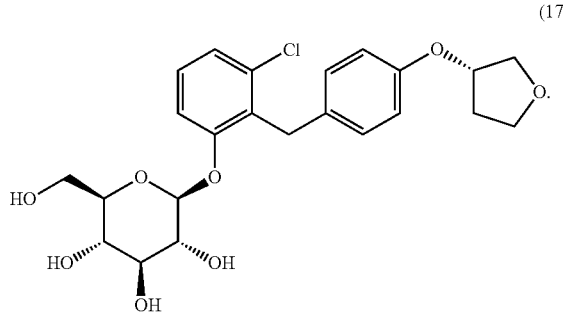

(17)

In another preferable embodiment of the present invention, the SGLT inhibitor is the compound disclosed in WO 2006/117360 pamphlet, which is represented by Formula (18):

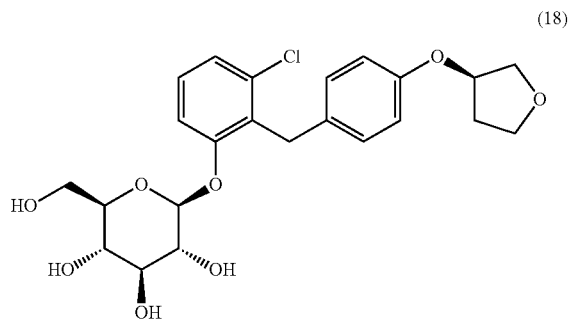 [SMILES: OC[C@H]1O[C@@H](Oc2cccc(Cl)c2Cc2ccc(O[C@@H]3CCOC3)cc2)[C@H](O)[C@@H](O)[C@@H]1O]

(18)

In an embodiment of the present invention, the SGLT inhibitors are the propiophenone derivatives disclosed in U.S. Pat. No. 6,048,842, or a pharmaceutically acceptable salt thereof, which are represented by Formula (19):

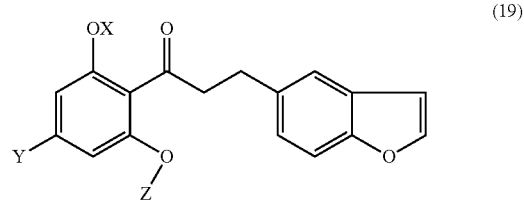

(19)

wherein OX is a hydroxy group which may optionally be protected, Y is a lower alkyl group, and Z is a β-D-glucopyranosyl group wherein one or more hydroxy groups may optionally be protected.

In an embodiment of the present invention, the SGLT inhibitors are the propiophenone derivatives disclosed in U.S. Pat. No. 5,830,873, or a pharmaceutically acceptable salt thereof, which are represented by Formula (20):

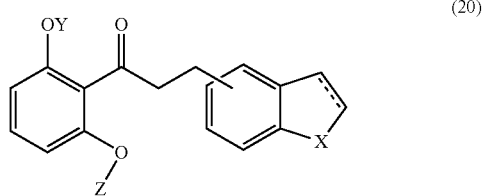

(20)

wherein X is an oxygen atom, a sulfur atom or a methylene group, OY is a protected or unprotected hydroxy group, Z is a β-D-glucopyranosyl group or 4-O-(α-D-glucopyranosyl)-β-D-glucopyranosyl group wherein one or more hydroxy groups of these groups may optionally be acylated, and the dotted line means the presence or absence of a double bond.

In an embodiment of the present invention, the SGLT inhibitors are the propiophenone derivatives or a pharmaceutically acceptable salt thereof, disclosed in U.S. Pat. No. 5,767,094, which are represented by Formula (21):

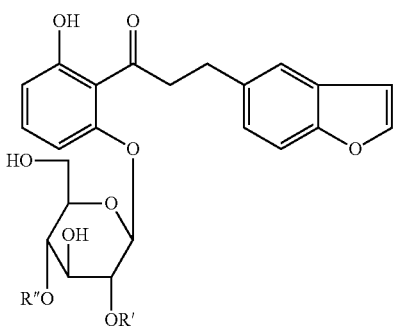

(21)

wherein R' is a lower alkanoyl group, and R" is a hydrogen atom, or R' is a hydrogen atom, and R" is a lower alkoxycarbonyl group.

In an embodiment of the present invention, the SGLT inhibitor is the propiophenone derivatives or a pharmaceutically acceptable salt thereof disclosed in U.S. Pat. Nos. 5,424, 406 and 5,731,292, which are represented by Formula (22):

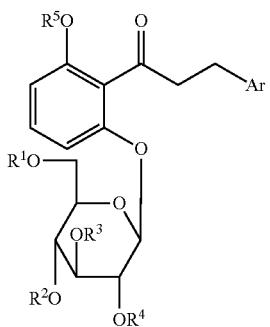

(22)

wherein Ar is an aryl group, $R^1$ is hydrogen atom or an acyl group, $R^2$ is hydrogen atom, an acyl group or α-D-glucopyranosyl group, or $R^1$ and $R^2$ may combine together to form a substituted methylene group, $R^3$ and $R^4$ are each hydrogen atom or an acyl group, and $OR^5$ is a protected or unprotected hydroxy group or a lower alkoxy group.

In an embodiment of the present invention, the SGLT inhibitors are the compounds disclosed in United States Patent Application Publication No. 2005/0233988, which are represented by Formula (23):

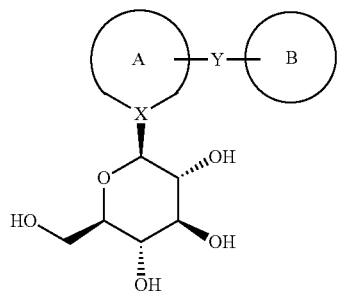

(23)

wherein Ring A and Ring B are one of the followings: (1) Ring A is optionally substituted unsaturated heteromonocyclic, and Ring B is optionally substituted unsaturated heteromonocyclic, optionally substituted unsaturated fused heterobicyclic, or optionally substituted benzene, (2) Ring A is optionally substituted benzene, and Ring B is optionally substituted unsaturated heteromonocyclic, or optionally substituted unsaturated fused heterobicyclic wherein Y is linked to the heterocyclic ring of said fused heterobicyclic, or (3) Ring A is optionally substituted unsaturated fused heterobicyclic, wherein the sugar moiety X-(sugar) and the moiety —Y-(Ring B) are both on the same heterocyclic ring of said fused heterobicyclic, and Ring B is optionally substituted unsaturated heteromonocyclic, optionally substituted unsaturated fused heterobicyclic, or optionally substituted benzene;

X is carbon or nitrogen; and

Y is —$(CH_2)_n$— (wherein n is 1 or 2);

a pharmaceutically acceptable salt thereof, or a prodrug thereof.

In a preferable embodiment, the SGLT inhibitors are the compounds of Formula (24):

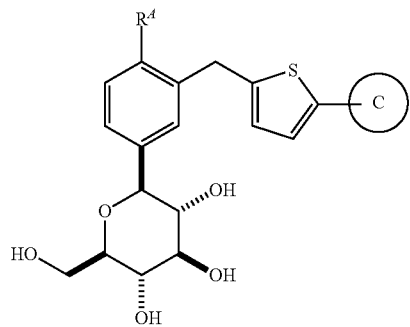

(24)

wherein $R^A$ is a halogen atom, or a lower alkyl group;

Ring C is a phenyl group substituted by 1-3 substituents selected from the group consisting of a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group substituted by 1-3 substituents selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group;

or a pharmaceutically acceptable salt thereof, or a prodrug thereof.

Examples of the preferable compounds include:

1-(β-D-glucopyranosyl)-4-chloro-3-[5-(5-thiazolyl)-2-thienylmethyl]benzene;

1-(β-D-glucopyranosyl)-4-chloro-3-(5-phenyl-2-thienylmethyl)benzene;

1-(β-D-glucopyranosyl)-4-chloro-3-[5-(2-pyrimidinyl)-2-thienylmethyl]benzene;

1-(β-D-glucopyranosyl)-4-methyl-3-[5-(2-pyrimidinyl)-2-thienylmethyl]benzene;

1-(β-D-glucopyranosyl)-4-chloro-3-[5-(3-cyanophenyl)-2-thienylmethyl]benzene;

1-(β-D-glucopyranosyl)-4-chloro-3-[5-(4-cyanophenyl)-2-thienylmethyl]benzene;

1-(β-D-glucopyranosyl)-4-chloro-3-[5-(6-fluoro-2-pyridyl)-2-thienylmethyl]benzene;

1-(β-D-glucopyranosyl)-4-chloro-3-[5-(6-fluoro-3-pyridyl)-2-thienylmethyl]benzene;

1-(β-D-glucopyranosyl)-4-methyl-3-[5-(6-fluoro-2-pyridyl)-2-thienylmethyl]benzene; and 1-(β-D-glucopyranosyl)-4-methyl-3-[5-(3-difluoromethylphenyl)-2-thienylmethyl]benzene.

In an embodiment of the present invention, the SGLT inhibitors are the indole derivatives disclosed in WO 2006/080577 pamphlet, which are represented by Formula (25):

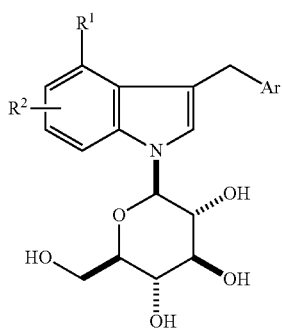

(25)

wherein $R^1$ is halogen, or alkyl, $R^2$ is hydrogen, or halogen, and

Ar is one of the following groups:

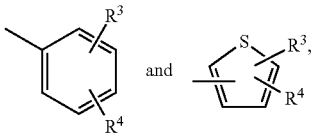

in which $R^3$ and $R^4$ are independently hydrogen, halogen, alkyl, cycloalkyl, haloalkyl, alkoxy, haloalkoxy, alkylthio, hydroxy, phenyl, halophenyl, cyanophenyl, pyridyl, halopyridyl, thienyl, or halothienyl, or $R^3$ and $R^4$ together with carbon atoms to which they are attached form a fused benzene, furan or dihydrofuran ring;

or a pharmaceutically acceptable salt thereof.

Examples of the preferable compounds include:

4-chloro-3-(4-ethylphenylmethyl)-1-(β-D-glucopyranosyl)-indole;

4-chloro-3-(4-ethoxyphenylmethyl)-1-(β-D-glucopyranosyl)-indole;

3-(5-bromothiophen-2-ylmethyl)-4-chloro-1-(β-D-glucopyranosyl)indole;

3-(4-ethylphenylmethyl)-4-fluoro-1-(β-D-glucopyranosyl)-indole; and 4-methyl-3-(4-cyclopropylphenylmethyl)-1-(β-D-glucopyranosyl)indole.

In an embodiment of the present invention, the SGLT inhibitors are the indole derivatives disclosed in PCT/JP2007/065213, which are represented by Formula (26):

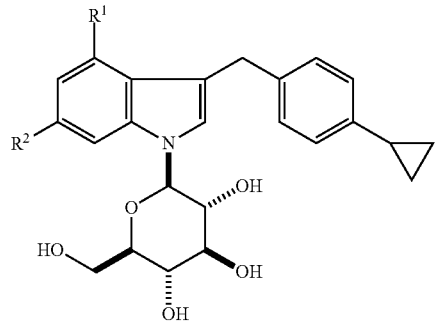

(26)

wherein $R^1$ is fluorine, or chlorine, and $R^2$ is hydrogen, or fluorine, or a pharmaceutically acceptable salt thereof.

Examples of the preferable compounds include:

4-chloro-3-(4-cyclopropylphenylmethyl)-1-(β-D-glucopyranosyl)indole, 3-(4-cyclopropylphenylmethyl)-4-fluoro-1-(β-D-glucopyranosyl)indole, 4-chloro-3-(4-cyclopropylphenylmethyl)-6-fluoro-1-(β-D-glucopyranosyl)indole, and 3-(4-cyclopropylphenylmethyl)-4,6-difluoro-1-(β-D-glucopyranosyl)indole; and a pharmaceutically acceptable salt thereof.

In an embodiment of the present invention, the SGLT inhibitors are the compounds disclosed in United States Patent Application Publication No. 2004/0259819, which are represented by Formula (27):

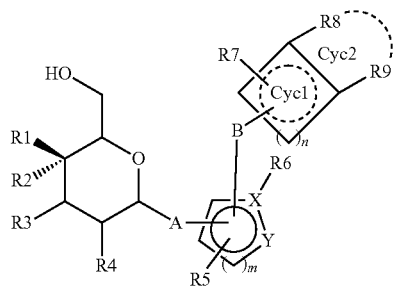

(27)

wherein

R1 and R2 are each independently F or H or one of said radicals R1 and R2 may be OH;

R3 is OH or F, with the proviso that at least one of the radicals R1, R2 and R3 must be F;

R4 is OH;

A is O, NH, CH$_2$, S or a bond;

X is C, O, S or N, with the proviso that X is C when Y is O or S;

Y is N, O or S;

m is 1 or 2;

R5 is hydrogen, F, Cl, Br, I, OH, CF$_3$, NO$_2$, CN, COOH, CO(C$_{1-6}$ alkyl), COO(C$_{1-6}$ alkyl), CONH$_2$, CONH(C$_{1-6}$ alkyl), CON(C$_{1-6}$ alkyl)$_2$, C$_{1-6}$ alkyl, C$_{2-6}$ alkenyl, C$_{2-6}$ alkynyl, C$_{1-6}$ alkoxy, HO—(C$_{1-6}$ alkyl), (C$_{1-6}$ alkyl)-O—(C$_{1-6}$ alkyl), phenyl, benzyl, C$_{1-6}$ alkoxycarbonyl, wherein said CO(C$_{1-6}$ alkyl), COO(C$_{1-6}$ alkyl), CONH(C$_{1-6}$ alkyl), CON(C$_{1-6}$ alkyl)$_2$, C$_{1-6}$ alkyl, C$_{2-6}$ alkenyl, C$_{2-6}$ alkynyl, C$_{1-6}$ alkoxy, HO—(C$_{1-6}$ alkyl), (C$_{1-6}$ alkyl)-O—($C_{1-6}$ alkyl) and $C_{1-6}$ alkoxycarbonyl radicals are optionally substituted with one or more fluorine atoms, $SO_2$—$NH_2$, $SO_2NH(C_{1-6}$ alkyl), $SO_2N(C_{1-6}$ alkyl)$_2$, S—($C_{1-6}$ alkyl), S—$(CH_2)_o$-phenyl, SO—($C_{1-6}$ alkyl), SO—$(CH_2)_o$-phenyl, $SO_2$—($C_{1-6}$ alkyl), $SO_2$—$(CH_2)_o$-phenyl, wherein said $SO_2NH(C_{1-6}$ alkyl), $SO_2N(C_{1-6}$ alkyl)$_2$, S—($C_{1-6}$ alkyl), SO—($C_{1-6}$ alkyl) and $SO_2$—($C_{1-6}$ alkyl) radicals are optionally substituted with one or more fluorine atoms, and wherein the phenyl ring of said S—$(CH_2)_o$-phenyl, SO—$(CH_2)_o$-phenyl and $SO_2$—$(CH_2)_o$-phenyl radicals is optionally mono- or di-substituted with F, Cl, Br, OH, $CF_3$, $NO_2$, CN, $OCF_3$, O—($C_{1-6}$ alkyl), $C_{1-6}$ alkyl or $NH_2$, and wherein o is 0, 1, 2, 3, 4, 5, or 6, $NH_2$, NH—($C_{1-6}$ alkyl), N($C_{1-6}$ alkyl)$_2$, NH($C_{1-7}$ acyl), phenyl or O—$(CH_2)_o$-phenyl, wherein the phenyl ring of said phenyl and O—$(CH_2)_o$-phenyl radicals is optionally mono-, di-, or tri-substituted with F, Cl, Br, I, OH, $CF_3$, $NO_2$, CN, $OCF_3$, O—($C_{1-6}$ alkyl), $C_{1-6}$ alkyl, $NH_2$, NH($C_{1-6}$ alkyl), N($C_{1-6}$ alkyl)$_2$, $SO_2$—$CH_3$, COOH, COO—($C_{1-6}$ alkyl) or $CONH_2$, and wherein o is as hereinabove defined;

or, when Y is S, R5 and R6 taken together with the carbon atoms to which they are attached may form a phenyl ring;

R6 is H, $C_{1-6}$ alkyl, $C_{1-6}$ alkenyl, $C_{3-6}$ cycloalkyl, or phenyl wherein said phenyl radical is optionally substituted with halogen or $C_{1-4}$ alkyl;

B is $C_{0-15}$ alkanediyl, wherein one or more of the carbon atoms in said alkanediyl radical may be replaced, independently of one another, with —O—, —(C=O)—, —CH=CH—, —C≡C—, —S—, —CH(OH)—, —CHF—, —$CF_2$—, —(S=O)—, —($SO_2$)—, —N($C_{1-6}$ alkyl)-, —N($C_{1-6}$ alkyl-phenyl)- or —NH—;

n is 0, 1, 2, 3 or 4;

Cyc1 is a 3-, 4-, 5-, 6- or 7-membered saturated, partially saturated or unsaturated ring, wherein one carbon atom of said ring may be replaced by O, N or S;

R7, R8, and R9 are each independently hydrogen, F, Cl, Br, I, OH, $CF_3$, $NO_2$, CN, COOH, COO($C_{1-6}$ alkyl), CO($C_{1-4}$ alkyl), $CONH_2$, CONH($C_{1-6}$ alkyl), CON($C_{1-6}$ alkyl)$_2$, $C_{1-6}$ alkyl, $C_{2-6}$ alkenyl, $C_{2-6}$ alkynyl, $C_{1-8}$ alkoxy, HO—($C_{1-6}$ alkyl), ($C_{1-6}$ alkyl)-O—($C_{1-6}$ alkyl), wherein said COO($C_{1-6}$ alkyl), CO($C_{1-4}$ alkyl), CONH($C_{1-6}$ alkyl), CON($C_{1-6}$ alkyl)$_2$, $C_{1-6}$ alkyl, $C_{2-6}$ alkenyl, $C_{2-6}$ alkynyl, $C_{1-8}$ alkoxy, HO—($C_{1-6}$ alkyl) and ($C_{1-6}$ alkyl)-O—($C_{1-6}$ alkyl) radicals are optionally substituted with one or more fluorine atoms, $SO_2$—$NH_2$, $SO_2NH(C_{1-6}$ alkyl), $SO_2N(C_{1-6}$ alkyl)$_2$, S—($C_{1-6}$ alkyl), S—$(CH_2)_o$-phenyl, $SCF_3$, SO—($C_{1-6}$ alkyl), SO—$(CH_2)_o$-phenyl, $SO_2$—($C_{1-6}$ alkyl), $SO_2$—$(CH_2)_o$-phenyl, wherein said $SO_2NH(C_{1-6}$ alkyl), $SO_2N(C_{1-6}$ alkyl)$_2$, S—($C_{1-6}$ alkyl), SO—($C_{1-6}$ alkyl) and $SO_2$—($C_{1-6}$ alkyl) radicals are optionally substituted with one or more fluorine atoms, and wherein the phenyl ring of said S—$(CH_2)_o$-phenyl, SO—$(CH_2)_o$-phenyl and $SO_2$—$(CH_2)_o$-phenyl radicals is optionally mono- or di-substituted with F, Cl, Br, OH, $CF_3$, $NO_2$, CN, $OCF_3$, O—($C_{1-6}$ alkyl), $C_{1-6}$ alkyl or $NH_2$, and wherein o is as hereinabove defined, $NH_2$, NH—($C_{1-6}$ alkyl), N($C_{1-6}$ alkyl)$_2$, NHH($C_{1-7}$ acyl), phenyl or O—$(CH_2)_o$-phenyl, wherein the phenyl ring of said phenyl and O—$(CH_2)_o$-phenyl radicals is optionally mono-, di-, or tri-substituted with F, Cl, Br, I, OH, $CF_3$, $NO_2$, CN, $OCF_3$, $C_{1-8}$ alkoxy, $C_{1-6}$ alkyl, $NH_2$, NH($C_{1-6}$ alkyl), N($C_{1-6}$ alkyl)$_2$, $SO_2$—$CH_3$, COOH, COO—($C_{1-6}$ alkyl) or $CONH_2$, and wherein o is as hereinabove defined;

or R8 and R9 taken together with the carbon atoms to which they are attached form a 5-, 6- or 7-membered, saturated, partially saturated or completely unsaturated ring herein referred to as Cyc2, wherein one or two carbon atom(s) in said Cyc2 ring are optionally replaced by N, O or S, and wherein said Cyc2 ring is optionally substituted with $C_{1-6}$ alkyl, $C_{2-5}$ alkenyl or $C_{2-5}$ alkynyl, wherein said $C_{1-6}$ alkyl, $C_{2-5}$ alkenyl and $C_{2-5}$ alkynyl radicals are optionally substituted with F, Cl, OH, $CF_3$, $NO_2$, CN, COO($C_{1-4}$ alkyl), $CONH_2$, CONH($C_{1-4}$ alkyl) or $OCF_3$, and wherein a —$CH_2$— group contained in said $C_{1-6}$ alkyl, $C_{2-5}$ alkenyl and $C_{2-5}$ alkynyl radicals is optionally replaced by —O—;

and pharmaceutically acceptable salts thereof.

In an embodiment of the present invention, the SGLT inhibitors are the compounds in United States Patent Application Publication No. 2005/0014704, which are represented by Formula (28):

wherein: R1, R2 are each independently OH, F or H with the proviso that when R1 is F, R2 cannot be OH;
when R1 is OH, R2 cannot be F; and
when R1 is OH, R2 cannot be OH;

R3 is OH or F, wth the proviso that at least one of said R1, R2, R3 radicals must be F;

A is O, NH, $CH_2$, S or a bond;

R4, R5, and R6 are each independently hydrogen, F, Cl, Br, I, OH, $NO_2$, CN, COOH, CO($C_{1-6}$ alkyl), COO($C_{1-6}$ alkyl), $CONH_2$, CONH($C_{1-6}$ alkyl), CON($C_{1-6}$ alkyl)$_2$, $C_{1-6}$ alkyl, $C_{2-6}$ alkenyl, $C_{2-6}$ alkynyl, $C_{1-6}$ alkoxy, HO($C_{1-6}$ alkyl), ($C_{1-6}$ alkyl)-O—($C_{1-6}$ alkyl), phenyl or benzyl, wherein said CO($C_{1-6}$ alkyl), COO($C_{1-6}$ alkyl), CONH($C_{1-6}$ alkyl), CON($C_{1-6}$ alkyl)$_2$, $C_{1-6}$ alkyl, $C_{2-6}$ alkenyl, $C_{2-6}$ alkynyl, $C_{1-6}$ alkoxy, HO($C_{1-6}$ alkyl), ($C_{1-6}$ alkyl)-O—($C_{1-6}$ alkyl) radicals are optionally substituted with one or more fluorine atoms, $SO_2$—$NH_2$, $SO_2NH(C_{1-6}$ alkyl), $SO_2N(C_{1-6}$ alkyl)$_2$, S—($C_{1-6}$ alkyl), S—$(CH_2)_o$-phenyl, SO—($C_{1-6}$ alkyl), SO—$(CH_2)_o$-phenyl, $SO_2$—($C_{1-6}$ alkyl), $SO_2$—$(CH_2)_o$-phenyl, wherein the phenyl ring of said S—$(CH_2)_o$-phenyl, SO—$(CH_2)_o$-phenyl and $SO_2$—$(CH_2)_o$-phenyl radicals may be mono- or disubstituted with F, Cl, Br, OH, $CF_3$, $NO_2$, CN, $OCF_3$, O—($C_{1-6}$ alkyl), $C_{1-6}$ alkyl or $NH_2$ and wherein o is 0, 1, 2, 3, 4, 5 or 6, $NH_2$, NH—($C_{1-6}$ alkyl), N($C_{1-6}$ alkyl)$_2$, NH($C_{1-7}$ acyl), phenyl, O—$(CH_2)_o$-phenyl, wherein the phenyl ring of said phenyl and O—(CH$_2$)$_o$-phenyl radicals may be mono-, di-, or trisubstituted with F, Cl, Br, I, OH, CF$_3$, NO$_2$, CN, OCF$_3$, O—(C$_{1-6}$ alkyl), C$_{1-6}$ alkyl, NH$_2$, NH(C$_{1-6}$ alkyl), N(C$_{1-6}$ alkyl)$_2$, SO$_2$—CH$_3$, COOH, COO—(C$_{1-6}$ alkyl) or CONH$_2$ and wherein o is as hereinabove defined;

B is C$_{0-15}$ alkanediyl,
wherein one or more carbon atoms in said C$_{0-15}$ alkanediyl radical are, independently of one another, optionally replaced by —O—, —(C=O)—, —CH=CH—, —C≡C—, —S—, —CH(OH)—, —CHF—, —CF$_2$—, —(S=O)—, —(SO$_2$)—, —N(C$_{1-6}$ alkyl)-, —N(C$_{1-6}$ alkyl-phenyl)- or —NH—;

n is 0, 1, 2, 3 or 4;

Cyc1 is a 3-, 4-, 5-, 6-, or 7-membered saturated, partially saturated or unsaturated ring, wherein one carbon atom of said ring may be replaced by O, N or S;

R7, R8, and R9 are each independently hydrogen, F, Cl, Br, I, OH, CF$_3$, NO$_2$, CN, COOH, COO(C$_{1-6}$ alkyl), CO(C$_{1-4}$ alkyl), CONH$_2$, CONH(C$_{1-6}$ alkyl), CON(C$_{1-6}$ alkyl)$_2$, C$_{1-6}$ alkyl, C$_{2-6}$ alkenyl, C$_{2-6}$ alkynyl, C$_{1-8}$ alkoxy, HO—(C$_{1-6}$ alkyl), (C$_{1-6}$ alkyl)-O—(C$_{1-6}$ alkyl),
wherein said COO(C$_{1-6}$ alkyl), CO(CO$_{1-4}$ alkyl), CONH(C$_{1-6}$ alkyl), CON(C$_{1-6}$ alkyl)$_2$, C$_{1-6}$ alkyl, C$_{2-6}$ alkenyl, C$_{2-6}$ alkynyl, C$_{1-8}$ alkoxy, HO—(C$_{1-6}$ alkyl) and (C$_{1-6}$ alkyl)-O—(C$_{1-6}$ alkyl) radicals are optionally substituted with one or more fluorine atoms, SO$_2$—NH$_2$, SO$_2$NH(C$_{1-6}$ alkyl), SO$_2$N(C$_{1-6}$alkyl)$_2$, S—(C$_{1-6}$alkyl), S—(CH$_2$)$_o$-phenyl, SO—(C$_{1-6}$ alkyl), SO—(CH$_2$)$_o$-phenyl, SO$_2$—(C$_{1-6}$ alkyl), SO$_2$—(CH$_2$)$_o$-phenyl,
wherein said SO$_2$NH(C$_{1-6}$ alkyl), SO$_2$N(C$_{1-6}$ alkyl)$_2$, S—(C$_{1-6}$ alkyl), SO—(C$_{1-6}$ alkyl) and SO$_2$—(C$_{1-6}$ alkyl) radicals are optionally substituted with one or more fluorine atoms, and wherein the phenyl ring of said S—(CH$_2$)$_o$-phenyl, SO—(CH$_2$)$_o$-phenyl and SO$_2$—(CH$_2$)$_o$-phenyl radicals is optionally mono- or disubstituted with F, Cl, Br, OH, CF$_3$, NO$_2$, CN, OCF$_3$, O—(C$_{1-6}$ alkyl), C$_{1-6}$ alkyl or NH$_2$, and wherein o is as hereinabove defined, NH$_2$, NH—(C$_{1-6}$alkyl), N(C$_{1-6}$ alkyl)$_2$, NH(C$_{1-7}$ acyl), phenyl or O—(CH$_2$)$_o$-phenyl,
wherein the phenyl ring of said phenyl and O—(CH$_2$)$_o$-phenyl radicals is optionally mono-, di-, or trisubstituted with F, Cl, Br, I, OH, CF$_3$, NO$_2$, CN, OCF$_3$, C$_{1-8}$ alkoxy, C$_{1-6}$ alkyl, NH$_2$, NH(C$_{1-6}$ alkyl), N(C$_{1-6}$ alkyl)$_2$, SO$_2$—CH$_3$, COOH, COO—(C$_{1-6}$ alkyl) or CONH$_2$, and wherein o is as hereinabove defined;

or R8 and R9 taken together with the carbon atoms to which they are attached form a 5-, 6- or 7-membered, saturated, partially saturated or unsaturated ring herein referred to as Cyc2, wherein one or two carbon atom(s) in said Cyc2 ring are optionally replaced by N, O or S,
and wherein said Cyc2 ring is optionally substituted with C$_{1-6}$ alkyl, C$_{2-5}$ alkenyl or C$_{2-5}$ alkynyl,
wherein said C$_{1-6}$ alkyl, C$_{2-5}$ alkenyl and C$_{2-5}$ alkynyl radicals are optionally substituted with F, Cl, OH, CF$_3$, NO$_2$, CN, COO(C$_{1-4}$ alkyl), CONH$_2$, CONH(C$_{1-6}$ alkyl) or OCF$_3$,
and wherein a —CH$_2$— group contained in said C$_{1-6}$ alkyl, C$_{2-5}$ alkenyl and C$_{2-5}$ alkynyl radicals is optionally replaced by —O—;

and pharmaceutically acceptable salts thereof.

DPP4 inhibitors are well known to those skilled in the art, and examples of DPP4 inhibitors can be found in the following publications:

(1) TANABE SEIYAKU Co., Ltd.: WO 02/30891 or the corresponding U.S. patent (U.S. Pat. No. 6,849,622); and WO 02/30890 or the corresponding U.S. patent (U.S. Pat. No. 7,138,397);
(2) Ferring B V: WO 95/15309, WO 01/40180, WO 01/81304, WO 01/81337, WO 03/000250, and WO 03/035057;
(3) Probiodrug: WO 97/40832, EP1082314, WO 99/61431, WO 03/015775;
(4) Novartis A G: WO 98/19998, WO 00/34241, WO 01/96295, U.S. Pat. No. 6,107,317, U.S. Pat. No. 6,110,949, and U.S. Pat. No. 6,172,081;
(5) GlaxoSmithKline: WO 03/002531, WO 03/002530, and WO 03/002553;
(6) Bristol Myers Squibb: WO 01/68603, WO 02/83128, and WO 2005/012249;
(7) Merck & Co.: WO 02/76450, and WO 03/004498;
(8) Srryx Inc.: WO 2005/026148, WO 2005/030751, WO 2005/095381, WO 2004/087053, and WO 2004/103993;
(9) Mitsubishi Pharma Corp.: WO 02/14271, U.S. Pat. No. 7,060,722, U.S. Pat. No. 7,074,794, WO 2003/24942, Japan Patent Publication No. 2002-265439, Japan Patent Publication No. 2005-170792, and WO 2006/088129;
(10) Taisho Pharma Co., Ltd.: WO 2004/020407;
(12) Yamanouchi Pharmaceutical Co., Ltd.: WO 2004/009544;
(13) Kyowa Hakko Kogyo: WO 02/051836;
(14) Kyorin Seiyaku: WO 2005/075421, WO 2005/077900, and WO 2005/082847;
(15) Alantos Pharmaceuticals: WO 2006/116157;
(16) Glenmark Pharmaceuticals: WO 2006/090244, and WO 2005/075426;
(17) Sanwa Kagaku Kenkyusho: WO 2004/067509; and
(18) LG lifescience: WO 2005/037828, and WO 2006/104356.

In a preferable embodiment of the present invention, DPP4 inhibitors are the aliphatic nitrogen-containing 5-membered ring compounds disclosed in U.S. Pat. No. 6,849,622, which are represented by Formula (29):

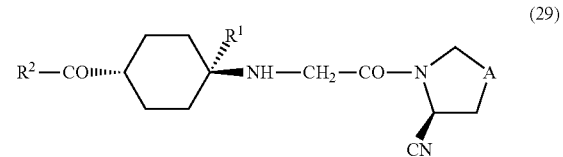

wherein A represents —CH$_2$— or —S—, R$^1$ represents hydrogen atom, a lower alkyl group, a hydroxy lower alkyl group or a lower alkoxy lower alkyl group, and R$^2$ represents (1) a cyclic group which may be substituted, where the cyclic group portion is (i) a monocyclic, bicyclic or tricyclic hydrocarbon group, or (ii) a monocyclic, bicyclic or tricyclic heterocyclic group, or (2) an amino group which may be substituted, or a pharmaceutically acceptable salt thereof.

Examples of the preferable compounds include:
(2S)-2-cyano-1-[trans-4-(dimethylaminocarbonyl)cyclohexyl-amino]acetylpyrrolidine;
(2S)-2-cyano-1-[trans-4-(morpholinocarbonyl)cyclohexyl-amino]acetylpyrrolidine; and
(2S)-2-cyano-1-[trans-4-(4-acetylpiperazin-1-ylcarbonyl)-cyclohexylamino]acetylpyrrolidine;
and a pharmaceutically acceptable salt (e.g., besylate) of the above compounds.

In another preferable embodiment, DPP4 inhibitors are the aliphatic nitrogen-containing 5-membered ring compounds disclosed in U.S. Pat. No. 7,138,397, which are represented by Formula (30):

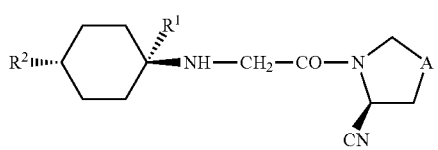

(30)

wherein A is —CH$_2$—, R$^1$ is H, a lower alkyl group, a hydroxy lower alkyl group or a lower alkoxy lower alkyl group, and R$^2$ is a piperazinyl group which may be substituted, or a pharmaceutically acceptable salt thereof.

Examples of the preferable compounds include:
(S)-2-cyano-1-[t-4-(4-acetyl-1-piperazinyl)-1-methyl-r-1-cyclohexylamino]acetylpyrrolidine; and
(S)-2-cyano-1-[t-4-(4-propionyl-1-piperazinyl)-1-methyl-r-1-cyclohexylamino]acetylpyrrolidine;
or a pharmaceutically acceptable salt thereof.

In another preferable embodiment, DPP4 inhibitors are the compounds disclosed in U.S. Pat. No. 7,074,794, which are represented by Formula (31):

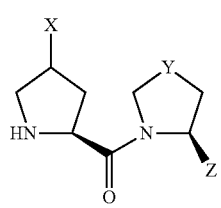

(31)

wherein:
X is —NR$^1$R$^2$ wherein R$^1$ and R$^2$ may be the same or different and each is independently cycloalkylalkyl, arylalkyl, heteroaryl or heteroarylalkyl, or may be bonded to each other to form a heterocycle optionally containing 1 or 2 nitrogen atoms or oxygen atoms, the heterocycle optionally being condensed with an aromatic ring optionally having substituents, and the heterocycle optionally being a Spiro ring,
—NR$^3$COR$^4$ wherein R$^3$ and R$^4$ are the same or different and each is independently a hydrogen atom, alkyl, cycloalkyl, cycloalkylalkyl, aryl, arylalkyl, arylalkenyl, heteroaryl or heteroarylalkyl,
—NR$^5$CONR$^6$R$^7$ or —NR$^5$CH$_2$CH$_2$NR$^6$R$^7$ wherein R$^5$, R$^6$ and R$^7$ are the same or different and each is independently hydrogen atom, alkyl, acyl, cycloalkyl, cycloalkylalkyl, aryl, arylalkyl, heteroaryl or heteroarylalkyl, or R$^6$ and R$^7$ may be bonded to each other to form a heterocycle optionally containing 1 or 2 nitrogen atoms or oxygen atoms, the heterocycle optionally being condensed with an aromatic ring optionally having substituents,
—NR$^8$SO$_2$R$^9$ wherein R$^8$ and R$^9$ are the same or different and each is independently a hydrogen atom, alkyl, cycloalkyl, cycloalkylalkyl, aryl, arylalkyl, heteroaryl or heteroarylalkyl, or
—OR$^{10}$ or —OCOR$^{11}$ wherein R$^{10}$ and R$^{11}$ are each a hydrogen atom, alkyl, cycloalkyl, cycloalkylalkyl, aryl, arylalkyl, heteroaryl or heteroarylalkyl, Y is CH$_2$, CH—OH, S, S=O or SO$_2$,
Z is a hydrogen atom or cyano, and
of the above-mentioned groups, alkyl, aryl, arylalkyl, arylalkenyl, heteroaryl, heteroarylalkyl, cycloalkyl, cycloalkylalkyl and heterocycle each optionally have substituents,
or a pharmaceutically acceptable salt thereof.

In this embodiment, a more preferable compound is 3-[(2S,4S)-4-[4-(3-methyl-1-phenyl-1H-pyrazol-5-yl)piperazin-1-yl]pyrrolidin-2-yl]thiazolidine or a pharmaceutically acceptable salt thereof (e.g., hydrobromide).

In another preferable embodiment of the present invention, the DPP4 inhibitor is Sitagliptin [developing code: MK-0431; proprietary name: Januvia; chemical name: (3R)-3-amino-1-[9-(trifluoromethyl)-1,4,7,8-tetraza-bicyclo[4.3.0]nona-6,8-dien-4-yl]-4-(2,4,5-trifluorophenyl)butan-1-one], or an equivalent thereof such as a pharmaceutically acceptable salt thereof (e.g., phosphate).

In another preferable embodiment of the present invention, the DPP4 inhibitor is Vildagliptin [developing code: LAF237; proprietary name: Galvus; chemical name: (2S)-1-[2-[(3-hydroxy-1-adamantyl)amino]acetyl]pyrrolidine-2-carbonitrile], or an equivalent thereof such as a pharmaceutically acceptable salt thereof.

In still another preferable embodiment of the present invention, the DPP4 inhibitor is Saxagliptin (developing code: BMS-477118; chemical name: (1S,3S,5S)-2-[(2S)-2-amino-2-(3-hydroxy-1-adamantyl)acetyl]-2-azabicyclo[3.1.0]-hexane-3-carbonitrile), or an equivalent thereof such as a pharmaceutically acceptable salt thereof.

In still another preferable embodiment of the present invention, the DPP4 inhibitor is Alogliptin (developing code: SYR-322; chemical name: 6-[(3R)-3-aminopiperidin-1-yl]-1-(2-cyanobenzyl)-3-methylpyrimidin-2,4(1H,3H)-dione), or an equivalent thereof such as a pharmaceutically acceptable salt thereof (e.g., benzoate).

In an embodiment of the present invention, the DPP4 inhibitor is L-threo-isoleucyl pyrrolidide, L-allo-isoleucyl thiazolidide, or L-allo-isoleucyl pyrrolidide, or a pharmaceutically acceptable salt thereof.

As mentioned above, the present invention relates to a method for treating or preventing a disease which is associated with plasma active GLP-1 level comprising administering to a patient in need thereof a therapeutically effective amount of an SGLT inhibitor and a DPP4 inhibitor in combination.

In an embodiment of the present invention, the SGLT inhibitor and the DPP4 inhibitor are administered in amounts sufficient to lower a blood glucose level in the patient.

In another aspect, the present invention relates to a method for increasing plasma active GLP-1 level comprising administering to a patient a therapeutically effective amount of an SGLT inhibitor and a DPP4 inhibitor in combination.

In an embodiment of the present invention, the SGLT inhibitor and the DPP4 inhibitor are administered in amounts sufficient to increase plasma active GLP-1 level in the patient.

A combination therapy of the present invention is useful in treating or preventing a disease which is associated with plasma active GLP-1 level in a mammal such as a human.

In another aspect, the present invention relates to a pharmaceutical composition comprising an SGLT inhibitor, a DPP4 inhibitor and a pharmaceutically acceptable carrier or diluent.

In an embodiment of the present invention, the pharmaceutical composition of the present invention can be used as an agent to lower a blood glucose level in patient.

In an embodiment of the present invention, the pharmaceutical composition of the present invention can be used as an agent to increase plasma active GLP-1 level in a patient.

In an embodiment of the present invention, the pharmaceutical composition of the present invention can be used as an agent for treatment or prevention of a disease which is associated with plasma active GLP-1 level.

Examples of a disease which is associated with plasma active GLP-1 level include diabetes, a condition related to diabetes, obesity, myocardial infarction, stroke, learning or memory impairment, and a neurodegenerative disorder. Examples of a condition related to diabetes include hyperglycemia, impaired glucose tolerance, impaired fasting glucose, insulin resistance, pancreatic β-cell insufficiency, enteroendocrine cell insufficiency, glucosuria, metabolic acidosis, cataracts, diabetic nephropathy, diabetic neuropathy, diabetic retinopathy, diabetic coronary artery disease, diabetic cerebrovascular disease, diabetic peripheral vascular disease, metabolic syndrome, hyperlipidemia, atherosclerosis, hypertension, and obesity. Examples of a neurodegenerative disorder include excitotoxic brain damage caused by severe epileptic seizures, Alzheimer's disease, Parkinson's disease, Huntington's disease, prion-associated disease, motor-neuron disease, traumatic brain injury, spinal cord injury, and peripheral neuropathy. Diabetes includes Type 1 or Type 2 diabetes.

The SGLT inhibitors and the DPP4 inhibitors may be administered to a patient by any conventional route of administration, including intravenous, oral, subcutaneous, intramuscular, intradermal and parenteral administration. The SGLT inhibitors and the DPP4 inhibitors can be administered simultaneously, sequentially, or at separate intervals. When simultaneously administered, the SGLT inhibitor and the DPP4 inhibitor can be incorporated into a single pharmaceutical composition or into separate compositions. When separately administered, therapeutically effective amounts of the SGLT inhibitor and the DPP4 inhibitor can be administered on a different schedule. Each composition may be formulated with common excipients, diluents or carriers, and compressed into tablets, or formulated elixirs or solutions; and as sustained relief dosage forms and the like. The SGLT inhibitor and the DPP4 inhibitor may be administered via different routes.

The SGLT inhibitor and the DPP4 inhibitor are provided in amounts to give a synergistic effect in increasing plasma active GLP-1 level in a patient. Optimal dose of the SGLT inhibitor and the DPP4 inhibitor will vary with patient's age, weight, sex, the particular compound used, the route of administration, and severity of the condition.

In another aspect, the present invention relates to a pharmaceutical composition comprising an SGLT inhibitor and DPP4 inhibitor, together with at least one pharmaceutically acceptable carrier or excipient.

In another aspect, the present invention relates to the use of an SGLT inhibitor and a DPP4 inhibitor for the manufacture of a medicament for the treatment or prevention of a disease associated with plasma active GLP-1 level.

In another aspect, the present invention relates to the use of an SGLT inhibitor and a DPP4 inhibitor for the manufacture of a medicament for the treatment or prevention of diabetes.

In another aspect, the present invention relates to a product comprising an SGLT inhibitor and DPP4 inhibitor as a combined preparation for simultaneous, separate or sequential use in the treatment or prevention of a disease associated with plasma active GLP-1 level.

In another aspect, the present invention relates to a product comprising a SGLT inhibitor and a DPP4 inhibitor as a combined preparation for simultaneous, separate or sequential use in the treatment or prevention of diabetes.

The pharmaceutical composition of the present invention is preferably in unit dosage forms such as tablets, capsules, powders, granules, solutions, suspensions, syrups, aerosol, and suppositories.

The pharmaceutical composition can be formulated with suitable pharmaceutically acceptable carriers and diluents. Suitable pharmaceutically acceptable carriers and diluents are available to those skilled in the art [see, e.g., Remington: The Science and Practice of Pharmacy, (Gennaro et al., eds.), $20^{th}$ Edition, 2000]. Examples of the suitable carriers and diluents can include stearic acid, magnesium stearate, magnesium oxide, sodium and calcium salts of phosphoric and sulfuric acids, magnesium carbonate, talc, gelatin, tragacanth, dextran sulfate sodium, sodium carboxymethylcellulose, methylcellulose, sodium alginate, pectin, dextrin, mannitol, sorbitol, lactose, sucrose, starch, cocoa butter, polyvinyl-pyrrolidone, polyvinyl alcohol, polyethylene glycols, propylene glycol, ethanol, corn oil, cottonseed oil, coconut oil, peanut oil, sesame oil, benzyl alcohol, and other pharmaceutically acceptable materials.

Pharmaceutical compositions may be prepared by methods well known to those skilled in the art, e.g., by means of conventional mixing, dissolving, granulation, levigation, emulsifying, encapsulation, entrapping, lyophilization or spray drying.

In a preferable embodiment of the present invention, the SGLT inhibitor is a compound of Formula (23) or a pharmaceutically acceptable salt thereof, described above.

In another preferable embodiment of the present invention, the SGLT inhibitor is a compound of Formula (24) or a pharmaceutically acceptable salt thereof, described above.

In another preferable embodiment of the present invention, the SGLT inhibitor is a compound of Formula (25) or a pharmaceutically acceptable salt thereof, described above.

In another preferable embodiment of the present invention, the SGLT inhibitor is a compound of Formula (26) or a pharmaceutically acceptable salt thereof, described above.

In a more preferable embodiment of the present invention, the SGLT inhibitor is Sergliflozin, Remogliflozin or Dapagliflozin, or a pharmaceutically acceptable salt thereof.

In a preferable embodiment of the present invention, the DPP4 inhibitor is a compound of Formula (29) or a pharmaceutically acceptable salt thereof, described above.

In another preferable embodiment of the present invention, the DPP4 inhibitor is a compound of Formula (30) or a pharmaceutically acceptable salt thereof, described above.

In another preferable embodiment of the present invention, the DPP4 inhibitor is a compound of Formula (31) or a pharmaceutically acceptable salt thereof, described above.

In another preferable embodiment of the present invention, the DPP4 inhibitor is Sitagliptin, Vildagliptin, Saxagliptin or Alogliptin, or a pharmaceutically acceptable salt thereof.

In a more preferable embodiment of the invention, the SGLT inhibitor is Sergliflozin, Remogliflozin or Dapagliflozin, or a pharmaceutically acceptable salt thereof, and the DPP4 inhibitor is Sitagliptin, Vildagliptin, Saxagliptin or Alogliptin, or a pharmaceutically acceptable salt thereof.

Preferable examples of combination of the SGLT inhibitor and DPP4 inhibitor of the present invention include the following:

(a) The SGLT inhibitor is a compound of Formula (23):

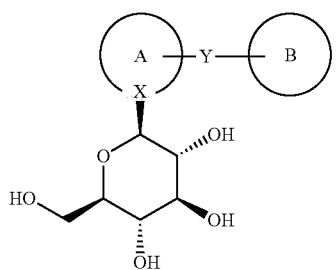

(23)

wherein Ring A and Ring B are one of the followings: (1) Ring A is optionally substituted unsaturated heteromonocyclic, and Ring B is optionally substituted unsaturated heteromonocyclic, optionally substituted unsaturated fused heterobicyclic, or optionally substituted benzene, (2) Ring A is optionally substituted benzene, and Ring B is optionally substituted unsaturated heteromonocyclic, or optionally substituted unsaturated fused heterobicyclic wherein Y is linked to the heterocyclic ring of said fused heterobicyclic, or (3) Ring A is optionally substituted unsaturated fused heterobicyclic, wherein the sugar moiety X-(sugar) and the moiety —Y-(Ring B) are both on the same heterocyclic ring of said fused heterobicyclic, and Ring B is optionally substituted unsaturated heteromonocyclic, optionally substituted unsaturated fused heterobicyclic, or optionally substituted benzene;

X is carbon or nitrogen; and

Y is —(CH$_2$)$_n$— (wherein n is 1 or 2); or a pharmaceutically acceptable salt thereof, and the DPP4 inhibitor is a compound of formula (29):

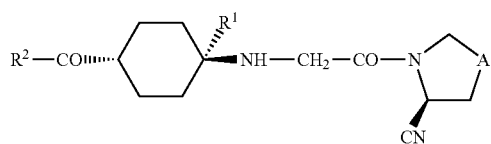

(29)

wherein A represents —CH$_2$— or —S—, R$^1$ represents hydrogen atom, a lower alkyl group, a hydroxy lower alkyl group or a lower alkoxy lower alkyl group, and R$^2$ represents (1) a cyclic group which may be substituted, where the cyclic group portion is (i) a monocyclic, bicyclic or tricyclic hydrocarbon group, or (ii) a monocyclic, bicyclic or tricyclic heterocyclic group, or (2) an amino group which may be substituted, or pharmaceutically acceptable salt thereof; or the DPP4 inhibitor is a compound of Formula (31):

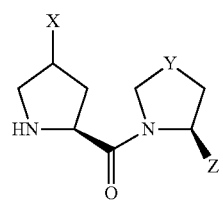

(31)

wherein:

X is —NR$^1$R$^2$ wherein R$^1$ and R$^2$ may be the same or different and each is independently cycloalkylalkyl, arylalkyl, heteroaryl or heteroarylalkyl, or may be bonded to each other to form a heterocycle optionally containing 1 or 2 nitrogen atoms or oxygen atoms, the heterocycle optionally being condensed with an aromatic ring optionally having substituents, and the heterocycle optionally being a spiro ring, —NR$^3$COR$^4$ wherein R$^3$ and R$^4$ are the same or different and each is independently a hydrogen atom, alkyl, cycloalkyl, cycloalkylalkyl, aryl, arylalkyl, arylalkenyl, heteroaryl or heteroarylalkyl, —NR$^5$CONR$^6$R$^7$ or —NR$^5$CH$_2$CH$_2$NR$^6$R$^7$ wherein R$^5$, R$^6$ and R$^7$ are the same or different and each is independently hydrogen atom, alkyl, acyl, cycloalkyl, cycloalkylalkyl, aryl, arylalkyl, heteroaryl or heteroarylalkyl, or R$^6$ and R$^7$ may be bonded to each other to form a heterocycle optionally containing 1 or 2 nitrogen atoms or oxygen atoms, the heterocycle optionally being condensed with an aromatic ring optionally having substituents, —NR$^8$SO$_2$R$^9$ wherein R$^8$ and R$^9$ are the same or different and each is independently a hydrogen atom, alkyl, cycloalkyl, cycloalkylalkyl, aryl, arylalkyl, heteroaryl or heteroarylalkyl, or —OR$^{10}$ or —OCOR$^{11}$ wherein R$^{10}$ and R$^{11}$ are each a hydrogen atom, alkyl, cycloalkyl, cycloalkylalkyl, aryl, arylalkyl, heteroaryl or heteroarylalkyl, Y is CH$_2$, CH—OH, S, S=O or SO$_2$, Z is a hydrogen atom or cyano, and of the above-mentioned groups, alkyl, aryl, arylalkyl, arylalkenyl, heteroaryl, heteroarylalkyl, cycloalkyl, cycloalkylalkyl and heterocycle each optionally have substituents, or a pharmaceutically acceptable salt thereof; or the DPP4 inhibitor is Sitagliptin or a pharmaceutically acceptable salt thereof;

(b) The SGLT inhibitor is a compound of Formula (24):

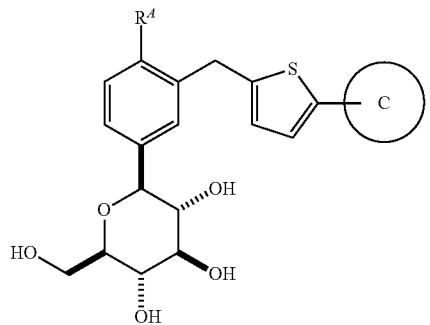

(24)

wherein R$^A$ is a halogen atom, or a lower alkyl group;

Ring C is a phenyl group substituted by 1-3 substituents selected from the group consisting of a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group substituted by 1-3 substituents selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group;

or a pharmaceutically acceptable salt thereof; or a prodrug thereof; and the DPP4 inhibitor is a compound of formula (29):

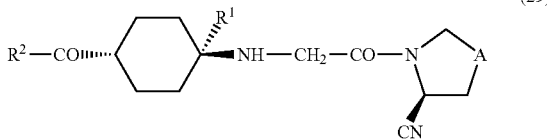

(29)

wherein A represents —CH$_2$— or —S—, R$^1$ represents hydrogen atom, a lower alkyl group, a hydroxy lower alkyl group or a lower alkoxy lower alkyl group, and R$^2$ represents (1) a cyclic group which may be substituted, where the cyclic group portion is (i) a monocyclic, bicyclic or tricyclic hydrocarbon group, or (ii) a monocyclic, bicyclic or tricyclic heterocyclic group, or (2) an amino group which may be substituted, or a pharmaceutically acceptable salt thereof; or the DPP4 inhibitor is a compound of Formula (31):

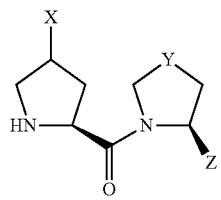

(31)

wherein:

X is —NR$^1$R$^2$ wherein R$^1$ and R$^2$ may be the same or different and each is independently cycloalkylalkyl, arylalkyl, heteroaryl or heteroarylalkyl, or may be bonded to each other to form a heterocycle optionally containing 1 or 2 nitrogen atoms or oxygen atoms, the heterocycle optionally being condensed with an aromatic ring optionally having substituents, and the heterocycle optionally being a spiro ring, —NR$^3$COR$^4$ wherein R$^3$ and R$^4$ are the same or different and each is independently a hydrogen atom, alkyl, cycloalkyl, cycloalkylalkyl, aryl, arylalkyl, arylalkenyl, heteroaryl or heteroarylalkyl, —NR$^5$CONR$^6$R$^7$ or —NR$^5$CH$_2$CH$_2$NR$^6$R$^7$ wherein R$^5$, R$^6$ and R$^7$ are the same or different and each is independently hydrogen atom, alkyl, acyl, cycloalkyl, cycloalkylalkyl, aryl, arylalkyl, heteroaryl or heteroarylalkyl, or R$^6$ and R$^7$ may be bonded to each other to form a heterocycle optionally containing 1 or 2 nitrogen atoms or oxygen atoms, the heterocycle optionally being condensed with an aromatic ring optionally having substituents, —NR$^8$SO$_2$R$^9$ wherein R$^8$ and R$^9$ are the same or different and each is independently a hydrogen atom, alkyl, cycloalkyl, cycloalkylalkyl, aryl, arylalkyl, heteroaryl or heteroarylalkyl, or —OR$^{10}$ or —OCOR$^{11}$ wherein R$^{10}$ and R$^{11}$ are each a hydrogen atom, alkyl, cycloalkyl, cycloalkylalkyl, aryl, arylalkyl, heteroaryl or heteroarylalkyl, Y is CH$_2$, CH—OH, S, S=O or SO$_2$, Z is a hydrogen atom or cyano, and of the above-mentioned groups, alkyl, aryl, arylalkyl, arylalkenyl, heteroaryl, heteroarylalkyl, cycloalkyl, cycloalkylalkyl and heterocycle each optionally have substituents, or a pharmaceutically acceptable salt thereof; or the DPP4 inhibitor is Sitagliptin or a pharmaceutically acceptable salt thereof;

(c) the SGLT inhibitor is a compound of Formula (26):

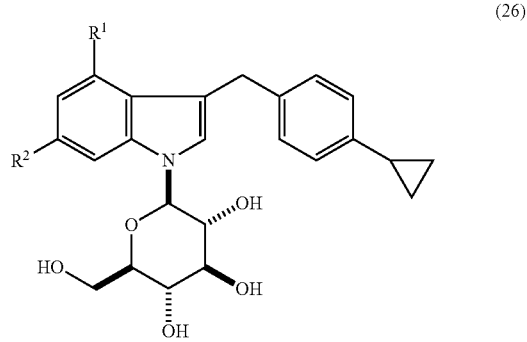

(26)

wherein R$^1$ is fluorine, or chlorine, and R$^2$ is hydrogen, or fluorine, or a pharmaceutically acceptable salt thereof; and the DPP4 inhibitor is a compound of formula (29):

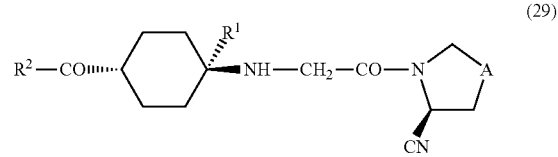

(29)

wherein A represents —CH$_2$— or —S—, R$^1$ represents hydrogen atom, a lower alkyl group, a hydroxy lower alkyl group or a lower alkoxy lower alkyl group, and R$^2$ represents (1) a cyclic group which may be substituted, where the cyclic group portion is (i) a monocyclic, bicyclic or tricyclic hydrocarbon group, or (ii) a monocyclic, bicyclic or tricyclic heterocyclic group, or (2) an amino group which may be substituted, or a pharmaceutically acceptable salt thereof; or the DPP4 inhibitor is a compound of Formula (31):

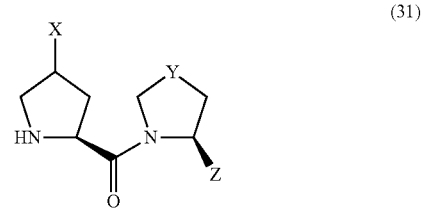

(31)

wherein:

X is —NR$^1$R$^2$ wherein R$^1$ and R$^2$ may be the same or different and each is independently cycloalkylalkyl, arylalkyl, heteroaryl or heteroarylalkyl, or may be bonded to each other to form a heterocycle optionally containing 1 or 2 nitrogen atoms or oxygen atoms, the heterocycle optionally being condensed with an aromatic ring optionally having substituents, and the heterocycle optionally being a spiro ring, —NR$^3$COR$^4$ wherein R$^3$ and R$^4$ are the same or different and each is independently a hydrogen atom, alkyl, cycloalkyl, cycloalkylalkyl, aryl, arylalkyl, arylalkenyl, heteroaryl or heteroarylalkyl, —NR$^5$CONR$^6$R$^7$ or —NR$^5$CH$_2$CH$_2$NR$^6$R$^7$ wherein R$^5$, R$^6$ and R$^7$ are the same or different and each is independently hydrogen atom, alkyl, acyl, cycloalkyl, cycloalkylalkyl, aryl, arylalkyl, heteroaryl or heteroarylalkyl, or R$^6$ and R$^7$ may be bonded to each other to form a heterocycle optionally containing 1 or 2 nitrogen atoms or oxygen atoms, the heterocycle optionally being condensed with an aromatic ring optionally having substituents, —NR$^8$SO$_2$R$^9$ wherein R$^8$ and R$^9$ are the same or different and each is independently a hydrogen atom, alkyl, cycloalkyl, cycloalkylalkyl, aryl, arylalkyl, heteroaryl or heteroarylalkyl, or —OR$^{10}$ or —OCOR$^{11}$ wherein R$^{10}$ and R$^{11}$ are each a hydrogen atom, alkyl, cycloalkyl, cycloalkylalkyl, aryl, arylalkyl, heteroaryl or heteroarylalkyl, Y is CH$_2$, CH—OH, S, S═O or SO$_2$, Z is a hydrogen atom or cyano, and of the above-mentioned groups, alkyl, aryl, arylalkyl, arylalkenyl, heteroaryl, heteroarylalkyl, cycloalkyl, cycloalkylalkyl and heterocycle each optionally have substituents, or a pharmaceutically acceptable salt thereof; or the DPP4 inhibitor is Sitagliptin or a pharmaceutically acceptable salt thereof; and (d) the SGLT inhibitor is selected from:
(i) 1-(β-D-Glucopyranosyl)-4-chloro-3-[5-(6-fluoro-2-pyridyl)-2-thienylmethyl]benzene or a pharmaceutically acceptable salt thereof;
(ii) 3-(5-(4-Fluorophenyl)-2-thienylmethyl)-1-(β-D-glucopyranosyl)-4-methylbenzene or a pharmaceutically acceptable salt thereof;
(iii) 1-(β-D-Glucopyranosyl)-4-chloro-3-[5-(6-fluoro-3-pyridyl)-2-thienylmethyl]benzene or a pharmaceutically acceptable salt thereof;
(iv) 3-(4 Cyclopropylphenylmethyl)-4-fluoro-1-(β-D-glucopyranosyl)indole or a pharmaceutically acceptable salt thereof; and
(v) 3-(4 Cyclopropylphenylmethyl)-4,6-difluoro-1-(β-D-glucopyranosyl)indole or a pharmaceutically acceptable salt thereof; and the DPP4 inhibitor is selected from:
(i) 3-[(2S,4S)-4-[4-(3-methyl-1-phenyl-1H-pyrazol-5-yl)piperazin-1-yl]pyrrolidin-2-ylcarbonyl]thiazolidine or a pharmaceutically acceptable salt thereof (e.g., hydrobromide);
(ii) Sitagliptin (i.e., (3R)-3-amino-1-[3-(trifluoromethyl)-5,6,7,8-tetrahydro-5H-[1,2,4]triazolo[4,3-a]pyrazin-7-yl]-4-(2,4,5-trifluorophenyl)butan-1-one) or a pharmaceutically acceptable salt thereof (e.g., phosphate); and
(iii) (2S)-2-cyano-1-[trans-4-(dimethylaminocarbonyl)cyclohexylamino]acetylpyrrolidine or a pharmaceutically acceptable salt thereof (e.g., besylate).

When the SGLT inhibitor is to be administered orally or parenterally, the dose can typically be selected from a range of about 0.01 to 100 mg/kg/day, preferably about 0.01 to 30 mg/kg/day. When the SGLT inhibitor is to be administered orally, the dose can typically be selected from a range of about 0.03 to 100 mg/kg/day, preferably about 0.03 to 30 mg/kg/day, more preferably about 0.03 to 10 mg/kg/day. When the SGLT inhibitor is to be administered parenterally, the dose can typically be selected from a range of about 0.01 to 30 mg/kg/day, preferably about 0.01 to 10 mg/kg/day, more preferably about 0.01 to 3 mg/kg/day.

When the DPP4 inhibitor is to be administered orally or parenterally, the dose can typically be selected from a range of about 0.01 to 30 mg/kg/day, preferably about 0.01 to 10 mg/kg/day. When the DPP4 inhibitor is to be administered orally, the dose can typically be selected from a range of about 0.03 to 30 mg/kg/day, preferably about 0.03 to 10 mg/kg/day, more preferably about 0.03 to 3 mg/kg/day. When the DPP4 inhibitor is to be administered parenterally, the dose can typically be selected from a range of about 0.01 to 10 mg/kg/day, preferably about 0.01 to 3 mg/kg/day, more preferably about 0.01 to 1 mg/kg/day.

The dose ratio between the respective inhibitors can be selected appropriately, based on patient's age, weight, sex, severity of conditions, and route of administration. For example, the weight:weight dose ratio between the DPP4 inhibitor and the SGLT inhibitor (DPP4 inhibitor: SGLT inhibitor) may typically fall within a range of 1:0.01 to 1:600, preferably 1:0.1 to 1:300, more preferably 1:0.5 to 1:30.

According to the present invention, both the SGLT inhibitor and the DPP4 inhibitor can be administered once or several times at the daily dose described above.

Examples

Example 1

Effects of the SGLT Inhibitor on Plasma Active GLP-1 Level In Glucose-Loaded DPP4-Deficient Rats (a) Animals:

DPP4-Deficient Male Fisher Rats (Purchased from Charles River Japan, Inc.)

(b) Methods:

(b-1) Preparation and Administration of Test Compound

The test compound was suspended in a solution of 0.5% carboxymethyl cellulose containing 0.2% Tween 80 at the doses indicated in Table 1, and administered to the test group orally at a volume of 5 mL/kg. The vehicle control group was orally administered a solution of 0.5% carboxymethyl cellulose containing 0.2% Tween 80 at a volume of 5 mL/kg. Just after the administration of the compound or vehicle, a glucose solution (2 g/kg/5 ml) was given orally.

(b-2) Procedure of Blood Collection and Determination of Plasma Active GLP-1 Level Blood was collected from the caudal vein of an unanesthetized rat just before and 0.5, 1, and 3 hours after glucose loading. Plasma active GLP-1 level was determined by using RAT ENDOCRINE LINCOplex KIT (LINCO Research).

(b-3) Test Compound

The following compound was used:

Compound A:

1-(β-D-glucopyranosyl)-4-chloro-3-[5-(6-fluoro-2-pyridyl)-2-thienylmethyl]benzene (see: United States Patent Application Publication No. 2005/0233988).

(c) Results:

The results are shown in Table 1:

TABLE 1

| Test Compound | Dose (mg/kg) | GLP-1 concentration at each time point (hr) after oral administration (pM) | | | |
|---|---|---|---|---|---|
| | | 0 | 0.5 | 1 | 3 |
| control | | 5.8 ± 1.1 | 10.9 ± 1.6 | 5.3 ± 1.8 | 7.6 ± 1.9 |
| Compound A | 10 | 6.2 ± 1.3 | 24.5 ± 4.7* | 31.3 ± 7.0** | 21.9 ± 2.4** |
| Compound A | 30 | 5.3 ± 0.7 | 24.9 ± 3.8** | 34.1 ± 5.7** | 27.1 ± 2.1** |

The results are expressed as means ± SEM (n = 6).
Statistical differences between groups were assessed by Dunnett's method.
*$P < 0.05$,
**$P < 0.01$ vs. control group.

As shown in the above table 1, Compound A markedly increased plasma active GLP-1 level in DPP4-deficient rats. This result suggests that the augmentation of plasma active GLP-1 by compound A is DPP4-independent. The most likely explanation for the finding in that Compound A increases the secretion of GLP-1.

Example 2

Synergistic Effect of the SGLT Inhibitor and the DPP4 Inhibitor on Plasma Active GLP-1 Level in Glucose-Loaded Normal Rats (a) Animals:
DPP4-Positive Male Fisher Rats (Purchased from Japan SLC, Inc.)
(b) Methods:
(b-1) Preparation and Administration of Test Compounds
Each test compound was suspended in a solution of 0.5% carboxymethyl cellulose containing 0.2% Tween 80 at the doses indicated in Table 2, and administered to the test group orally at a volume of 5 mL/kg. The vehicle control group was orally administered a solution of 0.5% carboxymethyl cellulose containing 0.2% Tween 80 at a volume of 5 mL/kg. Just after the administration of the compound or vehicle, a glucose solution (2 g/kg/5 mL) was given orally.
(b-2) Procedure of Blood Collection and Determination of Plasma Active GLP-1 Level
Blood was collected from the caudal vein of an unanesthetized rat just before and 0.2, 0.5, 1, and 2 hours after glucose loading. Plasma active GLP-1 level was determined by using RAT ENDOCRINE LINCOplex KIT (LINCO Research).
(b-3) Test Compounds
The following compounds were used:
Compound A:
1-(β-D-Glucopyranosyl)-4-chloro-3-[5-(6-fluoro-2-pyridyl)-2-thienylmethyl]benzene; and
Compound B:
(2S)-2-Cyano-1-[trans-4-(morpholinocarbonyl)cyclohexylamino]acetylpyrrolidine (see: U.S. Pat. No. 6,849,622).
(c) Results:
The results are shown in Table 2:

As shown in Table 2, when the SGLT inhibitor was given separately, there was no increase in the active GLP-1 levels. The DPP4 inhibitor treatment alone increased in plasma active GLP-1 only at 0.2 hr. On the other hand, the combination treatment of Compound A and Compound B produced marked and prolonged increase of plasma active GLP-1 level in DPP4-positive rats.

Example 3

Effects of the SGLT Inhibitor and the DPP4 Inhibitor on Plasma Active GLP-1 Level in Glucose-Loaded Diabetic Mice (a) Animals:
Male BKS.Cg-+$Lepr^{db}$/+$Lepr^{db}$/Jcl mice; an Animal Model of Type 2 Diabetes (Purchased from CLEA Japan, Inc.)
(b) Methods:
(b-1) Preparation and Administration of Test Compounds
Each test compound was suspended in a solution of 0.5% carboxymethyl cellulose containing 0.2% Tween 80 at the doses indicated in Table 3, and administered to the test group orally at a volume of 5 mL/kg. The vehicle control group was orally administered a solution of 0.5% carboxymethyl cellulose containing 0.2% Tween 80 at a volume of 5 mL/kg. Just after the administration of the compound or vehicle, a glucose solution (2 g/kg/5 mL) was given orally.
(b-2) Procedure of Blood Collection and Determination of Plasma Active GLP-1 Level
Blood was collected from the caudal vein of an unanesthetized mice just before and 0.5, 1, and 2 hours after glucose loading. Plasma active GLP-1 level was determined by using RAT ENDOCRINE LINCOplex KIT (LINCO Research).
(b-3) Test Compounds
The following compounds were used:
Compound A:
1-(β-D-Glucopyranosyl)-4-chloro-3-[5-(6-fluoro-2-pyridyl)-2-thienylmethyl]benzene; and
Compound B:
(2S)-2-Cyano-1-[trans-4-(morpholinocarbonyl)cyclohexylamino]acetylpyrrolidine.

TABLE 2

| Test Compound | Dose (mg/kg) | GLP-1 concentration at each time point (hr) after oral administration (pM) | | | | |
|---|---|---|---|---|---|---|
| | | 0 | 0.2 | 0.5 | 1 | 2 |
| Control | | 6.7 ± 0.3 | 5.9 ± 0.6 | 7.3 ± 0.3 | 6.8 ± 0.5 | 6.6 ± 0.4 |
| Compound A | 10 | 7.7 ± 0.4 | 7.9 ± 0.2 | 10.2 ± 1.0 | 9.5 ± 0.6 | 9.6 ± 0.8 |
| Compound A | 30 | 5.9 ± 0.3 | 7.1 ± 0.3 | 6.7 ± 0.4 | 7.5 ± 0.9 | 9.0 ± 0.9 |
| Compound B | 3 | 7.2 ± 0.6 | 9.8 ± 0.7* | 9.4 ± 0.4 | 8.3 ± 0.3 | 7.9 ± 0.5 |
| Compound A + Compound B | 10 + 3 | 7.4 ± 0.3 | 10.1 ± 1.2** | 13.6 ± 1.0** | 12.6 ± 1.1** | 16.8 ± 3.5** |
| Compound A + Compound B | 30 + 3 | 6.4 ± 0.3 | 10.4 ± 1.3** | 14.0 ± 1.6** | 14.4 ± 1.4** | 21.8 ± 3.1** |

The results are expressed as means ± SEM (n = 6).
Statistical differences between groups were assessed by Dunnett's method.
*$P < 0.05$,
**$P < 0.01$ vs. control group.

(c) Results:

The results are shown in Table 3.

TABLE 3

| Test Compound | Dose (mg/kg) | GLP-1 concentration at each time point (hr) after oral administration (pM) | | | |
|---|---|---|---|---|---|
| | | 0 | 0.5 | 1 | 2 |
| Control | | 37.2 ± 11.6 | 37.0 ± 11.7 | 33.9 ± 11.1 | 40.8 ± 13.5 |
| Compound A | 10 | 20.3 ± 9.6 | 42.6 ± 13.4 | 49.4 ± 12.0 | 30.9 ± 8.2 |
| Compound B | 3 | 18.4 ± 5.1 | 30.0 ± 5.5 | 46.5 ± 10.1 | 25.0 ± 4.1 |
| Compound A + Compound B | 10 + 3 | 22.8 ± 3.5 | 109.2 ± 20.4** | 82.4 ± 11.6* | 55.2 ± 4.6 |

The results are expressed as means ± SEM (n = 8).
Statistical differences between groups were assessed by Dunnett's method.
*P < 0.05,
**P < 0.01 vs. control group.

As shown in table 3, not only in normal animal but also in animal model of Type 2 diabetes, the combination of Compound A and Compound B significantly increased plasma active GLP-1 level.

Example 4

Synergistic Effect of the SGLT Inhibitor and the DPP4 Inhibitor on Plasma Active GLP-1 Level in Glucose-Loaded Normal Rats (a) Animals:
DPP4-Positive Male Fisher Rats (Purchased from Japan SLC, Inc.)

(b) Methods:

(b-1) Preparation and Administration of Test Compounds

Each test compound was suspended in a solution of 0.5% carboxymethyl cellulose containing 0.2% Tween 80 at the doses indicated in Table 4, 5 or 6, and administered to the test group orally at a volume of 5 mL/kg. The vehicle control group was orally administered a solution of 0.5% carboxymethyl cellulose containing 0.2% Tween 80 at a volume of 5 mL/kg. Just after the administration of the compound or vehicle, a glucose solution (2 g/kg/5 mL) was given orally.

(b-2) Procedure of Blood Collection and Determination of Plasma Active GLP-1 Level Blood was collected from the caudal vein of an unanesthetized rat at appropriate time described in the table. Plasma active GLP-1 level was determined by using RAT ENDOCRINE LINCOplex KIT (LINCO Research).

(b-3) Test Compounds

The following compounds were used for the tests:

Compound C:
3-(5-(4-Fluorophenyl)-2-thienylmethyl)-1-(β-D-glucopyranosyl)-4-methylbenzene (see: United States Patent Application Publication No. 2005/0233988);

Compound D:
1-(β-D-Glucopyranosyl)-4-chloro-3-[5-(6-fluoro-3-pyridyl)-2-thienylmethyl]benzene (see: United States Patent Application Publication No. 2005/0233988);

Compound E:
3-(4-Cyclopropylphenylmethyl)-4-fluoro-1-(β-D-glucopyranosyl)indole (see: WO 2008/013322 pamphlet);

Compound F:
3-(4-Cyclopropylphenylmethyl)-4,6-difluoro-1-(β-D-glucopyranosyl)indole (see: WO 2008/013322 pamphlet);

Compound G:
3-[(2S,4S)-4-[4-(3-methyl-1-phenyl-1H-pyrazol-5-yl)piperazin-1-yl]pyrrolidin-2-ylcarbonyl]thiazolidine hydrobromide (see U.S. Pat. No. 7,074,794);

Compound H:
Sitagliptin phosphate; and

Compound I:
(2S)-2-cyano-1-[trans-4-(dimethylaminocarbonyl)cyclohexylamino]acetylpyrrolidine besylate (see: U.S. Pat. No. 6,849,622).

(c) Results:

The results are shown in Tables 4-6:

TABLE 4

| Test Compound | Dose (mg/kg) | GLP-1 concentration at each time point (hr) after oral administration (pM) | | | | |
|---|---|---|---|---|---|---|
| | | 0 | 0.2 | 0.5 | 1 | 2 |
| Control | | 4.4 ± 1.3 | 10.1 ± 2.3 | 6.8 ± 1.9 | 6.0 ± 0.9 | 5.4 ± 1.3 |
| Compound G | 5 | 5.4 ± 1.8 | 23.1 ± 3.8* | 9.3 ± 2.0 | 6.2 ± 1.5 | 7.0 ± 1.7 |
| Compound C + Compound G | 30 + 5 | 5.4 ± 1.1 | 25.8 ± 5.1** | 24.0 ± 3.2** | 22.6 ± 7.2* | 24.3 ± 6.2** |
| Compound E + Compound G | 30 + 5 | 9.0 ± 1.4 | 26.0 ± 4.5** | 28.0 ± 3.6** | 28.6 ± 2.4** | 37.7 ± 4.3** |
| Compound D + Compound G | 30 + 5 | 5.2 ± 0.9 | 22.6 ± 2.6* | 25.7 ± 3.2** | 32.6 ± 3.0** | 31.7 ± 1.4** |

The results are expressed as means ± SEM (n = 5 or 6).
Statistical differences between groups were assessed by Dunnett's method.
*p < 0.05,
**p < 0.01 vs. control group.

TABLE 5

| Test Compound | Dose (mg/kg) | GLP-1 concentration at 2 hr after oral administration (pM) |
|---|---|---|
| Control | | 3.8 ± 0.4 |
| Compound H | 10 | 4.1 ± 0.5 |
| Compound C + Compound H | 30 + 10 | 15.9 ± 1.0** |
| Compound E + Compound H | 30 + 10 | 19.1 ± 2.0** |
| Compound F + Compound H | 30 + 10 | 16.7 ± 1.5** |

The results are expressed as means ± SEM (n = 6).
Statistical differences between groups were assessed by Dunnett's method.
*p < 0.05,
**p < 0.01 vs. control group.

TABLE 6

| Test Compound | Dose (mg/kg) | GLP-1 concentration at 2 hr after oral administration (pM) |
|---|---|---|
| Control | | 5.5 ± 2.5 |
| Compound I | 10 | 4.0 ± 0.6 |
| Compound C + Compound I | 30 + 10 | 21.4 ± 2.3** |
| Compound E + Compound I | 30 + 10 | 26.1 ± 3.1** |

The results are expressed as means ± SEM (n = 5 or 6).
Statistical differences between groups were assessed by Dunnett's method.
*p < 0.05,
**p < 0.01 vs. control group.

As shown in Tables 4-6, the combination treatment of an SGLT inhibitor and a DPP4 inhibitor produced marked and prolonged increase of plasma active GLP-1 level in DPP4-positive rats.

These results suggest that the combination of an SGLT inhibitor and a DPP4 inhibitor provided substantial elevation of plasma active GLP-1 level.

According to the present invention, a combination of an SGLT inhibitor and a DPP4 inhibitor can be used to prevent or treat some sort of disease which is associated with plasma active GLP-1 level with a dose of a DPP4 inhibitor substantially lower than that currently contemplated for use in monotherapy for said condition, thereby reducing the likelihood of unwanted side-effects associated with inhibition of DPP4 activity.

The invention claimed is:

1. A method for increasing plasma active GLP-1 level comprising administering to a patient a therapeutically effective amount of an SGLT inhibitor and a DPP4 inhibitor, wherein the SGLT inhibitor is a compound selected from the group consisting of:
   1-(β-D-Glucopyranosyl)-4-chloro-3-[5-(6-fluoro-2-pyridyl)-2-thienylmethyl]benzene or a pharmaceutically acceptable salt thereof;
   1-(β-D-Glucopyranosyl)-4-chloro-3-[5-(6-fluoro-3-pyridyl)-2-thienylmethyl]benzene or a pharmaceutically acceptable salt thereof;
   3-(4-Cyclopropylphenylmethyl)-4-fluoro-1-(β-D-glucopyranosyl)indole or a pharmaceutically acceptable salt thereof; and
   3-(4 Cyclopropylphenylmethyl)-4,6-difluoro-1-(β-D-glucopyranosyl)indole or a pharmaceutically acceptable salt thereof and;
   the DPP4 inhibitor is a compound selected from the group consisting of:
   3-[(2S,4S)-4-[4-(3-methyl-1-phenyl-1H-pyrazol-5-yl]piperazin-1-yl]pyrrolidin-2-ylcarbonyl)thiazolidine or a pharmaceutically acceptable salt thereof;
   Sitagliptin or a pharmaceutically acceptable salt thereof; and
   (2S)-2-cyano-1-[trans-4-(dimethylaminocarbonyl)cyclohexylamino]acetylpyrrolidine or a pharmaceutically acceptable salt thereof.

2. A method for treating a disease which is associated with plasma active GLP-1 level comprising administering to a patient in need thereof a therapeutically effective amount of an SGLT inhibitor and a DPP4 inhibitor, wherein the SGLT inhibitor is a compound selected from the group consisting of:
   1-(β-D-Glucopyranosyl)-4-chloro-3-[5-(6-fluoro-2-pyridyl)-2-thienylmethyl]benzene or a pharmaceutically acceptable salt thereof;
   3-(5-(4-Fluorophenyl)-2-thienylmethyl)-1-(β-D-glucopyranosyl)-4-methylbenzene or a pharmaceutically acceptable salt thereof;
   1-(β-D-Glucopyranosyl)-4-chloro-3-[5-(6-fluoro-3 pyridyl)-2-thienylmethyl]benzene or a pharmaceutically acceptable salt thereof;
   3-(4-Cyclopropylphenylmethyl)-4-fluoro-1-(β-D-glucopyranosyl)indole or a pharmaceutically acceptable salt thereof; and
   3-(4-Cyclopropylphenylmethyl)-4,6-difluoro-1-(β-D-glucopyranosyl)indole or a pharmaceutically acceptable salt thereof; and
   the DPP4 inhibitor is a compound selected from the group consisting of:
   3-[(2S,4S)-4-[4-(3-methyl-1-phenyl-1H-pyrazol-5-yl piperazin-1-yl]pyrrolidin-2-ylcarbonyl]thiazolidine or a pharmaceutically acceptable salt thereof;
   Sitagliptin or a pharmaceutically acceptable salt thereof; and
   (2S)-2-cyano-1-[trans-4-(dimethylaminocarbonyl)cyclohexylamino]acetylpyrrolidine or a pharmaceutically acceptable salt thereof; and wherein the disease which is associated with plasma active GLP-1 level is selected from the group consisting of diabetes, a condition related to diabetes, myocardial infarction, stroke and a neurodegenerative disorder, and wherein the condition related to diabetes is selected from the group consisting of hyperglycemia, impaired glucose tolerance, impaired fasting glucose, insulin resistance, pancreatic beta-cell insufficiency, enteroendocrine cell insufficiency, glucosuria, metabolic acidosis, cataracts, diabetic nephropathy, diabetic neuropathy, diabetic retinopathy, diabetic coronary artery disease, diabetic cerebrovascular disease, diabetic peripheral vascular disease, metabolic syndrome, hyperlipidemia, atherosclerosis, hypertension, and obesity.

3. A method according to claim 2, wherein the disease associated with plasma active GLP-1 level is a neurodegenerative disorder, which is selected from excitotoxic brain damage caused by severe epileptic seizures, Alzheimer's disease, Parkinson's disease, Huntington's disease, prion-associated disease, motor-neuron disease, traumatic brain injury, spinal cord injury, and peripheral neuropathy.

4. The method according to claim 1 or 2, wherein the SGLT inhibitor is 3-(5-(4-fluorophenyl)-2-thienylmethyl)-1-(β-D-glucopyranosyl)-4-methylbenzene or a pharmaceutically acceptable salt thereof; and the DPP4 inhibitor is 3-[(2S,4S)-4-[4-(3-methyl-1-phenyl-1H-pyrazol-5-yl)piperazin-1-yl]pyrrolidin-2-ylcarbonyl]thiazolidine or a pharmaceutically acceptable salt thereof.

5. The method according to claim 1 or 2, wherein the SGLT inhibitor is 3-(5-(4-fluorophenyl)-2-thienylmethyl)-1-(β-D-glucopyranosyl)-4-methylbenzene or a pharmaceutically acceptable salt thereof; and the DPP4 inhibitor is Sitagliptin or a pharmaceutically acceptable salt thereof.

6. A pharmaceutical composition comprising an SGLT inhibitor, a DPP4 inhibitor and a pharmaceutically acceptable carrier or diluent, wherein the SGLT inhibitor and the DPP4 inhibitor are in amounts sufficient to increase plasma active GLP-1 level in a patient, wherein the SGLT inhibitor is a compound selected from the group consisting of:

- 1-(β-D-Glucopyranosyl)-4-chloro-3-[5-(6-fluoro-2-pyridyl)-2-thienylmethyl]benzene or a pharmaceutically acceptable salt thereof;
- 3-(5-(4-Fluorophenyl)-2-thienylmethyl)-1-(β-D-glucopyranosyl)-4-methylbenzene or a pharmaceutically acceptable salt thereof;
- 1-(β-D-Glucopyranosyl)-4-chloro-3-[5-(6-fluoro-3-pyridyl)-2-thienylmethyl]benzene or a pharmaceutically acceptable salt thereof;
- 3-(4-Cyclopropylphenylmethyl)-4-chloro-3-[5-(6-fluoro-3-pyridyl)-2-thienylmethyl]benzene or a pharmaceutically acceptable salt thereof; and
- 3-(4-Cyclopropylphenylmethyl)-4,6-difluoro-1-(β-D-glucopyranosyl)indole or a pharmaceutically acceptable salt thereof; and the DPP4 inhibitor is a compound selected from the group consisting of:

- 3-[(2S,4S)-4-[4-(3-methyl-1-phenyl-1H-pyrazol-5-yl)piperazin-1-yl]pyrrolidin-2-ylcarbonyl]thiazolidine or a pharmaceutically acceptable salt thereof;
- Sitagliptin or a pharmaceutically acceptable salt thereof; and
- (2S)-2-cyano-1-[trans-4-(dimethylaminocarbonyl)cyclohexylamino]acetylpyrrolidine or a pharmaceutically acceptable salt thereof.

7. A product comprising an SGLT inhibitor and a DPP4 inhibitor as a combined preparation for simultaneous, separate or sequential administration for treating a disease associated with plasma active GLP-1 level, wherein the SGLT inhibitor is a compound selected from the group consisting of:

- 1-(β-D-Glucopyranosyl)-4-chloro-3-[5-(6-fluoro-2-pyridyl)-2-thienylmethyl]-benzene or a pharmaceutically acceptable salt thereof;
- 3-(5-(4-Fluorphenyl-2-thienylmethyl)-1-(β-D-glucopyranosyl)-4-methylbenzene or a pharmaceutically acceptable salt thereof;
- 1-(β-D-Glucopyranosyl)-4-chloro-3-[5-(6-fluoro-3-pyridyl)-2-thienylmethyl]benzene or a pharmaceutically acceptable salt thereof;
- 3-(4-Cyclopropylphenylmethyl)-4-fluoro-1-(β-D-glucopyranosyl)indole or a pharmaceutically acceptable salt thereof; and
- 3-(4-Cyclopropylphenylmethyl-4,6-difluoro-1-(β-D-glucopyranosyl)indole or a pharmaceutically acceptable salt thereof; and the DPP4 inhibitor is a compound selected from the group consisting of:

- 3-[(2S,4S)-4-[4-(3-methyl-1-phenyl-1H-pyrazol-5-yl)piperazin-1-yl]pyrrolidin-2-ylcarbonyl]thiazolidine or a pharmaceutically acceptable salt thereof;
- Sitagliptin or a pharmaceutically acceptable salt thereof; and
- (2S)-2-cyano-1-[trans-4-(dimethylaminocarbonyl)cyclohexylamino]acetylpyrrolidine or a pharmaceutically acceptable salt thereof; and wherein the disease which is associated with plasma active GLP-1 level is selected from the group consisting of diabetes, a condition related to diabetes, myocardial infarction, stroke and a neurodegenerative disorder, and wherein the condition related to diabetes is selected from the group consisting of hyperglycemia, impaired glucose tolerance, impaired fasting glucose, insulin resistance, pancreatic beta-cell insufficiency, enteroendocrine cell insufficiency, glucosuria, metabolic acidosis, cataracts, diabetic nephropathy, diabetic neuropathy, diabetic retinopathy, diabetic coronary artery disease, diabetic cerebrovascular disease, diabetic peripheral vascular disease, metabolic syndrome, hyperlipidemia, atherosclerosis, hypertension, and obesity.

* * * * *

UNITED STATES PATENT AND TRADEMARK OFFICE
CERTIFICATE OF CORRECTION

PATENT NO. : 8,853,385 B2  
APPLICATION NO. : 12/863429  
DATED : October 7, 2014  
INVENTOR(S) : Ueta et al.

Page 1 of 1

It is certified that error appears in the above-identified patent and that said Letters Patent is hereby corrected as shown below:

In the Claims

In Claim 1, at Column 47, Line 57:
Please insert:
-- 3-(5-(4-Fluorophenyl)-2-thienylmethyl)-1-(β-D-glucopyranosyl)-4-methylbenzene or a pharmaceutically acceptable salt thereof; --

Signed and Sealed this
Eleventh Day of August, 2020

Andrei Iancu
*Director of the United States Patent and Trademark Office*